(12) United States Patent
Nielsen Søderberg et al.

(10) Patent No.: US 12,077,578 B2
(45) Date of Patent: Sep. 3, 2024

(54) COMPOSITIONS AND METHODS FOR TREATING SYNUCLEINOPATHIES

(71) Applicant: H. Lundbeck A/S, Valby (DK)

(72) Inventors: Josefine Nielsen Søderberg, Valby (DK); Pekka Kallunki, Valby (DK); Louise Buur, Valby (DK); Frank Larsen, Valby (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 18/341,437

(22) Filed: Jun. 26, 2023

(65) Prior Publication Data

US 2024/0025979 A1    Jan. 25, 2024

Related U.S. Application Data

(63) Continuation of application No. PCT/EP2022/075402, filed on Sep. 13, 2022.

(30) Foreign Application Priority Data

Sep. 16, 2021 (EP) .................................. 21197120

(51) Int. Cl.
| | | |
|---|---|---|
| A61K 39/395 | (2006.01) | |
| A61K 47/22 | (2006.01) | |
| A61K 47/26 | (2006.01) | |
| C07K 16/18 | (2006.01) | |
| A61K 39/00 | (2006.01) | |

(52) U.S. Cl.
CPC ........ *C07K 16/18* (2013.01); *A61K 39/39591* (2013.01); *A61K 47/22* (2013.01); *A61K 47/26* (2013.01); *A61K 2039/545* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 10,358,482 B2 | 7/2019 | Kallunki et al. | |
| 10,358,483 B2 | 7/2019 | Kallunki et al. | |
| 10,358,484 B2 | 7/2019 | Kallunki et al. | |
| 10,364,285 B2 | 7/2019 | Kallunki et al. | |
| 10,640,554 B2 | 5/2020 | Kallunki et al. | |
| 10,647,763 B2 | 5/2020 | Kallunki et al. | |
| 10,647,764 B2 | 5/2020 | Kallunki et al. | |
| 10,800,836 B2 | 10/2020 | Kallunki et al. | |
| 11,421,024 B2 | 8/2022 | Kallunki et al. | |
| 11,524,995 B2 | 12/2022 | Kallunki et al. | |
| 11,542,323 B2 | 1/2023 | Kallunki et al. | |
| 2017/0015739 A1 | 1/2017 | Kallunki et al. | |
| 2018/0127491 A1 | 5/2018 | Kallunki et al. | |
| 2018/0127492 A1 | 5/2018 | Kallunki et al. | |
| 2018/0179270 A1 | 6/2018 | Kallunki et al. | |
| 2019/0367594 A1 | 12/2019 | Kallunki et al. | |
| 2019/0367595 A1 | 12/2019 | Kallunki et al. | |
| 2019/0382473 A1 | 12/2019 | Kallunki et al. | |
| 2021/0061892 A1 | 3/2021 | Kallunki et al. | |
| 2021/0147522 A1 | 5/2021 | Kallunki et al. | |
| 2023/0312693 A1 | 10/2023 | Kallunki et al. | |

FOREIGN PATENT DOCUMENTS

| | | | |
|---|---|---|---|
| WO | 2005/013889 A2 | 2/2005 | |
| WO | 2015/001504 A2 | 1/2015 | |
| WO | 2017009312 A1 | 1/2017 | |
| WO | 2017/176835 A2 | 10/2017 | |
| WO | 2018091444 A1 | 5/2018 | |
| WO | WO-2018178950 A1 * | 10/2018 | ............. A61P 25/00 |

OTHER PUBLICATIONS

U.S. Appl. No. 17/992,403, filed Nov. 22, 2022, Pekka Kallunki.
U.S. Appl. No. 17/088,307, filed Nov. 3, 2020, Pekka Kallunki, U.S. Pat. No. 11,542,323.
U.S. Appl. No. 17/004,447, filed Aug. 3, 2022, Pekka Kallunki, U.S. Pat. No. 11,421,024.
U.S. Appl. No. 16/895,471, filed Jun. 8, 2020, Pekka Kallunki, U.S. Pat. No. 11,524,995.
U.S. Appl. No. 16/443,249, filed Jun. 17, 2019, Pekka Kallunki, U.S. Pat. No. 10,640,554.
U.S. Appl. No. 16/443,225, filed Jun. 17, 2019, Pekka Kallunki, U.S. Pat. No. 10,647,764.
U.S. Appl. No. 16/443,187, filed Jun. 17, 2019, Pekka Kallunki, U.S. Pat. No. 10,647,763.
U.S. Appl. No. 15/812,410, filed Nov. 14, 2017, Pekka Kallunki, U.S. Pat. No. 10,358,484.
U.S. Appl. No. 15/812,363, filed Nov. 14, 2017, Pekka Kallunki, U.S. Pat. No. 10,364,285.
U.S. Appl. No. 15/812,303, filed Nov. 14, 2017, Pekka Kallunki, U.S. Pat. No. 10,358,483.
U.S. Appl. No. 15/812,251, filed Nov. 14, 2017, Pekka Kallunki, U.S. Pat. No. 10,358,482.
U.S. Appl. No. 15/207,859, filed Jul. 12, 2016, Pekka Kallunki, U.S. Pat. No. 10,800,836.
A Study of Lu AF82422 in Participants With Multiple System Atrophy—Full Text View—ClinicalTrials.gov, (NCT05104476), Nov. 3, 2021, 7 pages.

(Continued)

*Primary Examiner* — Yunsoo Kim
(74) *Attorney, Agent, or Firm* — Nelson Mullins Riley & Scarborough LLP; Jane E. Remillard, Esq.; Christopher L. Frank

(57) ABSTRACT

The present invention relates to stable and low viscosity liquid pharmaceutical compositions comprising antibodies binding to human alpha synuclein and to methods for use of antibodies binding to human alpha synuclein for treating synucleinopathies or prodromal synucleinopathy, incl. suitable doses and/or dosing regimens. These antibodies for use in treatment of synucleinopathies or prodromal synucleinopathy may be formulated in the stable and low viscosity liquid pharmaceutical compositions of the invention.

16 Claims, 14 Drawing Sheets
Specification includes a Sequence Listing.

(56) References Cited

OTHER PUBLICATIONS

Jankovic, J. et al., "Safety and Tolerability of Multiple Ascending Doses of PRX002/RG7935, an Anti-alpha-Synuclein Monoclonal Antibody, in Patients With Parkinson Disease," JAMA Neurol., vol. 75(10):1206-1214 (2018).

Luk, K. et al. "Intracerebral inoculation of pathological alpha-synuclein initiates a rapidly progressive neurodegenerative alpha-synucleinopathy in mice," J. Exp. Med., vol. 209(5):975-986 (2012).

Luk, K. et al., "Pathological alpha-Synuclein Transmission Initiates Parkinson-like Neurodegeneration in Non-transgenic Mice," Science, vol. 338(6109): 949-953 (2012).

Mollenhauer, B. et al., "Longitudinal Analyses of Cerebrospinal Fluid alpha-Synucleinin Prodromal and Early Parkinson's Disease," Mov Disord., vol. 34(9): 1354-1364 (2019).

Peelaerts, W. et al., "Alpha-synuclein strains cause distrinct synucleinopathies after local and systemic administration," Nature, vol. 522 (7556) 340-344 (2015).

Polinski, N. et al., "Best Practices for Generating and Using Alpha-Synuclein Pre-Formed Fibrils to Model Parkinson's Disease in Rodents," J. Parkinsons Dis., vol. 8(2): 303-322 (2018).

Recasens, A. PhD, et al. "Lewy Body Extracts from Parkinson-nDisease Brains Trigger Alpha-Synuclein Pathology and Neurodegeneration in Mice and Monkeys," Ann Neurol., vol. 75:351-362 (2014).

Tateno, F. et al., "Alpha-synuclein in the Cerebrospinal Fluid Differentiates Synucleinopathies (Parkinson Disease, Dementia With Lewy Bodies, Multiple System Atrophy) From Alzheimer Disease," Alzheimer Dis Assoc Disord., vol. 26:213-216 (2012).

Volpicelli-Daley, L. et al., "Exogenous alpha-Synuclein Fibrils Induce Lewy Body Pathology Leading to Synaptic Dysfunction and Neuron Death," Neuron, vol. 72, 57-71 (2011).

Wenning, G. et al., "The Movement Disorder Society Criteria for the Diagnosis of Multiple System Atrophy," The Movement Disorder Society Criteria for the Diagnosis of Multiple System Atrophy. Movement Disorders, vol. 37 (6):1131-1148 (2022).

* cited by examiner

Low dose = 2250 mg (cohort B1); high dose = 9000 mg (cohort B2).
aSyn, alpha-synuclein; CSF, cerebrospinal fluid; PD, Parkinson's disease; std, standard deviation.

COMPOSITIONS AND METHODS FOR TREATING SYNUCLEINOPATHIES

CROSS-REFERENCE TO RELATED APPLICATIONS

This application is a continuation of International Application No. PCT/EP2022/076402, filed Sep. 13, 2022, which claims priority to European Application No. 21197120, filed Sep. 16, 2021. The contents of the aforementioned applications are hereby incorporated by reference.

FIELD OF THE INVENTION

The present invention relates to stable and low viscosity liquid pharmaceutical compositions comprising antibodies binding to human alpha synuclein and to methods for use of antibodies binding to human alpha synuclein for treating synucleinopathies or prodromal synucleinopathy, incl. suitable doses and/or dosing regimens. These antibodies for use in treatment of synucleinopathies or prodromal synucleinopathy may be formulated in the stable and low viscosity liquid pharmaceutical compositions of the invention.

REFERENCE TO SEQUENCE LISTING

The instant application contains a Sequence Listing which has been submitted electronically in XML format and is hereby incorporated by reference in its entirety. Said XML copy, created on Jun. 26, 2023, is named LBJ-006PCCN_SequenceListing.xml and is 57 kilobytes in size.

BACKGROUND OF THE INVENTION

Biopharmaceuticals, such as antibodies, are increasingly being employed for diagnosis and treatment of diseases. Monoclonal antibodies are attractive as active pharmaceutical ingredients (APIs) as they have high homogeneity and antigen specificity, while generally having a favorable side effect profile.

Monoclonal antibodies are larger and more complex than traditional small molecule drugs. Due to these characteristics several challenges exist in the development of pharmaceutical formulations comprising such monoclonal antibodies. For a monoclonal antibody to remain biologically active in clinical use, the pharmaceutical formulation comprising such antibody must preserve and keep intact the conformational integrity of the core sequence of the antibody's amino acids while at the same time protecting the antibody's multiple functional groups from degradation. Degradation pathways for antibodies can involve chemical instability (e.g., any process which involves modification of the antibody by bond formation or cleavage resulting in a new chemical entity) or physical instability (e.g., changes in the higher order structure of the antibody). Chemical instability can e.g. result from deamidation, racemization, hydrolysis, oxidation, beta elimination or disulfide exchange. Physical instability can e.g. result from denaturation, aggregation, precipitation or adsorption.

Synucleinopathies, refer to disorders characterized by the neural inclusion of pathologic alpha synuclein aggregates called Lewy bodies. Synucleinopathies include Parkinson's disease (PD) (including idiopathic and inherited forms of Parkinson's disease) and Diffuse Lewy Body (DLB) disease (also known as Dementia with Lewy Bodies (DLB), Lewy body variant of Alzheimer's disease (LBV), Combined Alzheimer's and Parkinson disease (CAPD), pure autonomic failure (PAF) and multiple system atrophy (MSA; e.g., Olivopontocerebellar Atrophy, Striatonigral Degeneration and Shy-Drager Syndrome).

Alpha synuclein is normally associated with synapses and is believed to play a role in regulating synaptic vesicle release and thereby affecting neural communication, plasticity, learning and memory. States of synucleinopathies have been widely shown to be associated with aggregates of alpha synuclein, however, the precise pathological species of alpha synuclein remains unknown. Various misfolded/aggregated/secreted species ranging from oligomers to fibrils, and different post-translational modifications have been associated with toxicity but there is no consensus on which is most important, if indeed there even is a single toxic species.

The antibodies disclosed in WO2017/009312 bind multiple species of alpha synuclein, including all known major species formed by alternative splicing or posttranslational modifications, such as truncations, as well as oligomeric and fibrillary forms. Such antibodies are believed to be useful in treatment and/or diagnosis of disease involving alpha synuclein, such as synucleinopathies and/or conditions involving abnormal accumulation or deposition of alpha synuclein in the central nervous system. Methods of generating the antibodies disclosed in WO2017/009312 are also disclosed in that same application, as are various functional and structural characteristics of these antibodies.

In order to utilize these monoclonal antibodies in a clinical setting, there is a need for suitable and appropriate dosage regimens for such antibodies as well as suitable and appropriate pharmaceutical formulations comprising such antibodies.

As the pathological target in synucleinopathies is misfolded and aggregated species of alpha synuclein, an efficacious dosing regimen should provide sufficient targeting of such species during treatment. In a preferred scenario, experimental confirmation of direct target engagement with these aggregated forms of alpha synuclein should be confirmed during the treatment. However, any such reliable experimental confirmation is currently not possible due to the very low abundancies of pathological alpha synuclein species in CSF and plasma of patients with synucleinopathies. This low abundancy of pathological species of alpha synuclein (aggregated and oligomeric forms) and hence lack of reliable quantification of target engagement prevents an experimentally guided dose setting based on target engagement in biological samples from patients such as plasma and CSF. Thus, there is a need for methods for determining or estimating such target engagement with aggregated forms of alpha synuclein in order to identify suitable and appropriate dosage regimens for such antibodies.

SUMMARY OF THE INVENTION

The inventors of the present invention have found a way to estimate the target engagement in CSF to aggregated species of alpha synuclein and hence establish relevant dosing regimens for specific anti-alpha synuclein antibodies. Hence it is the object of the present invention to provide dosing regimens of specific anti-alpha synuclein antibodies. The dosing regimen is based on a relevant model which enables establishing dosage regimens that will provide target engagement with pathological alpha synuclein species in CSF. Further it is also the object of the present invention to provide pharmaceutically acceptable and clinically useful liquid formulations comprising such monoclonal antibody directed to alpha synuclein.

The present invention provides a method of utilizing the monoclonal anti-alpha synuclein antibodies described herein for treating synucleinopathies or prodromal synucleinopathy. This method provides two essential elements for clinical utility of said antibodies, namely specific clinically relevant dosing regimens and suitable liquid pharmaceutical compositions comprising said antibodies which can be administered to the patient suffering from synucleinopathy or prodromal synucleinopathy.

The present invention relates to suitable dosage regimens of monoclonal antibodies directed to human alpha synuclein for use in the treatment of synucleinopathies or prodromal synucleinopathies. Further the present invention relates to a liquid pharmaceutical composition comprising monoclonal anti-alpha synuclein antibodies, which liquid formulation is characterized by being stable upon storage and having low viscosity.

The appropriate dose setting for therapeutic monoclonal antibodies is important in order to provide therapeutically active doses while maintaining patient safety, preferably the dosage regimen is also convenient for the patient to be treated.

The inventors of the present invention have found a way to provide such dosage regimens despite the current lack of reliable methods for measurements of target engagement between anti-alpha synuclein antibodies and oligomeric alpha synuclein in blood or CSF samples. Aggregated/oligomeric/fibril (used herein interchangeably) species of alpha synuclein are only present in very low amount in CSF or plasma samples and hence target engagement cannot be reliably confirmed experimentally during e.g. treatment or clinical trials. Accordingly, establishment of relevant dosing regimens of specific anti-alpha synuclein antibodies that will ensure relevant target engagement to oligomeric forms of alpha synuclein in CSF—and hence clinical efficacy—must utilize complex modelling based on in depth knowledge of specific properties of each antibody such as elaborate binding profiles of said antibodies to different alpha synuclein species and human pharmacokinetics. Hence it is an object of the present invention to provide dosing regimens of specific anti-alpha synuclein antibodies based on relevant modelling which enables establishing dosage regimens ensuring target engagement with pathological alpha synuclein species in CSF. Consequently, the dosing regimens provided herein enable clinical use of specific monoclonal antibodies directed to pathological (aggregated and oligomeric forms) forms of human alpha synuclein.

The rationale for the dosing regimens of the invention is described in the experimental section and summarized in example 1.

In one aspect the invention provides a monoclonal anti-alpha synuclein antibody for use in the treatment of synucleinopathies or prodromal synucleinopathies, wherein said use comprises administering said anti-alpha synuclein antibody intravenously to a human subject suffering from synucleinopathy or in risk of developing synucleinopathy, at a dose of more than 700 mg and less than 7000 mg, such as between 900 mg to 5000 mg, or such as between 1000 mg to 4500 mg, and wherein said monoclonal anti-alpha synuclein antibody is a full-length antibody that binds an epitope within amino acids 112-117 (SEQ ID NO:9 (ILEDMP)) of human alpha synuclein (SEQ ID NO:10).

In another aspect the invention provides a method of treating synucleinopathies or prodromal synucleinopathies, said method comprises administering a monoclonal anti-alpha synuclein antibody intravenously to a human subject in need thereof, wherein said human subject is suffering from synucleinopathy or in risk of developing synucleinopathy, at a dose of more than 700 mg and less than 7000 mg, such as between 900 mg to 5000 mg, or such as between 1000 mg to 4500 mg, wherein said monoclonal anti-alpha synuclein antibody is a full-length antibody that binds an epitope within amino acids 112-117 (SEQ ID NO:9 (ILEDMP)) of human alpha synuclein (SEQ ID NO:10).

In yet another aspect the invention provides the use of a monoclonal anti-alpha synuclein antibody for the manufacture of a medicament for the treatment of synucleinopathies or prodromal synucleinopathies, wherein said use comprises administering said anti-alpha synuclein antibody intravenously to a human subject suffering from synucleinopathy or in risk of developing synucleinopathy, at a dose of more than 700 mg and less than 7000 mg, such as between 900 mg to 5000 mg, or such as between 1000 mg to 4500 mg, and wherein said monoclonal anti-alpha synuclein antibody is a full-length antibody that binds an epitope within amino acids 112-117 (SEQ ID NO:9 (ILEDMP)) of human alpha synuclein (SEQ ID NO:10).

In one embodiment of these aspects the present invention provides suitable dosage regimens for treating synucleinopathies, such as Parkinson's disease (PD) (including idiopathic and inherited forms of Parkinson's disease), Gauchers Disease (GD), Diffuse Lewy Body Disease (DLBD), Dementia with Lewy Bodies (DLB), Lewy body variant of Alzheimer's disease (LBV), Combined Alzheimer's and Parkinson's disease, pure autonomic failure or multiple system atrophy (MSA), such as possible MSA, probable MSA, MSA type C, MSA type P, clinically established MSA or clinically probable MSA.

In another embodiment of these aspects the present invention provides suitable dosage regimens for treating prodromal synucleinopathies in a human subject in risk of developing synucleinopathy, said human subject being identifiable by exhibiting one or more clinical markers of prodromal synucleinopathies such as REM Sleep Behaviour Disorder (RBD) such as isolated RBD (iRBD), dysfunctional olfaction such as hyposmia, abnormal cognitive performance in neuropsychological testing, subtle motor dysfunction or abnormal motor performance assessed by objective testing, abnormal color vision, autonomic dysfunctions (such as constipation, urinary symptoms, erectile dysfunction, orthostatic hypotension), reduced nigrostriatal dopaminergic binding in the putamen and striatum (abnormal DAT-SPECT), Seborrhoeic dermatitis, or a genotype associated with increasing phenoconversion risk such as mutations in glucocerebrosidase (encoded by the GBA gene).

In particular embodiments the invention provides suitable dosage regimens for monoclonal antibody GM37, and its variants; GM37 Variant 1, GM37 Variant 2 and GM37 Variant 3; such antibodies, methods for their manufacture and their characteristics are all disclosed in WO2017/009312.

In particular embodiments of these aspects the monoclonal anti-alpha synuclein antibody for use according to the invention is administered every 3-5 weeks, such as about every 4 weeks or once monthly, such as every 28-30 days.

In particular embodiments of these aspects the monoclonal anti-alpha synuclein antibody for use according to the invention is administered at a dose of about 750 mg, about 1050 mg, about 1400 mg, about 1750 mg, about 2100 mg, about 2450 mg, about 2800 mg, about 3150 mg, about 3500 mg, about 3850 mg, about 4200 mg, about 4550 mg, about 4900 mg, about 5250 mg, about 5600 mg, about 5950 mg, about 6300 mg, or about 6650 mg. In a further particular embodiment, the monoclonal anti-alpha synuclein antibody for use according to the invention is administered at a dose of 1050 mg, 2100 mg or 4200 mg.

In one aspect the present invention relates to a liquid pharmaceutical composition comprising a full length IgG1 monoclonal anti-alpha synuclein antibody in a concentration of 20-230 mg/mL, such as 25-225 mg/mL, wherein said antibody comprises:

a. a Heavy Chain CDR1 having the amino acid sequence of SEQ ID NO:1;
b. a Heavy Chain CDR2 having the amino acid sequence of SEQ ID NO:34;
c. a Heavy Chain CDR3 having the amino acid sequence of SEQ ID NO:3;
d. a Light Chain CDR1 having the amino acid sequence of SEQ ID NO:4;
e. a Light Chain CDR2 having the amino acid sequence of SEQ ID NO:5; and
f. a Light Chain CDR3 having the amino acid sequence of SEQ ID NO:6;

and wherein the composition further comprises a buffering agent, a pharmaceutically acceptable tonicity agent, a pharmaceutically acceptable surfactant and wherein the pH of the composition is between 4.5 to 7.5, such as 5.0 to 7.0, such as 5.5. to 6.5, such as 6.0.

Other features and advantages of the invention that apply to these aspects and embodiment will be apparent from the following detailed description of the invention, the experimental section and from the claims.

DEFINITIONS

Figure 1:
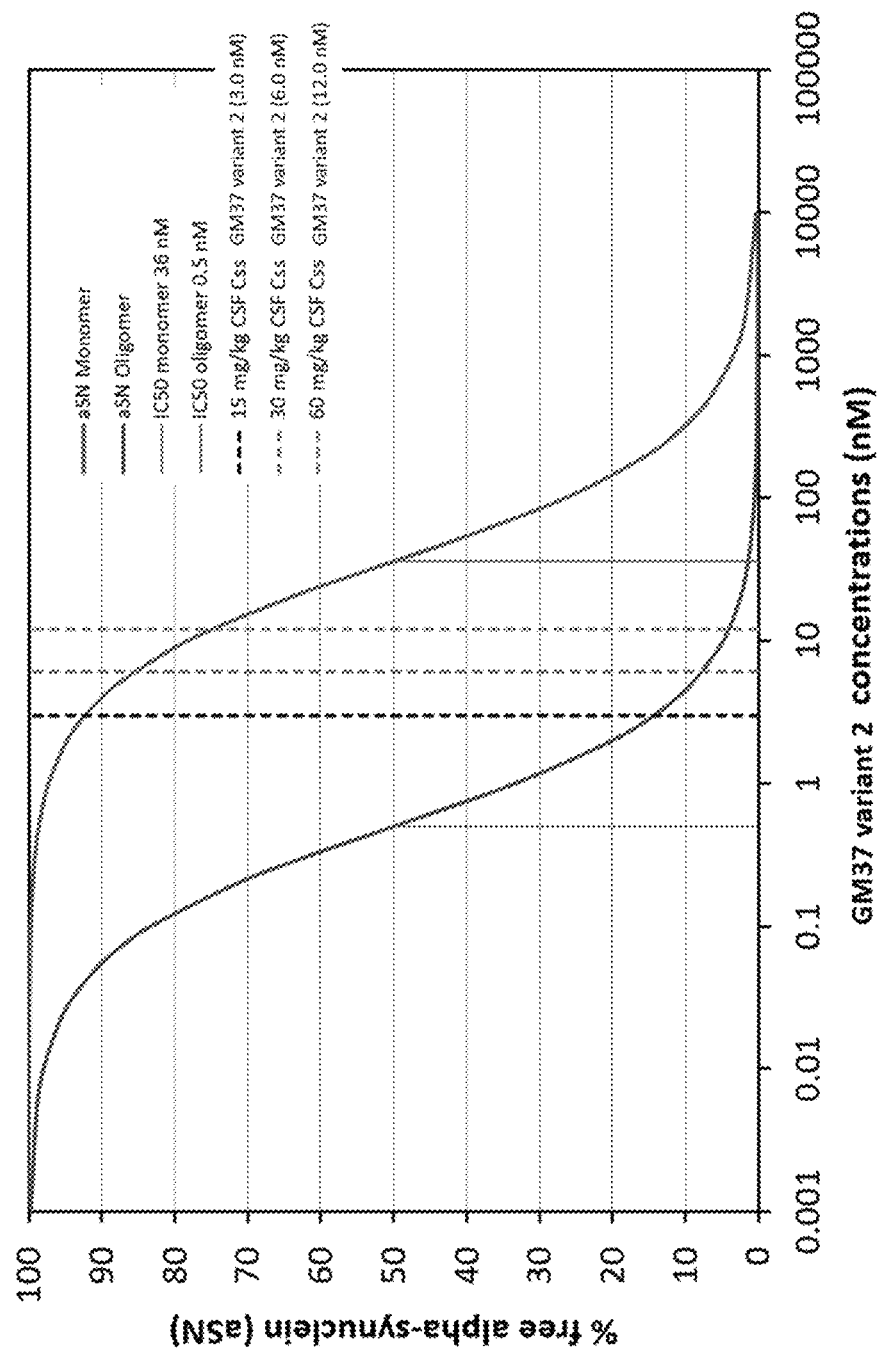
FIG. 1 shows the predicted relationship between doses of the invention and CSF exposure and % free alpha synuclein.

The term "full-length antibody" is meant to refer to an antibody format of full length (whole) antibody or substantially full-length. The term particularly refers to an antibody with heavy chains that contain an Fc region. Naturally occurring antibodies typically comprise a tetramer which is usually composed of at least two heavy (H) chains and at least two light (L) chains. Each heavy chain is comprised of a heavy chain variable domain (abbreviated herein as VH) and a heavy chain constant domain, usually comprised of three domains (CH1, CH2 and CH3). Heavy chains can for example be selected from the IgG isotype (IgG1, IgG2, IgG3 and IgG4 subtypes). Each light chain is comprised of a light chain variable domain (abbreviated herein as VL) and a light chain constant domain (CL). Light chains include kappa chains and lambda chains. The VH and VL regions can be further subdivided into regions of hypervariability, termed "complementarity determining regions," that are interspersed with regions of more conserved sequence, termed "framework regions" (FR). Each VH and VL is composed of three CDR Domains and four FR Domains arranged from amino-terminus to carboxy-terminus in the following order: FR1-CDR1-FR2-CDR2-FR3-CDR3-FR4 (or J-region). The variable domains of the heavy and light chains contain a binding domain that interacts with an antigen. In some embodiments the full-length antibody of the embodiments of the invention includes antibody variant which can be classified as "Product-related substances" according to the International Conference on Harmonization (ICH) Q6B, Product-related substances are defined as "Molecular variants of the desired product formed during manufacturer and/or storage which are active and have no deleterious effect on the safety and efficacy of the drug product. These variants possess properties comparable to the desired product and are not considered impurities." Such molecular variants of the antibodies for use according to the invention are meant to include e.g. N-Terminal Modifications such as N-terminal pyroglutamate (pyroGlu), such as truncation, or such as incomplete removal of light chain or heavy chain signal peptides, Asparagine (Asn) deamidation, Aspartate (Asp) isomerization, Succinimide, oxidation such as oxidation, cysteine related modifications such as free cysteine (Cys) residues, such as alternative disulfide bond linkage (scrambling), such as trisulfide bonding, such as the formation of thioether, or such as cysteine racemization, Glycosylation, Glycation, C-Terminal Modifications such as removal of C-terminal Lys, such as removal of both C-terminal Lys and Gly, or such as C-terminal amidation.

The term "epitope" means an antigenic determinant capable of specific binding to an antibody. Epitopes usually consist of surface groupings of molecules such as amino acids or sugar side chains and usually have specific three-dimensional structural characteristics, as well as specific charge characteristics. Conformational and linear epitopes are distinguished in that the binding to the former, but not the latter, is always lost in the presence of denaturing solvents. The epitope may comprise amino acid residues directly involved in the binding and other amino acid residues, which are not directly involved in the binding, such as amino acid residues which are effectively blocked by the specifically antigen-binding peptide (in other words, the amino acid residue is within the footprint of the specifically antigen-binding peptide). The term "112-117 epitope" or "epitope within amino acids 112-117" refers to a region of human alpha synuclein that contains at least 4 of the 6 amino acid residues of 112-117 human alpha synuclein, such as all 6 amino acid residues of 112-117 human alpha synuclein, which epitope does not include any residue from 1-111 (including any residue from 106-111) of human alpha synuclein, nor any residue from 118-140 (including residue 118-120) of human alpha synuclein. As used herein, an antibody for use according to the invention said to bind an "epitope within amino acids 112-117" is capable of specifically binding to human alpha synuclein by binding to at least 4 of the 6 amino acid residues of the 112-117 epitope, such as by binding to the 6 amino acid residues of the 112-117 epitope, without binding any residues from 1-111 (including any residue from 106-111) of human alpha synuclein, nor any residue from 118-140 (including residue 118-120) of human alpha synuclein.

The term "human antibody" (which may be abbreviated to "humAb" or "HuMab"), as used herein, is intended to include antibodies having variable and constant domains derived from human germline immunoglobulin sequences. The human antibodies of the invention may include amino acid residues not encoded by human germline immunoglobulin sequences (e.g., mutations introduced by random or site-specific mutagenesis in vitro or during gene rearrangement or by somatic mutation in vivo).

The term "humanized" refer to a molecule, generally prepared using recombinant techniques, having an antigen-binding site derived from an immunoglobulin from a non-human species and a remaining immunoglobulin structure based upon the structure and/or sequence of a human immunoglobulin. The antigen-binding site may comprise either complete non-human antibody variable domains fused to human constant domains, or only the complementarity determining regions (CDRs) of such variable domains grafted to appropriate human framework regions of human variable domains. The framework residues of such humanized molecules may be wild type (e.g., fully human) or they may be modified to contain one or more amino acid substitutions not found in the human antibody whose sequence has served as the basis for humanization. Another approach focuses not only on providing human-derived constant domains but modifying the variable domains as well so as to reshape them as closely as possible to human form. It is known that the variable domains of both heavy and light chains contain three complementarity-determining regions (CDRs) which vary in response to the antigens in question and determine binding capability, flanked by four framework regions (FRs) which are relatively conserved in a given species and which putatively provide a scaffolding for the CDRs. When nonhuman antibodies are prepared with respect to a particular antigen, the variable domains can be "reshaped" or "humanized" by grafting CDRs derived from nonhuman antibody on the FRs present in the human antibody to be modified.

In the present context, "treatment" or "treating" is intended to indicate the clinically relevant management and care of a patient for the purpose of alleviating, arresting, partly arresting, removing, delaying or slowing progression of one or more of the clinical manifestations of the disease. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of the progression a disease or disorder state, amelioration or palliation of a disease or disorder state, or remission of a disease or disorder, whether partial or total. In a particular embodiment the "treatment" or "treatment effect" consists of delaying or slowing disease progression in a patient suffering from synucleinopathy, in a particular embodiment this synucleinopathy is MSA, such MSA may be selected from one or more of the MSA subtypes, such as clinically established MSA, clinically probable MSA, possible MSA, probable MSA, MSA type C or MSA type P. In another embodiment "treatment" means to delay the disease onset in a patient with prodromal synucleinopathy. The treatment can be measured by quantifying clinical efficacy or treatment effect by measuring slowing or delay in disease progression, as assessed by longitudinal changes from baseline in the Unified Multiple System Atrophy Rating Scale (UMSARS) Part I and Part II Total score (UMSARS TS) or in the modified UMSARS Part I (mUMSARS) or in the abbreviated UMSARS (aUMSARS) up to End-of-Treatment (EoT), i.e. at the end of the treatment period of 24 weeks, 48 weeks, 72 weeks, 96 weeks or more. The treatment can also be measured by quantifying clinical efficacy or treatment effect by measuring slowing or delay in disease progression, as assessed by longitudinal changes from baseline in the UMSARS Part I, modified UMSARS Part I (mUMSARS) and/or UMSARS Part II scores up to EoT. Such disease progression could also be assessed as the change from baseline up to EoT in UMSARS TS, UMSARS Part I, mUMSARS and/or UMSARS Part II scores. The disease progression can also be assessed by longitudinal changes from baseline in the abbreviated UMSARS (aUMSARS) up to EoT or as change from baseline in Brain Volume, as Measured by Volumetric MRI (vMRI) or as change from baseline in Neurofilament Light Chain (NfL) blood concentrations. The treatment can also be measured by quantifying clinical efficacy or treatment effect by measuring slowing or delay in disease progression, as assessed by longitudinal changes from baseline in one or more parameter selected from: Schwab and England Activities of Daily Living (SE-ADL) Score; as change from baseline in Clinical Global Impression—Severity of Illness (CGI-S) Score; as change from baseline in Patient Global Impression—Severity of Illness (PGI-S) Score; as change from baseline in Observer-Reported Global Impression—Severity of Illness (OGI-S)

Score; as change from baseline in Composite Autonomic Symptom Score Select Change (COMPASS Select Change) Score; as change from baseline in UMSARS Part IV Score; as change from baseline in Speech, Swallowing, Falls, and Walking, as assessed by the UMSARS Part I Item Scores; as change from baseline in Frequency, Cause, and Consequence of Falls, as assessed by the Fall Diary Periods; as change from baseline in EuroQoI 5-Dimension, 5-Level (EQ-5D-5L) Score; as change from baseline in Brain Volume, as Measured by Volumetric MRI (vMRI); as change from baseline in Tissue Integrity, as Measured by Diffusion-Tensor Imaging (DTI) MRI; as change from baseline in Neurofilament Light Chain (NfL) blood concentrations; as change from baseline in heart rate, blood pressure, and orthostatic symptoms, as assessed in UMSARS Part III; as change from baseline in gait parameters or frequency of falls, as assessed by digital wearable sensor-based devices that are capable of tracking relevant gait parameters and/or registering falls; as change from baseline in cerebral blood flow, as measured by arterial spin labelling (ASL) MRI; as change from baseline in t-tau and NfL CSF concentrations; or as change from baseline in pathological species of α-synuclein in CSF. The patient to be treated can be identified or diagnosed via any acknowledged method or criteria in the relevant field.

The term "kd" ($sec^{-1}$ or 1/s), as used herein, refers to the dissociation rate constant of a particular antibody-antigen interaction. Said value is also referred to as the koff value.

The term "ka" ($M^{-1} \times sec^{-1}$ or 1/Msec), as used herein, refers to the association rate constant of a particular antibody-antigen interaction.

The term "KD" (M), as used herein, refers to the dissociation equilibrium constant of a particular antibody-antigen interaction and is obtained by dividing the kd by the ka. KD may be determined by methods, as described in example 6A, or other methods known in the art.

The term "KA" ($M^{-1}$ or 1/M), as used herein, refers to the association equilibrium constant of a particular antibody-antigen interaction and is obtained by dividing the ka by the kd.

The term "IC50", as used herein, refers to the antibody concentration at which 50% of the maximum inhibitory effect is reached. The exact IC50 value, usually in nM is depending on the specific assay and therefore not directly comparable between different assays.

The term "Emax", as used herein, refers to the maximal effect of the antibody at high antibody concentrations, i.e. when all alpha synuclein is bound by the antibody.

The term "avidity", as used herein, refers to the accumulated strength of an antibody-antigen complex. Here this covers two affinities of individual non-covalent binding interactions between an IgG molecule and its antigen.

The term "Cmax" as used herein, refers to the maximal concentration of an antibody as measured in plasma of a subject following infusion of said antibody.

The term "tmax" as used herein, refers to the time it takes to reach Cmax following infusion of an antibody.

The phrase "use according to the invention" as used throughout this disclosure is meant to apply to all uses and methods of the invention, including use in the treatment of synucleinopathies or prodromal synucleinopathies, methods of treating synucleinopathies or prodromal synucleinopathies, and use of a monoclonal anti-alpha synuclein antibody of the invention for the manufacture of a medicament for the treatment of synucleinopathies or prodromal synucleinopathies. Such use may include administering the monoclonal anti-alpha synuclein antibody of the invention to a patient in need thereof using suitable doses, dosing regimens and/or in a suitable pharmaceutical formulation. Such formulations or compositions are also provided by the present invention.

The terms "formulation" and "composition" are used interchangeably throughout this application.

The term "stable compositions" are meant to refer to a composition which can be stored for a specific amount of time, here at least 6 months or more, at specific conditions, here at normal storage conditions for antibody formulations, such as storage at about 5° C., wherein the protein in the composition essentially retains its physical stability and/or chemical stability and/or biological activity. Various analytical techniques for measuring protein stability are available and well known in the art, some of these are also described in the experimental section herein. Stability can be measured at a selected temperature for a selected time period. In certain embodiments, the formulation is stable at about 40° C. for at least about 1, 2, 3, 4, 5, 6, 7, 14, 21, 28, or more days. In certain embodiments, the formulation is stable at about 40° C.±3° C. for at least about 1, 2, 3, 4, 5, 6, 7, 8, or more weeks. In certain embodiments, the formulation is stable at about 25° C. for at least 1, 2, 3, 4, 5, 6, 7, 8, 9, 10, 11, 12, 13, 14, 15, 16, 17, 18, 19, 20, 21, 22, 23, 24, or more months. In certain embodiments, the formulation is stable at about 5° C.±3° C. for at least 1, 2, 3, 4, 5, 6, 7, 8, 9, 10, 11, 12, 13, 14, 15, 16, 17, 18, 19, 20, 21, 22, 23, 24, or more months. In certain embodiments, the formulation is stable at about −20° C.±3° C. for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more months. Furthermore, the formulation is preferably stable following freezing (to, e.g., −20° C., −40° C. or −70° C.) and thawing of the formulation, for example following 1, 2 3, 4, or 5 cycles of freezing and thawing. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may involve any one or more of: aggregation, deamidation (e.g. Asn deamidation), oxidation (e.g. Met oxidation), isomerization (e.g. Asp isomerization), clipping/hydrolysis/fragmentation (e.g. hinge region fragmentation), succinimide formation, unpaired cysteine(s), N-terminal extension, C-terminal processing, glycosylation differences, etc.

A "low viscosity composition" is meant to describe a liquid pharmaceutical composition having a viscosity at least below about 20 cP, such as below 15 cP, such as below 14 cP, such as below 13 cP, such as below 12 cP, such as below 11 cP, such as below 10 cP, such as below 9 cP, such as below 8 cP, such as below 7 cP, such as below 6 cP, such as below 5 cP.

In the present application a "buffering agent" refers to a buffered solution that resists changes in pH by the action of its acid-base conjugate components. The buffers or buffering agents (used interchangeably) of this invention preferably maintains a pH of the composition in the range from about 4.5 to about 7.5, such as from about 5.5 to about 6.5, for example from 5.7 to 6.4, 5.8 to 6.3 or 5.9 to 6.2. In one embodiment the buffer has a pH of 5.5, 5.6, 5.7, 5.8, 5.9, 6.0, 6.1, 6.2, 6.3, 6.4, 6.5 or 7.0. Histidine buffers (such as L-histidine) are example of buffers that will control the pH in this range. Examples of buffering agents are Acetate, Citrate, Tartrate, Histidine (such as L-Histidine), Glutamate, Phosphate, Tris, Glycine, Bicarbonate, Succinate, Sulfate and Nitrate buffers or a mixture thereof. In some embodiments the buffering agent is selected from sodium phosphate, histidine (such as L-histidine), citric acid, sodium citrate, sodium acetate or a mixture thereof. In one specific embodiment, the buffering agent is a Histidine buffer (such as L-Histidine) or a mixture of Histidine buffers.

In the present application "surfactant" refers to a surface-active agent, preferably a non-ionic surfactant. Examples of surfactants herein include polysorbate (for example, polysorbate 20 and, polysorbate 80); poloxamer (e.g. poloxamer 188); Triton; Triton X-100; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyldimethylamine; sodium methyl cocoyl-, or disodium methyl oleyl-taurate; polyethyl glycol, polypropyl glycol, and copolymers of ethylene and propylene glycol. In one specific embodiment, the pharmaceutically acceptable surfactant is polysorbate 80 also known as Tween 80.

In the present application "tonicity agent" refers to an excipient which enables an isotonic liquid pharmaceutical composition. Isotonic means that the formulation of interest has essentially the same osmotic pressure as human blood. Isotonic formulations will generally have an osmotic pressure from about 250 to 350 mOsm. Examples of tonicity agents include Mannitol, Sorbitol, Lactose, Dextrose, Trehalose, Sodium Chloride, Potassium Chloride, Glycerol and Glycerine. In one specific embodiment, the tonicity agent is a suitable salt such as NaCl.

In the present context a "bulking agent" is meant to refer to an excipient which provides additional stability to the liquid pharmaceutical composition. Examples of bulking agent include these main classes of excipients: Sugars and polyols (such as Sucrose, Trehalose, Glucose, Lactose, Sorbitol, Mannitol and Glycerol); Amino Acids (such as Arginine, Aspartic Acid, Glutamic acid, Lysine, Glycine, Glutamate, Histidine, Methionine or Alanine); and Polymers and proteins (such as Gelatin, PVP, PLGA, PEG, dextran, cyclodextrin and derivatives, starch derivatives, HSA or BSA). In one specific embodiment, the bulking agent is sucrose.

The term "Histidine buffer" or "Histidine" is meant to cover Histidine buffers and mixtures thereof such as Histidine, L-Histidine, L-Histidine hydrochloride, L-Histidine monohydrochloride, L-Histidine monohydrate and L-Histidine hydrochloride monohydrate or mixtures thereof. In one specific embodiment, the histidine buffer is a mixture of L-Histidine and L-Histidine monohydrochloride.

DETAILED DESCRIPTION OF THE INVENTION

The present invention relates to suitable dosage regimens and also provides suitable liquid pharmaceutical compositions of monoclonal antibodies directed to human alpha synuclein for use in the treatment of synucleinopathies or prodromal synucleinopathies.

In one aspect the invention provides a monoclonal anti-alpha synuclein antibody for use in the treatment of synucleinopathies or prodromal synucleinopathies, wherein said use comprises administering said anti-alpha synuclein antibody intravenously to a human subject suffering from synucleinopathy or in risk of developing synucleinopathy, at a dose of more than 700 mg and less than 7000 mg, such as between 900 mg to 5000 mg, or such as between 1000 mg to 4500 mg, and wherein said monoclonal anti-alpha synuclein antibody is a full-length antibody that binds an epitope within amino acids 112-117 (SEQ ID NO:9 (ILEDMP)) of human alpha synuclein (SEQ ID NO:10).

In another aspect the invention provides a method of treating synucleinopathies or prodromal synucleinopathies, said method comprises administering a monoclonal anti-alpha synuclein antibody intravenously to a human subject in need thereof, wherein said human subject is suffering from synucleinopathy or in risk of developing synucleinopathy, at a dose of more than 700 mg and less than 7000 mg, such as between 900 mg to 5000 mg, or such as between 1000 mg to 4500 mg, wherein said monoclonal anti-alpha synuclein antibody is a full-length antibody that binds an epitope within amino acids 112-117 (SEQ ID NO:9 (ILEDMP)) of human alpha synuclein (SEQ ID NO:10).

In yet another aspect the invention provides the use of a monoclonal anti-alpha synuclein antibody for the manufacture of a medicament for the treatment of synucleinopathies or prodromal synucleinopathies, wherein said use comprises administering said anti-alpha synuclein antibody intravenously to a human subject suffering from synucleinopathy or in risk of developing synucleinopathy, at a dose of more than 700 mg and less than 7000 mg, such as between 900 mg to 5000 mg, or such as between 1000 mg to 4500 mg, and wherein said monoclonal anti-alpha synuclein antibody is a full-length antibody that binds an epitope within amino acids 112-117 (SEQ ID NO:9 (ILEDMP)) of human alpha synuclein (SEQ ID NO:10).

In certain embodiments the monoclonal anti-alpha synuclein antibody has an estimated KD value of binding to the oligomeric form of alpha synuclein of about 0.1-1.0 nM, such as 0.2-0.8 nM, such as 0.4-0.6 nM, such as about 0.5 nM.

In certain embodiments the monoclonal anti-alpha synuclein antibody has a KD value of binding to the monomeric form of alpha synuclein of about 30-40 nM, such as 32-38 nM, such as 34-37 nM, such as about 36 nM, and an estimated binding to the oligomeric form of alpha synuclein of about 0.1-1.0 nM, such as 0.2-0.8 nM, such as 0.4-0.6 nM, such as about 0.5 nM. In one embodiment, the ratio between the monomeric and oligomeric binding values is approximately 60-70 fold enhanced to the oligomeric form as compared to the monomeric form, such as 62-68 fold enhancement, such as 64-66 fold enhancement, such as 65 fold enhancement, such enhancement in binding between the two forms is further explained in the experimental section and denoted "avidity gain". Such enhancement of binding between the two forms will be denoted avidity-gain in this disclosure. In certain embodiments the monoclonal anti-alpha synuclein antibody has a human T ½ of about 25-35 days, such as about 4 weeks, such as about 27-33 days, such as about 28 days, such as about 28-32 days, such as 30 days, such as 28-30 days.

In an embodiment, the monoclonal anti-alpha synuclein antibody for use according to the invention comprises:
 a. a Heavy Chain CDR1 having the amino acid sequence of SEQ ID NO:1;

b. a Heavy Chain CDR2 having the amino acid sequence of SEQ ID NO:2;
c. a Heavy Chain CDR3 having the amino acid sequence of SEQ ID NO:3;
d. a Light Chain CDR1 having the amino acid sequence of SEQ ID NO:4;
e. a Light Chain CDR2 having the amino acid sequence of SEQ ID NO:5; and
f. a Light Chain CDR3 having the amino acid sequence of SEQ ID NO:6.

In a particular embodiment the monoclonal anti-alpha synuclein antibody for use according to the invention comprises a heavy chain consisting of a variable domain of SEQ ID NO:7 and a light chain consisting of a variable domain of SEQ ID NO:8.

In an embodiment, the monoclonal anti-alpha synuclein antibody for use according to the invention comprises:
a. a Heavy Chain CDR1 having the amino acid sequence of SEQ ID NO:1;
b. a Heavy Chain CDR2 having the amino acid sequence of SEQ ID NO:33;
c. a Heavy Chain CDR3 having the amino acid sequence of SEQ ID NO:3;
d. a Light Chain CDR1 having the amino acid sequence of SEQ ID NO:4;
e. a Light Chain CDR2 having the amino acid sequence of SEQ ID NO:5; and
f. a Light Chain CDR3 having the amino acid sequence of SEQ ID NO:6.

In a particular embodiment the monoclonal anti-alpha synuclein antibody for use according to the invention comprises a heavy chain consisting of a variable domain of SEQ ID NO:30 and a light chain consisting of a variable domain of SEQ ID NO:8.

In an embodiment, the monoclonal anti-alpha synuclein antibody for use according to the invention comprises:
a. a Heavy Chain CDR1 having the amino acid sequence of SEQ ID NO:1;
b. a Heavy Chain CDR2 having the amino acid sequence of SEQ ID NO:34;
c. a Heavy Chain CDR3 having the amino acid sequence of SEQ ID NO:3;
d. a Light Chain CDR1 having the amino acid sequence of SEQ ID NO:4;
e. a Light Chain CDR2 having the amino acid sequence of SEQ ID NO:5; and
f. a Light Chain CDR3 having the amino acid sequence of SEQ ID NO:6.

In a particular embodiment the monoclonal anti-alpha synuclein antibody for use according to the invention comprises a heavy chain consisting of a variable domain of SEQ ID NO:31 and a light chain consisting of a variable domain of SEQ ID NO:8.

In an embodiment, the monoclonal anti-alpha synuclein antibody for use according to the invention comprises:
a. a Heavy Chain CDR1 having the amino acid sequence of SEQ ID NO:1;
b. a Heavy Chain CDR2 having the amino acid sequence of SEQ ID NO:35;
c. a Heavy Chain CDR3 having the amino acid sequence of SEQ ID NO:3;
d. a Light Chain CDR1 having the amino acid sequence of SEQ ID NO:4;
e. a Light Chain CDR2 having the amino acid sequence of SEQ ID NO:5; and
f. a Light Chain CDR3 having the amino acid sequence of SEQ ID NO:6.

In a particular embodiment the monoclonal anti-alpha synuclein antibody for use according to the invention comprises a heavy chain consisting of a variable domain of SEQ ID NO:32 and a light chain consisting of a variable domain of SEQ ID NO:8.

In a particular embodiment the monoclonal anti-alpha synuclein antibody for use according to the invention antibody is a full-length human antibody. In such embodiment the monoclonal anti-alpha synuclein antibody can e.g. be a human IgG1 antibody.

In a particular embodiment the monoclonal anti-alpha synuclein antibody for use according to the invention antibody comprises a human IgG1 heavy chain constant region and/or a human kappa light chain constant region.

In a particular embodiment the monoclonal anti-alpha synuclein antibody for use according to the invention comprises a constant heavy chain domain as defined in SEQ ID NO:18 and/or a kappa light chain constant domain as defined in SEQ ID NO:17.

In a particular embodiment the monoclonal anti-alpha synuclein antibody for use according to the invention is antibody GM37, or its variants; GM37 Variant 1, GM37 Variant 2 or GM37 Variant 3. In a preferred embodiment the antibody is GM37v2.

In one embodiment the monoclonal anti-alpha synuclein antibody for use according to the invention is administered at a dose of more than 700 mg and less than 7000 mg, such as between 900 mg to 5000 mg, or such as between 1000 mg to 4500 mg. In a specific embodiment the monoclonal anti-alpha synuclein antibody is administered at an interval of 3-5 weeks, or said antibody is administered to the human subject in another regime that provides substantially the same area under the curve (AUC) for the exposure of said antibody, or substantially the same estimated target engagement of oligomeric alpha synuclein in CSF of the patient.

In some embodiments the monoclonal anti-alpha synuclein antibody for use according to the invention is administered every 6 weeks, every 5 weeks, every 4 weeks, every 3 weeks, every 2 weeks, or every week. In some embodiments the monoclonal anti-alpha synuclein antibody for use according to the invention is administered every 20 days, every 21 days, every 22 days, every 23 days, every 24 days, every 25 days, every 26 days, every 27 days, every 28 days, every 29 days, every 30 days, every 31 days, every 32 days, every 33 days, every 34 days, every 35 days, every 36 days, every 37 days, every 38 days, every 39 days, or every 40 days.

In a particular embodiment the monoclonal anti-alpha synuclein antibody for use according to the invention is administered every 3-5 weeks, such as every 4 weeks or once monthly, such as every 25-31 days, such as every 28-30 days.

In a particular embodiment the monoclonal anti-alpha synuclein antibody for use according to the invention is administered at a dose of about 75 mg, about 225 mg, about 750 mg, about 2250 mg, about 4500 mg or about 9000 mg.

In a particular embodiment the monoclonal anti-alpha synuclein antibody for use according to the invention is administered at a dose of 1000 mg to 4500 mg, such as between 2000 mg to 4500 mg, or between 3500 mg to 4500 mg, such as 4200 mg.

In a particular embodiment the monoclonal anti-alpha synuclein antibody for use according to the invention is administered at a dose of about 750 mg, about 1050 mg, about 1400 mg, about 1750 mg, about 2100 mg, about 2450 mg, about 2800 mg, about 3150 mg, about 3500 mg, about 3850 mg, about 4200 mg, about 4550 mg, about 4900 mg, about 5250 mg, about 5600 mg, about 5950 mg, about 6300 mg, or about 6650 mg. In a further particular embodiment, the monoclonal anti-alpha synuclein antibody for use according to the invention is administered at a dose of 1050 mg, 2100 mg or 4200 mg.

In a particular embodiment the monoclonal anti-alpha synuclein antibody for use according to the invention is administered at a dose as specified above by intravenous infusion over 30 minutes ±10 minutes, such as over 20 minutes, 25 minutes, 30 minutes, 35 minutes or 40 minutes.

In a particular embodiment the monoclonal anti-alpha synuclein antibody for use according to the invention is administered at a dose as specified above by intravenous infusion over 15 minutes ±5 minutes, such as over 10 minutes, 15 minutes or 20 minutes.

In a particular embodiment the monoclonal anti-alpha synuclein antibody for use according to the invention is administered at a dose as specified above by intravenous infusion a speed of about 30 mg/min to about 150 mg/min, such as about 35 mg/min, about 70 mg/min or about 140 mg/min.

In a particular embodiment the monoclonal anti-alpha synuclein antibody for use according to the invention is administered at a dose as specified above by intravenous infusion a speed of about 25 mg/min to about 300 mg/min, such as 60 mg/min to about 300 mg/min, such as about 70 mg/min, about 140 mg/min or about 280 mg/min.

In an embodiment the monoclonal anti-alpha synuclein antibody for use according to the invention is administered in an amount and a frequency sufficient to achieve an estimated CSF mean steady state concentration of said antibody of at least 0.5 nM, such as at least 1 nM, such as at least 2 nM, such as at least 3 nM, such as at least 4 nM, such as at least 5 nM, such as at least 6 nM, such as at least 7 nM, such as at least 8 nM, such as at least 9 nM, such as at least 10 nM, such as at least 11 nM, such as at least 12 nM, such as at least 13 nM, such as at least 14 nM, or such as at least 15 nM.

In another embodiment the monoclonal anti-alpha synuclein antibody for use according to the invention is administered in an amount and a frequency sufficient to achieve an estimated target engagement to oligomeric forms of alpha synuclein in CSF of at least 50%, such as at least 55%, such as at least 60%, such as at least 75%, such as at least 77%, such as at least 80%, such as at least 82%, such as at least 85%, such as at least 87%, such as at least 90%, such as at least 92%, such as at least 95%, such as at least 97% or such as at least 99%.

In another embodiment the monoclonal anti-alpha synuclein antibody for use according to the invention, is for use in the treatment of synucleinopathies. Such synucleinopathies may be selected from the group comprising: Parkinson's disease (PD) (including idiopathic and inherited forms of Parkinson's disease), Gauchers Disease (GD), Diffuse Lewy Body Disease (DLBD), Dementia with Lewy Bodies (DLB), Lewy body variant of Alzheimer's disease (LBV), Combined Alzheimer's and Parkinson's disease, pure autonomic failure and multiple system atrophy (MSA). Such treatment may consist of slowing or delaying disease progression of the synucleinopathy (such as the MSA progression) or delaying disease onset if the patient has prodromal synucleinopathy.

In a particular embodiment the synucleinopathy to be treated is Parkinson's disease (PD).

In yet another particular embodiment the synucleinopathy to be treated is Dementia with Lewy Bodies (DLB).

In yet another particular embodiment, the synucleinopathy to be treated is multiple system atrophy (MSA). In such embodiment the human subject suffering from MSA is identifiable by having been diagnosed with MSA of the multiple system atrophy parkinsonian type (MSA-P) or multiple system atrophy cerebellar type (MSA-C) subtype or having been diagnosed with possible or probable MSA, such possible or probable MSA may also be of the multiple system atrophy parkinsonian type (MSA-P) or multiple system atrophy cerebellar type (MSA-C) subtype or having been diagnosed with clinically established MSA or clinically probable MSA, which may also be of the multiple system atrophy parkinsonian type (MSA-P) or multiple system atrophy cerebellar type (MSA-C) subtype. In yet another embodiment the MSA diagnosis is based on the presence of one or more suitable biomarkers for MSA identified in said human subject. Such biomarkers may be selected from the group comprising: physiologic biomarkers, biologic biomarkers, genetic biomarkers, molecular biomarkers, histologic biomarkers, radiographic biomarkers, imaging biomarkers, behavioral biomarkers or digital biomarkers. In further such embodiment the human subject suffering from MSA or having been diagnosed with possible or probable multiple system atrophy (MSA) or other MSA subtypes may be identifiable by validated clinical assesment and/or diagnostic methods which are known in the art. In another such embodiment, the human subject suffering from MSA or having been diagnosed with possible or probable multiple system atrophy (MSA) or other MSA subtypes may be identifiable by having had onset of motor and/or autonomic (orthostatic or urinary) MSA symptoms within the last 5 years, such as within the last 4 years, or such as within the last 3 years, or such as within the last 2 years, such as within the last year or such as within the last 6 months. In yet another such embodiment, the human subject suffering from MSA or having been diagnosed with possible or probable multiple system atrophy (MSA) or other MSA subtypes may be identifiable by having an UMSARS Part I score <16 (when omitting item 11 on sexual function). In yet another such embodiment the human subject suffering from MSA or having been diagnosed with possible or probable multiple system atrophy (MSA) or other MSA subtypes may be identifiable by having a cognitive performance evaluated by the Montreal Cognitive Assessment (MoCA) with a score >22.

In another embodiment the monoclonal anti-alpha synuclein antibody for use according to the invention, is for use in the treatment of prodromal synucleinopathies in a human subject in risk of developing synucleinopathy, said human subject being identifiable by exhibiting one or more clinical markers of prodromal synucleinopathies selected from the group comprising: REM Sleep Behaviour Disorder (RBD) such as isolated RBD (iRBD), dysfunctional olfaction such as hyposmia, abnormal cognitive performance in neuropsychological testing, subtle motor dysfunction or abnormal motor performance assessed by objective testing, abnormal color vision, autonomic dysfunctions (such as constipation, urinary symptoms, erectile dysfunction, orthostatic hypotension), reduced nigrostriatal dopaminergic binding in the putamen and striatum (abnormal DAT-SPECT), and a genotype associated with increasing phenoconversion risk such as mutations in glucocerebrosidase (encoded by the GBA gene). In such embodiment the human subject in risk of developing synucleinopathy, may be identifiable by exhibiting RBD such as isolated RBD (iRBD), and at least one additional clinical marker of prodromal synucleinopathies, such as hyposmia and/or abnormal DAT- SPECT. In yet another such embodiment the human subject in risk of developing synucleinopathy, may be identifiable by exhibiting RBD, such as isolated RBD (iRBD), and hyposmia and abnormal DAT-SPECT.

In an aspect of the invention the monoclonal anti-alpha synuclein antibody, such as GM37v2, is formulated in one of the specific liquid pharmaceutical compositions as provided in the present application and in the claims.

In another aspect of the invention is provided a kit comprising the monoclonal anti-alpha synuclein antibody for use according to the invention.

In yet another embodiment the monoclonal anti-alpha synuclein antibody for use according to the invention, is expressed in or obtained by expression in CHO cells.

In an aspect the monoclonal anti-alpha synuclein antibody for use according to the invention, is for use in treating abnormal aggregation of alpha synuclein in a human subject, wherein said human subject has been identified as having abnormal aggregation of alpha synuclein in CNS.

In some embodiments of the treatment with the monoclonal anti-alpha synuclein antibody for use according to the invention can continue for weeks, months, a year, or even several years. In further embodiments the treatment can be part of a combination therapy in which the monoclonal antibody for use according to the invention is given in combination with or adjunctive to one or more additional pharmaceutical agents. Such additional pharmaceutical agents may be part of the standard of care utilized in the specific synucleinopathy. In MSA such standard of care may for example include one or more of the following medicaments: medications to reduce Parkinson's disease-like signs and symptoms, such as levodopa and/or carbidopa, or medicaments know to be useful in treating autonomic symptoms (such as urinary symptoms or neurogenetic orthostatic hypotension), such medicaments may be selected from pyridostigmine, midodrine or droxidopa.

Specific Doses and Dosage Regimens

Doses and dosage regimens of the invention may be expressed in fixed doses such as a specific amount of mg of a monoclonal antibody for use according to the invention (i.e., independent of the body weight of the human subject to be treated). Such doses are described in the embodiments and aspects of the present invention including Table 1 below. In some embodiments, doses or dosage regimens of the invention may also be expressed in mg/kg (i.e., a dose which varies based on the body weight of the human subject to be treated). It will be within the skills of a trained physician to convert between fixed doses and doses administered according to body weight (such as mg/kg). The result of the conversion will depend on the body weight of the human subject to be treated with doses or dosage regimens of the invention.

In one embodiment the monoclonal anti-alpha synuclein antibody for use according to the invention is administered at a dose of between 1000 mg to 4500 mg at an interval of 3-5 weeks, or said antibody is administered to the human subject in another regime that provides substantially the same estimated target engagement of oligomeric alpha synuclein in CSF of the patient. In a particular embodiment said antibody is administered to the human subject in a regime that provides substantially the same estimated target engagement of oligomeric alpha synuclein in CSF of the patient as 4200 mg GM37v2 dosed about every 4 weeks.

In some embodiments the monoclonal anti-alpha synuclein antibody for use according to the invention is administered every 4 weeks. In some embodiments the monoclonal anti-alpha synuclein antibody for use according to the invention is administered every month. In some embodiments the monoclonal anti-alpha synuclein antibody for use according to the invention is administered every 27 days, every 28 days, every 29 days, every 30 days, or every 31 days.

In a particular embodiment the monoclonal anti-alpha synuclein antibody for use according to the invention is administered every 3-5 weeks, such as every 4 weeks or once monthly, such as every 28-30 days.

In a particular embodiment the monoclonal anti-alpha synuclein antibody for use according to the invention is administered at a dose of 1000 mg to 4500 mg, such as between 2000 mg to 4500 mg, or between 3500 mg to 4500 mg, such as 4200 mg.

In a particular embodiment the monoclonal anti-alpha synuclein antibody for use according to the invention is administered at a dose of about 1050 mg, about 1400 mg, about 1750 mg, about 2100 mg, about 2450 mg, about 2800 mg, about 3150 mg, about 3500 mg, about 3850 mg, about 4200 mg. In a further particular embodiment, the monoclonal anti-alpha synuclein antibody for use according to the invention is administered at a dose of 1050 mg, 2100 mg or 4200 mg.

In one embodiment the monoclonal anti-alpha synuclein antibody for use according to the invention is administered at a dose of between 13 mg/kg to 71 mg/kg, or such as between 14 mg/kg to 64 mg/kg, or such as between 15 mg/kg to 60 mg/kg, or such as 15 mg/kg, or such as 30 mg/kg, or such as 60 mg/kg at an interval of 3-5 weeks, or said antibody is administered to the human subject in another regime that provides substantially the same estimated target engagement of oligomeric alpha synuclein in CSF of the patient. In a particular embodiment said antibody is administered to the human subject in a regime that provides substantially the same estimated target engagement of oligomeric alpha synuclein in CSF of the patient as 60 mg/kg GM37v2 dosed about every 4 weeks.

In a particular embodiment the monoclonal anti-alpha synuclein antibody for use according to the invention is administered at a dose of about 1 mg/kg, about 3 mg/kg, about 11 mg/kg, about 32 mg/kg, about 64 mg/kg or about 129 mg/kg.

In a particular embodiment the monoclonal anti-alpha synuclein antibody for use according to the invention is administered at a dose of 14 mg/kg to 64 mg/kg, such as between 15 mg/kg to 60, such as between 30 mg/kg to 60 mg/kg, such as 60 mg/kg.

In a particular embodiment the monoclonal anti-alpha synuclein antibody for use according to the invention is administered at a dose of about 11 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, or about 95 mg/kg. In a further particular embodiment, the monoclonal anti-alpha synuclein antibody for use according to the invention is administered at a dose of 15 mg/kg, 30 mg/kg or 60 mg/kg.

In a particular embodiment the patient to be treated has a body weight of between 50 to 110 kg, such as 50 kg, 55 kg, 60 kg, 65 kg, 70 kg, 75 kg, 80 kg, 85 kg, 90 kg, 95 kg, 100 kg, 105 kg or 110 kg. In the clinical study disclosed in Example 3 the average body weight of the human subjects included were about 70 kg.

In some embodiments the doses and dosage regimens of the present invention may also be expressed as the amount and the administration frequency of a monoclonal antibody of the invention, which provides sufficient estimated CSF mean steady state concentration, sufficient AUC exposure or sufficient estimated target engagement to oligomeric forms of alpha synuclein in CSF to obtain clinical efficacy.

The table below specify the conversion between the relevant dosage formats for an illustrative human subject with a body weight of 70 kg.

TABLE 1

Doses of the invention and conversion between dosage formats and estimates of target engagement in CSF and mean steady state concentrations in CSF with IV dosing intervals of about 28 days.

| Dose per kg body weight (mg/kg) | Fixed dose for patient with 70 kg body weight (mg) | Estimated CSF mean steady state concentration (nM) | Estimated target engagement to oligomeric forms of alpha synuclein in CSF (%) |
|---|---|---|---|
| 10 | 700 | * | * |
| 15 | 1050 | 3 | 85 |
| 20 | 1400 | * | * |
| 25 | 1750 | * | * |
| 30 | 2100 | 6 | 90 |
| 35 | 2450 | * | * |
| 40 | 2800 | * | * |
| 45 | 3150 | * | * |
| 50 | 3500 | * | * |
| 55 | 3850 | * | * |
| 60 | 4200 | 12 | 95 |
| 65 | 4550 | * | * |
| 70 | 4900 | * | * |
| 75 | 5250 | * | * |
| 80 | 5600 | * | * |
| 85 | 5950 | * | * |
| 90 | 6300 | * | * |
| 95 | 6650 | * | * |
| 100 | 7000 | * | * |
| 110 | 7700 | * | * |
| 120 | 8400 | * | * |
| 130 | 9100 | * | * |

* for each dose the estimated CSF mean Css and target engagement in CSF for aggregated/oligomeric alpha synuclein can be calculated as described in example 1.

Exemplary dosing regimens are provided in the table below:

| Route and frequency | Dose |
|---|---|
| IV infusion, about every 4 weeks (or monthly) | 1050 mg or 15 mg/kg |
| IV infusion, about every 4 weeks (or monthly) | 2100 mg or 30 mg/kg |
| IV infusion, about every 4 weeks (or monthly) | 4200 mg or 60 mg/kg |

For the purpose of this disclosure the CSF concentrations of antibodies for use according to the invention and the brain interstitial fluid (ISF) concentrations of said antibodies are assumed to be equal.

In one embodiment, the monoclonal antibody for use according to the invention (e.g., GM37 or variants thereof, such as GM37v2) is administered intravenously and dosed such that a desired therapeutic concentration of the antibody is achieved in CSF and/or ISF of the human subject. In one embodiment, the antibody achieves a concentration sufficient to enter the brain and produce a therapeutic effect, e.g., mediated by binding to aggregated alpha synuclein and triggering microglia-dependent and/or independent clearance/inactivation, and/or reducing α-synuclein aggregation, and/or preventing prion-like intracellular spread of α-synuclein.

In another embodiment, the desired therapeutic concentration of the monoclonal antibody for use according to the invention (e.g., GM37 or variants thereof, such as GM37v2) in CSF and/or ISF can be equal to the concentration of the antibody that is able to provide and maintain (after 1 or more doses) at least 10-100%, such as 20-90%, such as 30-80% such as 40-70%, such as 50-60%, such as at least 10%, such as at least 20%, such as at least 30%, such as at least 40%, such as at least 50%, such as at least 60%, such as at least 70%, such as at least 80%, such as at least 85%, such as at least 90%, such as at least 95% reduction of aggregated alpha synuclein in ISF and/or CSF of the subject.

In one embodiment, the dosage regimen of the invention achieves an antibody (e.g., GM37 or variants thereof, such as GM37v2) concentration which is at above the estimated IC50 in ISF and/or CSF of the subject.

In one embodiment, the dosage regimen of the invention achieves an antibody (e.g., GM37 or variants thereof, such as GM37v2) concentration which is above the estimated IC50 and below the estimated IC95 for oligomeric alpha synuclein in ISF and/or CSF of the subject.

In one embodiment, the dosage regimen of the invention achieves an antibody (e.g., GM37 or variants thereof, such as GM37v2) concentration which is above the estimated IC85 for oligomeric alpha synuclein and below the estimated IC95 in ISF and/or CSF of the subject.

In one embodiment, the dosage regimen of the invention achieves an antibody (e.g., GM37 or variants thereof, such as GM37v2) concentration which is above the estimated IC85 for oligomeric alpha synuclein in the ISF and/or CSF of the subject.

In one embodiment, the dosage regimen of the invention achieves an antibody (e.g., GM37 or variants thereof, such as GM37v2) concentration which is above the estimated IC90 for oligomeric alpha synuclein in the ISF and/or CSF of the subject.

In one embodiment, the dosage regimen of the invention achieves an antibody (e.g., GM37 or variants thereof, such as GM37v2) concentration which is above the estimated IC95 for oligomeric alpha synuclein in the ISF and/or CSF of the subject.

In another embodiment, the dosage regimen of the invention achieves an antibody concentration (e.g., GM37 or variants thereof, such as GM37v2) that is able to provide and maintain (after 1 or more doses) greater than estimated 50% reduction of aggregated α-synuclein in the ISF and/or CSF of the subject.

In another embodiment, the dosage regimen of the invention achieves an antibody concentration (e.g., GM37 or variants thereof, such as GM37v2) that is able to provide and maintain (after 1 or more doses) greater than estimated 80% reduction of aggregated α-synuclein in the ISF and/or CSF of the subject.

In another embodiment, the dosage regimen of the invention achieves an antibody concentration (e.g., GM37 or variants thereof, such as GM37v2) that is able to provide and maintain (after 1 or more doses) greater than estimated 90% reduction of aggregated α-synuclein in the ISF and/or CSF of the subject.

In another embodiment, the dosage regimen of the invention achieves an antibody concentration (e.g., GM37 or variants thereof, such as GM37v2) that is able to provide and maintain (after 1 or more doses) greater than estimated 95% reduction of aggregated α-synuclein in the ISF and/or CSF of the subject.

The dosage regimens of the invention are relevant and apply to all types of synucleinopathies and prodromal synucleinopathies. The dosage regimen is ultimately decided on the basis of the required estimated CSF mean steady state concentration needed to obtain the desired target engagement of oligomeric alpha synuclein in CSF/brain. Although it is not known exactly how much aggregated alpha synuclein must be removed from CSF/ISF to modify and/or slow disease progression, the CSF alpha synuclein load have not been found to differ significantly among different types of synucleinopathies. Tateno et al has e.g. shown that the amount of alpha synuclein in CSF is comparable between patient suffering from dementia with Lewy bodies (DLB), Parkinson disease (PD), and multiple system atrophy (MSA) (Tateno et al, Alzheimer Dis Assoc Disord 2012; 26:213-216) which indicate that the dosage regimens of the invention can be predicted to be suitable for synucleinopathies generally and is therefore not limited to a specific indication such as PD, DLB or MSA.

In addition, the dosage regimens of the invention are also relevant for patients with prodromal synucleinopathies as these patients have been shown to display signs of altered alpha synuclein processing; e.g. Mollenhauer et al. has demonstrated that among prodromal synucleinopathy groups, the hyposmic participants showed the lowest mean CSF alpha synuclein levels, whereas iRBD participants had intermediate levels between healthy controls and Parkinson's Patients (Mollenhauer et al. Mov Disord. 2019 September; 34(9): 1354-1364). These findings indicate that patients with clinical traits of prodromal synucleinopathies already have decreased CSF alpha synuclein levels and this is consistent with significant pathology being present already during these prodromal stages.

Antibodies of the Invention

The antibodies for use according to the present invention bind to an epitope within the 112-117 epitope. In one embodiment, the invention relates to monoclonal antibody GM37, its variants (e.g., GM37 Variant 1, GM37 Variant 2 and GM37 Variant 3), or GM285 for use in the treatment of synucleinopathies or prodromal synucleinopathies.

The GM37, GM37 Variant 1, GM37 Variant 2, and GM37 Variant 3 antibodies bind an epitope within amino acids 112-117 (SEQ ID NO:9 (ILEDMP)) of human alpha synuclein (SEQ ID NO:10). Specifically, the GM37, GM37 Variant 1, GM37 Variant 2, and GM37 Variant 3 antibodies bind all 6 amino acids within this epitope.

The GM285 antibody binds the epitope of amino acid 112-115 (ILED; SEQ ID NO:19) of human alpha synuclein (SEQ ID NO:10).

An "anti-alpha synuclein antibody" or "alpha synuclein antibody" (used interchangeably) is an antibody which binds to alpha synuclein or an alpha synuclein fragment. The antibodies of the present invention specifically bind within the amino acids sequence of alpha synuclein corresponding to SEQ ID NOs 9 and/or 19.

The term antibody "GM37" is intended to include an antibody comprising the Heavy Chain CDR1-3 SEQ ID Nos:1, 2 and 3 and the Light Chain CDR1-3 as given in SEQ ID Nos:4, 5 and 6. In one embodiment, the antibody GM37 may comprise the heavy chain variable domain of SEQ ID NO:7 and/or the light chain variable domain of SEQ ID NO:8. For example, the antibody GM37 may be an IgG antibody comprising a heavy chain consisting of a variable domain of SEQ ID NO:7 and a constant domain of SEQ ID NO:18 together with a light chain consisting of a variable domain of SEQ ID NO:8 and a kappa constant domain of SEQ ID NO:17.

The term antibody "GM37 variant 1" is intended to include an antibody comprising the Heavy Chain CDR1-3 SEQ ID Nos:1, 33 and 3 and the Light Chain CDR1-3 as given in SEQ ID Nos:4, 5 and 6. In one embodiment, the antibody GM37 may comprise the heavy chain variable domain of SEQ ID NO:30 and/or the light chain variable domain of SEQ ID NO:8. For example, the antibody GM37 may be an IgG1 antibody comprising a heavy chain consisting of a variable domain of SEQ ID NO:30 and a constant domain of SEQ ID NO:18 together with a light chain consisting of a variable domain of SEQ ID NO:8 and a kappa constant domain of SEQ ID NO:17.

The term antibody "GM37 variant 2" or "GM37v2" (used interchangeably) is intended to include an antibody comprising the Heavy Chain CDR1-3 SEQ ID Nos:1, 34 and 3 and the Light Chain CDR1-3 as given in SEQ ID Nos:4, 5 and 6. In one embodiment, the antibody GM37 may comprise the heavy chain variable domain of SEQ ID NO:31 and/or the light chain variable domain of SEQ ID NO:8. For example, the antibody GM37 may be an IgG1 antibody comprising a heavy chain consisting of a variable domain of SEQ ID NO:31 and a constant domain of SEQ ID NO:18 together with a light chain consisting of a variable domain of SEQ ID NO:8 and a kappa constant domain of SEQ ID NO:17.

The term antibody "GM37 variant 3" is intended to include an antibody comprising the Heavy Chain CDR1-3 SEQ ID Nos:1, 35 and 3 and the Light Chain CDR1-3 as given in SEQ ID Nos:4, 5 and 6. In one embodiment, the antibody GM37 may comprise the heavy chain variable domain of SEQ ID NO:32 and/or the light chain variable domain of SEQ ID NO:8. For example, the antibody GM37 may be an IgG1 antibody comprising a heavy chain consisting of a variable domain of SEQ ID NO:32 and a constant domain of SEQ ID NO:18 together with a light chain consisting of a variable domain of SEQ ID NO:8 and a kappa constant domain of SEQ ID NO:17.

The term antibody "GM285" is intended to include an antibody comprising the Heavy Chain CDR1-3 SEQ ID Nos:20, 21 and 22 and the Light Chain CDR1-3 as given in SEQ ID Nos:23, 24 and 25. In one embodiment, the antibody GM37 may comprise the heavy chain variable domain of SEQ ID NO:26 and/or the light chain variable domain of SEQ ID NO:27. For example, the antibody GM37 may be an IgG1 antibody comprising a heavy chain consisting of a variable domain of SEQ ID NO:26 and a constant domain of SEQ ID NO:28 together with a light chain consisting of a variable domain of SEQ ID NO:27 and a kappa constant domain of SEQ ID NO:29.

In preferred embodiments of the invention the full-length GM37, GM37 Variant 1, GM37 Variant 2, GM37 Variant 3, or GM285 antibody is an IgG isotype format, most preferred is the IgG1 format, even more preferred is a human or humanized IgG1 format.

| Table with specific amino acid sequences of the invention as used herein: | |
|---|---|
| SEQ ID NO: 1 | GM37 CDR 1 Heavy Chain |
| SEQ ID NO: 2 | GM37 CDR 2 Heavy Chain |
| SEQ ID NO: 3 | GM37 CDR 3 Heavy Chain |
| SEQ ID NO: 4 | GM37 CDR 1 Light Chain |
| SEQ ID NO: 5 | GM37 CDR 2 Light Chain |
| SEQ ID NO: 6 | GM37 CDR 3 Light Chain |
| SEQ ID NO: 7 | GM37 Heavy Chain Variable Domain |
| SEQ ID NO: 8 | GM37 Light Chain Variable Domain |
| SEQ ID NO: 9 | Epitope 112-117 of Human Alpha synuclein |
| SEQ ID NO: 10 | Human Alpha synuclein |
| SEQ ID NO: 11 | A-Syn-AAKK-BAP |
| SEQ ID NO: 12 | A-Syn-BAAK-BAP |
| SEQ ID NO: 13 | A-Syn-BBAA-BAP |
| SEQ ID NO: 14 | A-Syn-BBKK-BAP |
| SEQ ID NO: 15 | A-Syn-120-140_Del-BAP |
| SEQ ID NO: 16 | Residues 1-119 of Human Alpha synuclein |
| SEQ ID NO: 17 | Kappa Light Chain Constant domain |
| SEQ ID NO: 18 | IgG1 Heavy Chain Constant domain |
| SEQ ID NO: 19 | GM285 Epitope 112-115 |
| SEQ ID NO: 20 | GM285 CDR 1 Heavy Chain |
| SEQ ID NO: 21 | GM285 CDR 2 Heavy Chain |
| SEQ ID NO: 22 | GM285 CDR 3 Heavy Chain |
| SEQ ID NO: 23 | GM285 CDR 1 Light Chain |
| SEQ ID NO: 24 | GM285 CDR 2 Light Chain |
| SEQ ID NO: 25 | GM285 CDR 3 Light Chain |
| SEQ ID NO: 26 | GM285 Heavy Chain Variable Domain |
| SEQ ID NO: 27 | GM285 Light Chain Variable Domain |
| SEQ ID NO: 28 | GM285 IgG1 Heavy Chain Constant domain |
| SEQ ID NO: 29 | GM285 Kappa Light Chain Constant domain |
| SEQ ID NO: 30 | GM37 Variant 1 Heavy Chain Variable Domain |
| SEQ ID NO: 31 | GM37 Variant 2 Heavy Chain Variable Domain |
| SEQ ID NO: 32 | GM37 Variant 3 Heavy Chain Variable Domain |
| SEQ ID NO: 33 | GM37 Variant 1 Heavy Chain CDR 2 |
| SEQ ID NO: 34 | GM37 Variant 2 Heavy Chain CDR 2 |
| SEQ ID NO: 35 | GM37 Variant 3 Heavy Chain CDR 2 |
| SEQ ID NO: 36 | 9E4 Binding Epitope |
| SEQ ID NO: 37 | Human Beta-Synuclein |
| SEQ ID NO: 38 | Human Gamma-Synuclein |
| SEQ ID NO: 39 | Alpha synuclein Ortholog for Cynomolgus Monkey |
| SEQ ID NO: 40 | Alpha synuclein Ortholog for Rat |
| SEQ ID NO: 41 | Alpha synuclein Ortholog for Mouse |
| SEQ ID NO: 42 | 9E4 HC |
| SEQ ID NO: 43 | 9E4 LC |

```
                                                              (SEQ ID NO: 1)
GFTFSSYAMT (SEQ ID NO: 2)
AIRSN GDRTD YADSVKG (SEQ ID NO: 33)
AIRSS GDRTD YADSVKG (SEQ ID NO: 34)
AIRSQ GDRTD YADSVKG (SEQ ID NO: 35)
AIRSH GDRTD YADSVKG (SEQ ID NO: 3)
AKNWAPFDS (SEQ ID NO: 4)
ASQSVSSSYLA (SEQ ID NO: 5)
GASSRAT (SEQ ID NO: 6)
QQYGSSPWT (SEQ ID NO: 7)
EVQLLESGGG LVQTGGSLRL SCAASGFTFS SYAMTWVRQA PGKGLEWVSA

IRSNGDRTDY ADSVKGRFTI SRDNSQNTLY LQMNSLRAED TAVYYCAKNW

APFDSWGQGT LVTVSS (SEQ ID NO: 8)
EIVLTQSPGT LSLSPGERAT LSCRASQSVS SSYLAWYQQK PGQAPRLLIY

GASSRATGIP DRESGSGSGT DFTLTISRLE PEDFAVYYCQ QYGSSPWTFG QGTKVEIK
```

```
                                                   (SEQ ID NO 26)
EVQLLESGGG LVQPGGSLRL SCAASGFTFS RFTMTWVRQA PGKGLEWVSA

ISGSGGGTSY ADSVKGRLTV SRDNSKNTLY LQMNSLRAED TAVYYCAKNW

APFDYWGQGT LVTVSS.

(SEQ ID NO: 27)
EIVLTQSPGT LSLSPGERAT LSCRASQSVS RSYLAWYQQK PGQAPRLLIY

GASSRATGIP DRFSGSGSGT DFTLTVSRLE PEDFAVYYCQ QYGSSPWTFG QGTKVEIK.

(SEQ ID NO: 30)
EVQLLESGGG LVQTGGSLRL SCAASGFTES SYAMTWVRQA PGKGLEWVSA

IRSSGDRTDY ADSVKGRFTI SRDNSQNTLY LQMNSLRAED TAVYYCAKNW

APFDSWGQGT LVTVSS (SEQ ID NO: 31)
EVQLLESGGG LVQTGGSLRL SCAASGFTES SYAMTWVRQA PGKGLEWVSA

IRSQGDRTDY ADSVKGRFTI SRDNSQNTLY LQMNSLRAED TAVYYCAKNW

APFDSWGQGT LVTVSS (SEQ ID NO: 32)
EVQLLESGGG LVQTGGSLRL SCAASGFTFS SYAMTWVRQA PGKGLEWVSA

IRSHGDRTDY ADSVKGRFTI SRDNSQNTLY LQMNSLRAED TAVYYCAKNW

APFDSWGQGT LVTVSS (SEQ ID NO: 17)
RTVAAPSVFI FPPSDEQLKS GTASVVCLLN NFYPREAKVQ WKVDNALQSG NSQESVTEQD

SKDSTYSLSS TLTLSKADYE KHKVYACEVT HQGLSSPVTK SFNRGEC (SEQ ID NO: 18)
ASTKGPSVFP LAPSSKSTSG GTAALGCLVK DYFPEPVTVS WNSGALTSGV HTFPAVLQSS

GLYSLSSVVT VPSSSLGTQT YICNVNHKPS NTKVDKRVEP KSCDKTHTCP PCPAPELLGG

PSVFLFPPKP KDTLMISRTP EVTCVVVDVS HEDPEVKFNW YVDGVEVHNA KTKPREEQYN

STYRVVSVLT VLHQDWLNGK EYKCKVSNKA LPAPIEKTIS KAKGQPREPQ VYTLPPSREE

MTKNQVSLTC LVKGFYPSDI AVEWESNGQP ENNYKTTPPV LDSDGSFFLY SKLTVDKSRW

QQGNVFSCSV MHEALHNHYT QKSLSLSPG (SEQ ID NO: 20)
AASGFTFSRFTMT (SEQ ID NO: 21)
AISGSGGGTS YADSVKG (SEQ ID NO: 22)
AKNWAPFDY (SEQ ID NO: 23)
RASQSVSRSYLA (SEQ ID NO: 24)
GASSRAT (SEQ ID NO: 25)
QQYGSSPWT
```

Full Sequence List of the Invention is Given Below:
Sequence Listing Information:
  DTD Version: V1_3
  File Name: 1264-WO-PCT Seq list ST26.xml
  Software Name: WIPO Sequence
  Software Version: 2.1.1
  Production Date: 2022 Aug. 3
General Information:
  Current application/Applicant file reference: 1264-WO-PCT
  Earliest priority application/IP Office: EP
  Earliest priority application/Application number: EP21197120.5
  Earliest priority application/Filing date: Sep. 16, 2021
  Applicant name: H. Lundbeck A/S
  Applicant name/Language: da
  Invention title: COMPOSITIONS AND METHODS FOR TREATING SYNUCLEINOPATHIES (en)
  Sequence Total Quantity: 43
Sequences:
  Sequence Number (ID): 1
  Length: 10
  Molecule Type: AA
  Features Location/Qualifiers:
    REGION, 1 . . . 10
      > note, GM37 CDR 1 Heavy Chain source, 1 . . . 10
      > mol_type, protein
      > organism, synthetic construct
  Residues:

```
                GFTFSSYAMT       10
```

Sequence Number (ID): 2
  Length: 17
  Molecule Type: AA
  Features Location/Qualifiers:
    REGION, 1 . . . 17
      > note, GM37 CDR2 Heavy Chain source, 1 . . . 17
      > mol_type, protein
      > organism, synthetic construct
  Residues:

```
           AIRSNGDRTD YADSVKG      17
```

Sequence Number (ID): 3
  Length: 9
  Molecule Type: AA
  Features Location/Qualifiers:
    REGION, 1 . . . 9
      > note, GM37 CDR3 Heavy Chain source, 1 . . . 9
      > mol_type, protein
      > organism, synthetic construct
  Residues:

```
                 AKNWAPFDS        9
```

Sequence Number (ID): 4
  Length: 11
  Molecule Type: AA
  Features Location/Qualifiers:
    REGION, 1 . . . 11
      > note, GM37 CDR1 Light Chain source, 1 . . . 11
      > mol_type, protein
      > organism, synthetic construct
  Residues:

```
               ASQSVSSSYL A       11
```

Sequence Number (ID): 5
  Length: 7
  Molecule Type: AA
  Features Location/Qualifiers:
    REGION, 1 . . . 7
      > note, GM37 CDR 2 Light chain source, 1 . . . 7
      > mol_type, protein
      > organism, synthetic construct
  Residues:

```
                  GASSRAT         7
```

Sequence Number (ID): 6
  Length: 9
  Molecule Type: AA
  Features Location/Qualifiers:
    REGION, 1 . . . 9
      > note, GM37 CDR 3 Light chain source, 1 . . . 9
      > mol_type, protein
      > organism, synthetic construct
  Residues:

```
                 QQYGSSPWT        9
```

Sequence Number (ID): 7
  Length: 116
  Molecule Type: AA
  Features Location/Qualifiers:
    REGION, 1 . . . 116
      > note, GM37 CDR Heavy chain source, 1 . . . 116
      > mol_type, protein
      > organism, synthetic construct
  Residues:

```
EVQLLESGGG LVQTGGSLRL SCAASGFTFS SYAMTWVRQA PGKGLEWVSA IRSNGDRTDY   60

ADSVKGRFTI SRDNSQNTLY LQMNSLRAED TAVYYCAKNW APFDSWGQGT LVTVSS      116

LVQTGGSLRL SCAASGFTFS
```

Sequence Number (ID): 8
Length: 108
Molecule Type: AA
Features Location/Qualifiers:
    REGION, 1 . . . 108
        > note, GM 37 Light Chain
    source, 1 . . . 108
        > mol_type, protein
        > organism, synthetic construct
Residues:

EIVLTQSPGT LSLSPGERAT LSCRASQSVS SSYLAWYQQK PGQAPRLLIY GASSRATGIP    60

DRFSGSGSGT DFTLTISRLE PEDFAVYYCQ QYGSSPWTFG QGTKVEIK               108

Sequence Number (ID): 9
Length: 6
Molecule Type: AA
Features Location/Qualifiers:
    REGION, 1 . . . 6
        > note, Epitope 112-117
    source, 1 . . . 6
        > mol_type, protein
        > organism, synthetic construct Residues:

ILEDMP  6

Sequence Number (ID): 10
Length: 140
Molecule Type: AA
Features Location/Qualifiers:
    REGION, 1 . . . 140
        > note, Alpha synuclein
    source, 1 . . . 140
        > mol_type, protein
        > organism, synthetic construct
Residues

MDVFMKGLSK AKEGVVAAAE KTKQGVAEAA GKTKEGVLYV GSKTKEGVVH GVATVAEKTK    60

EQVTNVGGAV VTGVTAVAQK TVEGAGSIAA ATGFVKKDQL GKNEEGAPQE GILEDMPVDP  120

DNEAYEMPSE EGYQDYEPEA                                              140

Sequence Number (ID): 11
Length: 165
Molecule Type: AA
Features Location/Qualifiers:
    REGION, 1 . . . 165
        > note, A-Syn-AAKK-BAP
    source, 1 . . . 165
        > mol_type, protein
        > organism, synthetic construct
Residues:

MDVFMKGLSK AKEGVVAAAE KTKQGVAEAA GKTKEGVLYV GSKTKEGVVH GVATVAEKTK    60

EQVTNVGGAV VTGVTAVAQK TVEGAGNIAA ATGLVKKDQL AKQNEEGFLQ EGMVNNTDIP  120

VDPENEAYEM PPEEEYQDYE PEAGSAGGSG GLNDIFEAQK IEWHE                  165

Sequence Number (ID): 12
Length: 165
Molecule Type: AA
Features Location/Qualifiers:
  REGION, 1 ... 165
    > note, A-Syn-BAAK-BAP
  source, 1 ... 165
    > mol_type, protein
    > organism, synthetic construct
Residues:

MDVFMKGLSM AKEGVVAAAE KTKQGVTEAA EKTKEGVLYV GSKTKEGVVH GVATVAEKTK   60

EQVTNVGGAV VTGVTAVAQK TVEGAGSIAA ATGFVKKDQL AKQNEEGFLQ EGMVNNTDIP  120

VDPENEAYEM PPEEEYQDYE PEAGSAGGSG GLNDIFEAQK IEWHE                 165

Sequence Number (ID): 13
Length: 162
Molecule Type: AA
Features Location/Qualifiers:
  REGION, 1 ... 162
    > note, A-Syn-BBAA-BAP
  source, 1 ... 162
    > mol_type, protein
    > organism, synthetic construct
Residues:

MDVFMKGLSM AKEGVVAAAE KTKQGVTEAA EKTKEGVLYV GSKTREGVVQ GVASVAEKTK   60

EQASHLGGAV VTGVTAVAQK TVEGAGSIAA ATGFVKKDQL GKNEEGAPQE GILEDMPVDP  120

DNEAYEMPSE EGYQDYEPEA GSAGGSGGLN DIFEAQKIEW HE                    162

Sequence Number (ID): 14
Length: 165
Molecule Type: AA
Features Location/Qualifiers:
  REGION, 1 ... 165
    > note, A-Syn-BBKK-BAP
  source, 1 ... 165
    > mol_type, protein
    > organism, synthetic construct
Residues:

MDVFMKGLSM AKEGVVAAAE KTKQGVTEAA EKTKEGVLYV GSKTREGVVQ GVASVAEKTK   60

EQASHLGGAV VTGVTAVAQK TVEGAGNIAA ATGLVKKDQL AKQNEEGFLQ EGMVNNTDIP  120

VDPENEAYEM PPEEEYQDYE PEAGSAGGSG GLNDIFEAQK IEWHE                 165

Sequence Number (ID): 15
Length: 141
Molecule Type: AA
Features Location/Qualifiers:
  REGION, 1 ... 141
    > note, A-Syn-120-140_Del-BAP
  source, 1 ... 141
    > mol_type, protein
    > organism, synthetic construct
Residues:

MDVFMKGLSK AKEGVVAAAE KTKQGVAEAA GKTKEGVLYV GSKTKEGVVH GVATVAEKTK   60

EQVTNVGGAV VTGVTAVAQK TVEGAGSIAA ATGFVKKDQL GKNEEGAPQE GILEDMPVDG  120

SAGGSGGLND IFEAQKIEWH E                                           141

Sequence Number (ID): 16
Length: 131
Molecule Type: AA
Features Location/Qualifiers:
   REGION, 1 . . . 131
      > note, alpha synuclein amino acids 1-119
   source, 1 . . . 131
      > mol_type, protein
      > organism, synthetic construct
Residues:

MAHHHHHHIE GRMDVFMKGL SKAKEGVVAA AEKTKQGVAE AAGKTKEGVL YVGSKTKEGV    60

VHGVATVAEK TKEQVTNVGG AVVTGVTAVA QKTVEGAGSI AAATGFVKKD QLGKNEEGAP   120

QEGILEDMPV D                                                       131

Sequence Number (ID): 17
Length: 107
Molecule Type: AA
Features Location/Qualifiers:
   REGION, 1 . . . 107
      > note, kappa (LC constant region)
   source, 1 . . . 107
      > mol_type, protein
      > organism, synthetic construct
Residues:

RTVAAPSVFI FPPSDEQLKS GTASVVCLLN NFYPREAKVQ WKVDNALQSG NSQESVTEQD    60

SKDSTYSLSS TLTLSKADYE KHKVYACEVT HQGLSSPVTK SFNRGEC                107

Sequence Number (ID): 18
Length: 329
Molecule Type: AA
Features Location/Qualifiers:
   REGION, 1 . . . 329
      > note, IgG1 (HC Constant region)
   source, 1 . . . 329
      > mol_type, protein
      > organism, synthetic construct
Residues:

ASTKGPSVFP LAPSSKSTSG GTAALGCLVK DYFPEPVTVS WNSGALTSGV HTFPAVLQSS    60

GLYSLSSVVT VPSSSLGTQT YICNVNHKPS NTKVDKRVEP KSCDKTHTCP PCPAPELLGG   120

PSVFLFPPKP KDTLMISRTP EVTCVVVDVS HEDPEVKFNW YVDGVEVHNA KTKPREEQYN   180

STYRVVSVLT VLHQDWLNGK EYKCKVSNKA LPAPIEKTIS KAKGQPREPQ VYTLPPSREE   240

MTKNQVSLTC LVKGFYPSDI AVEWESNGQP ENNYKTTPPV LDSDGSFFLY SKLTVDKSRW   300

QQGNVFSCSV MHEALHNHYT QKSLSLSPG                                    329

Sequence Number (ID): 19
Length: 4
Molecule Type: AA
Features Location/Qualifiers:
   REGION, 1 . . . 4
      > note, GM285 epitope 112-115
   source, 1 . . . 4
      > mol_type, protein
      > organism, synthetic construct
Residues:

ILED    4

Sequence Number (ID): 20
Length: 13
Molecule Type: AA
Features Location/Qualifiers:
   REGION, 1 . . . 13
      > note, GM285 CDR1 Heavy Chain
   source, 1 . . . 13
      > mol_type, protein
      > organism, synthetic construct
Residues:

AASGFTFSRF TMT    13

Sequence Number (ID): 21
Length: 17
Molecule Type: AA
Features Location/Qualifiers:
REGION, 1 . . . 17
> note, GM285 CDR2 Heavy chain
source, 1 . . . 17
> mol_type, protein
> organism, synthetic construct
Residues:

```
          AISGSGGGTS YADSVKG            17
```

Sequence Number (ID): 22
Length: 9
Molecule Type: AA
Features Location/Qualifiers:
REGION, 1 . . . 9
> note, GM285 CDR3 Heavy chain
source, 1 . . . 9
> mol_type, protein
> organism, synthetic construct
Residues:

```
          AKNWAPFDY            9
```

Sequence Number (ID): 23
Length: 12
Molecule Type: AA
Features Location/Qualifiers:
REGION, 1 . . . 12
> note, GM285 CDR1 Light chain
source, 1 . . . 12
> mol_type, protein
> organism, synthetic construct
Residues:

```
          RASQSVSRSY LA            12
```

Sequence Number (ID): 24
Length: 7
Molecule Type: AA
Features Location/Qualifiers:
REGION, 1 . . . 7
> note, GM285 CDR2 Light chain
source, 1 . . . 7
> mol_type, protein
> organism, synthetic construct
Residues:

```
          GASSRAT            7
```

Sequence Number (ID): 25
Length: 9
Molecule Type: AA
Features Location/Qualifiers:
REGION, 1 . . . 9
> note, GM285 CDR3 Light chain
source, 1 . . . 9
> mol_type, protein
> organism, synthetic construct
Residues:

```
          QQYGSSPWT            9
```

Sequence Number (ID): 26
Length: 116
Molecule Type: AA
Features Location/Qualifiers:
REGION, 1 . . . 116
> note, GM285 VH
source, 1 . . . 116
> mol_type, protein
> organism, synthetic construct
Residues:

```
EVQLLESGGG LVQPGGSLRL SCAASGFTFS RFTMTWVRQA PGKGLEWVSA ISGSGGGTSY   60
ADSVKGRLTV SRDNSKNTLY LQMNSLRAED TAVYYCAKNW APFDYWGQGT LVTVSS      116
```

Sequence Number (ID): 27
Length: 108
Molecule Type: AA
Features Location/Qualifiers:
REGION, 1 . . . 108
> note, GM285 VL
source, 1 . . . 108
> mol_type, protein
> organism, synthetic construct
Residues:

```
EIVLTQSPGT LSLSPGERAT LSCRASQSVS RSYLAWYQQK PGQAPRLLIY GASSRATGIP   60
DRFSGSGSGT DFTLTVSRLE PEDFAVYYCQ QYGSSPWTFG QGTKVEIK              108
```

Sequence Number (ID): 28
Length: 329
Molecule Type: AA
Features Location/Qualifiers:
  REGION, 1 . . . 329
    > note, GM285 IgG1 constant region
  source, 1 . . . 329
    > mol_type, protein
    > organism, synthetic construct
Residues:

ASTKGPSVFP LAPSSKSTSG GTAALGCLVK DYFPEPVTVS WNSGALTSGV HTFPAVLQSS 60

GLYSLSSVVT VPSSSLGTQT YICNVNHKPS NTKVDKRVEP KSCDKTHTCP PCPAPELLGG 120

PSVFLFPPKP KDTLMISRTP EVTCVVVDVS HEDPEVKFNW YVDGVEVHNA KTKPREEQYN 180

STYRVVSVLT VLHQDWLNGK EYKCKVSNKA LPAPIEKTIS KAKGQPREPQ VYTLPPSREE 240

MTKNQVSLTC LVKGFYPSDI AVEWESNGQP ENNYKTTPPV LDSDGSFFLY SKLTVDKSRW 300

QQGNVFSCSV MHEALHNHYT QKSLSLSPG 329

Sequence Number (ID): 29
Length: 106
Molecule Type: AA
Features Location/Qualifiers:
  REGION, 1 . . . 106
    > note, GM285 Kappa chain
  source, 1 . . . 106
    > mol_type, protein
    > organism, synthetic construct
Residues:

TVAAPSVFIF PPSDEQLKSG TASVVCLLNN FYPREAKVQW KVDNALQSGN SQESVTEQDS 60

KDSTYSLSST LTLSKADYEK HKVYACEVTH QGLSSPVTKS FNRGEC 106

Sequence Number (ID): 30
Length: 116
Molecule Type: AA
Features Location/Qualifiers:
  REGION, 1 . . . 116
    > note, GM37 Variant 1 heavy chain
  source, 1 . . . 116
    > mol_type, protein
    > organism, synthetic construct
Residues:

EVQLLESGGG LVQTGGSLRL SCAASGFTFS SYAMTWVRQA PGKGLEWVSA IRSSGDRTDY 60

ADSVKGRFTI SRDNSQNTLY LQMNSLRAED TAVYYCAKNW APFDSWGQGT LVTVSS 116

Sequence Number (ID): 31
Length: 116
Molecule Type: AA
Features Location/Qualifiers:
  REGION, 1 . . . 116
    > note, GM 37 variant 2 heavy chain
  source, 1 . . . 116
    > mol_type, protein
    > organism, synthetic construct
Residues:

EVQLLESGGG LVQTGGSLRL SCAASGFTFS SYAMTWVRQA PGKGLEWVSA IRSQGDRTDY 60

ADSVKGRFTI SRDNSQNTLY LQMNSLRAED TAVYYCAKNW APFDSWGQGT LVTVSS 116

Sequence Number (ID): 32
Length: 116
Molecule Type: AA
Features Location/Qualifiers:
  REGION, 1 . . . 116
    > note, GM 37 variant 3 heavy chain
  source, 1 . . . 116
    > mol_type, protein
    > organism, synthetic construct
Residues:

EVQLLESGGG LVQTGGSLRL SCAASGFTFS SYAMTWVRQA PGKGLEWVSA IRSHGDRTDY  60

ADSVKGRFTI SRDNSQNTLY LQMNSLRAED TAVYYCAKNW APFDSWGQGT LVTVSS  116

Sequence Number (ID): 33
Length: 17
Molecule Type: AA
Features Location/Qualifiers:
  REGION, 1 . . . 17
    > note, GM37 variant 1 heavy chain CDR 2
  source, 1 . . . 17
    > mol_type, protein
    > organism, synthetic construct
Residues:

AIRSSGDRTD YADSVKG        17

Sequence Number (ID): 34
Length: 17
Molecule Type: AA
Features Location/Qualifiers:
  REGION, 1 . . . 17
    > note, GM37 variant 2 CDR 2 heavy chain
  source, 1 . . . 17
    > mol_type, protein
    > organism, synthetic construct
Residues:

AIRSQGDRTD YADSVKG        17

Sequence Number (ID): 35
Length: 17
Molecule Type: AA
Features Location/Qualifiers:
  REGION, 1 . . . 17
    > note, GM37 variant 3 CDR 2 heavy chain
  source, 1 . . . 17
    > mol_type, protein
    > organism, synthetic construct
Residues:

AIRSQGDRTD YADSVKG        17

Sequence Number (ID): 36
Length: 5
Molecule Type: AA
Features Location/Qualifiers:
  REGION, 1 . . . 5
    > note, 9E4 binding epitope
  source, 1 . . . 5
    > mol_type, protein
    > organism, synthetic construct
Residues

NEAYE        5

Sequence Number (ID): 37
Length: 134
Molecule Type: AA
Features Location/Qualifiers:
  REGION, 1 . . . 134
    > note, HUMAN Beta-synuclein
  source, 1 . . . 134
    > mol_type, protein
    > organism, synthetic construct
Residues:

MDVFMKGLSM AKEGVVAAAE KTKQGVTEAA EKTKEGVLYV GSKTREGVVQ GVASVAEKTK  60

EQASHLGGAV FSGAGNIAAA TGLVKREEFP TDLKPEEVAQ EAAEEPLIEP LMEPEGESYE  120

DPPQEEYQEY EPEA  134

Sequence Number (ID): 38
Length: 127
Molecule Type: AA
Features Location/Qualifiers:
  REGION, 1 . . . 127
    > note, HUMAN Gamma-synuclein
  source, 1 . . . 127
    > mol_type, protein
    > organism, synthetic construct
Residues:

MDVFKKGFSI AKEGVVGAVE KTKQGVTEAA EKTKEGVMYV GAKTKENVVQ SVTSVAEKTK  60

EQANAVSEAV VSSVNTVATK TVEEAENIAV TSGVVRKEDL RPSAPQQEGE ASKEKEEVAE  120

EAQSGGD  127

Sequence Number (ID): 39
Length: 140
Molecule Type: AA
Features Location/Qualifiers:
    REGION, 1 ... 140
        > note, alpha synuclein ortholog for Cynomolgus monkey
    source, 1 ... 140
        > mol_type, protein
        > organism, synthetic construct
Residues:

MDVFMKGLSK AKEGVVAAAE KTKQGVAEAA GKTKEGVLYV GSKTKEGVVH GVATVAEKTK 60

EQVTNVGGAV VTGVTAVAQK TVEGAGSIAA ATGFIKKDQL GKNEEGAPQE GILQDMPVDP 120

DNEAYEMPSE EGYQDYEPEA 140

Sequence Number (ID): 40
Length: 140
Molecule Type: AA
Features Location/Qualifiers:
    REGION, 1 ... 140
        > note, alpha synuclein ortholog for Rat
    source, 1 ... 140
        > mol_type, protein
        > organism, synthetic construct
Residues:

MDVFMKGLSK AKEGVVAAAE KTKQGVAEAA GKTKEGVLYV GSKTKEGVVH GVTTVAEKTK 60

EQVTNVGGAV VTGVTAVAQK TVEGAGNIAA ATGFVKKDQM GKGEEGYPQE GILEDMPVDP 120

SSEAYEMPSE EGYQDYEPEA 140

Sequence Number (ID): 41
Length: 140
Molecule Type: AA
Features Location/Qualifiers:
    REGION, 1 ... 140
        > note, alpha synuclein ortholog for Mouse
    source, 1 ... 140
        > mol_type, protein
        > organism, synthetic construct
Residues:

MDVFMKGLSK AKEGVVAAAE KTKQGVAEAA GKTKEGVLYV GSKTKEGVVH GVTTVAEKTK 60

EQVTNVGGAV VTGVTAVAQK TVEGAGNIAA ATGFVKKDQM GKGEEGYPQE GILEDMPVDP 120

GSEAYEMPSE EGYQDYEPEA 140

Sequence Number (ID): 42
Length: 446
Molecule Type: AA
Features Location/Qualifiers:
    REGION, 1 ... 446
        > note, 9E4 HC
    source, 1 ... 446
        > mol_type, protein
        > organism, synthetic construct
Residues:

EVQLVESGGG LVQPGGSLRL SCAASGFTFS NYGMSWVRQA PGKGLEWVAS ISSGGGSTYY 60

PDNVKGRFTI SRDNAKNSLY LQMNSLRAED TAVYYCARGG AGIDYWGQGT LVTVSSASTK 120

```
                                            -continued
GPSVFPLAPS SKSTSGGTAA LGCLVKDYFP EPVTVSWNSG ALTSGVHTFP AVLQSSGLYS    180

LSSVVTVPSS SLGTQTYICN VNHKPSNTKV DKRVEPKSCD KTHTCPPCPA PELLGGPSVF    240

LFPPKPKDTL MISRTPEVTC VVVDVSHEDP EVKFNWYVDG VEVHNAKTKP REEQYNSTYR    300

VVSVLTVLHQ DWLNGKEYKC KVSNKALPAP IEKTISKAKG QPREPQVYTL PPSREEMTKN    360

QVSLTCLVKG FYPSDIAVEW ESNGQPENNY KTTPPVLDSD GSFFLYSKLT VDKSRWQQGN    420

VFSCSVMHEA LHNHYTQKSL SLSPGK                                        446
```

Sequence Number (ID): 43
Length: 220
Molecule Type: AA
Features Location/Qualifiers:
 REGION, 1 . . . 220
  > note, 9E4 LC
 source, 1 . . . 220
  > mol_type, protein
  > organism, synthetic construct
Residues:

```
DIQMTQSPSS LSASVGDRVT ITCKSIQTLL YSSNQKNYLA WFQQKPGKAP KLLIYWASIR    60

KSGVPSRFSG SGSGTDFTLT ISSLQPEDLA TYYCQQYYSY PLTFGGGTKL EIKRTVAAPS    120

VFIFPPSDEQ LKSGTASVVC LLNNFYPREA KVQWKVDNAL QSGNSQESVT EQDSKDSTYS    180

LSSTLTLSKA DYEKHKVYAC EVTHQGLSSP VTKSFNRGEC                         220
```

The antibodies for use according to the present invention may be obtained from any suitable source and may in some embodiments be produced in different cell lines, such as be produced in a human cell line, a mammal non-human cell line, or insect cell line, for example be produced in a CHO cell line, a HEK cell line, a BHK-21 cell line, a murine cell line (such as a myeloma cell line), a fibrosarcoma cell line, a PER.C6 cell line, a HKB-11 cell line, a CAP cell line or a HuH-7 human cell line.

In one embodiment, the antibody for use according to the invention is a human antibody. Human monoclonal antibodies directed against alpha synuclein may be generated using transgenic or transchromosomal mice carrying parts of the human immune system rather than the mouse system. Such transgenic and transchromosomic mice include mice may be referred to as HuMAb mice and KM mice, respectively.

In one embodiment the antibodies for use according to the present invention, exemplified by GM37 its variants GM37 var 1-3 and GM285 are capable of binding the toxic alpha synuclein fragments consisting of residues 1-119/122 of alpha synuclein and neutralizing its toxicity (for example, by extracellular binding to the alpha synuclein fragment and thereby preventing it from being taken up by cells). In a further embodiment the antibodies for use according to the present invention, are capable of binding to an epitope within amino acids 112-117 of alpha synuclein and binds toxic alpha synuclein species in human brain. In a further embodiment the antibodies for use according to the present invention have effects on clearing extracellular alpha synuclein and normalizing an impaired synaptic transmission induced by alpha synuclein in vivo. In yet another embodiment the antibodies for use according to the invention are also able to ameliorate the appearance of a relevant motor phenotype in a rat model for Parkinson's disease. All these properties are described in detail in WO2017/009312.

Pharmaceutical Formulations and Administration Routes

The present invention also provides a process for making a pharmaceutical composition comprising an antibody for use according to the invention. Such pharmaceutical compositions may be formulated with pharmaceutically acceptable buffers, carriers or diluents as well as any other known adjuvants or excipients in accordance with conventional techniques.

A pharmaceutical composition of the present invention may include diluents, fillers, salts, buffers, detergents (e.g., a non-ionic detergent, such as Tween-20 or Tween-80), stabilizers (e.g., sugars or protein-free amino acids), preservatives, tissue fixatives, solubilizers, and/or other materials suitable for inclusion in a pharmaceutical composition.

In addition, the pharmaceutical composition or formulation may also include other carriers, or non-toxic, nontherapeutic, non-immunogenic stabilizers and the like. The compositions may also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes).

Pharmaceutically acceptable carriers include any and all suitable solvents, dispersion media, coatings, antibacterial and antifungal agents, isotonicity agents, antioxidants and absorption delaying agents, and the like that are physiologically compatible with an antibody for use according to the invention. Examples of suitable aqueous and non-aqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and organic esters, such as ethyl oleate, and/or various buffers. Other carriers are well known in the pharmaceutical arts and may also be employed in the present invention.

Pharmaceutically acceptable carriers include sterile aqueous solutions or dispersions and sterile powders for the extemporaneous preparation of sterile solutions.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition.

The antibodies of the present invention may be prepared with carriers that will protect the antibody against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art.

Pharmaceutical compositions for infusion must typically be sterile and stable under the conditions of manufacture and storage. The composition may be formulated as a solution, micro-emulsion, liposome, or other ordered structure suitable to high drug concentration. The carrier may be an aqueous or non-aqueous solvent or dispersion medium containing for instance water, ethanol, polyols (such as glycerol, propylene glycol, polyethylene glycol, and the like), and suitable mixtures thereof, vegetable oils, such as olive oil, and organic esters, such as ethyl oleate.

Sterile solutions for infusion may be prepared by incorporating the active antibody in the required amount in an appropriate solvent with one or a combination of ingredients e.g. as enumerated above, as required, followed by sterilization microfiltration. Generally, dispersions are prepared by incorporating the active antibody into a sterile vehicle that contains a basic dispersion medium and the required other ingredients e.g. from those enumerated above. In the case of sterile powders for the preparation of sterile solutions, examples of methods of preparation are vacuum drying and freeze-drying (lyophilization) that yield a powder of the active ingredient plus any additional desired ingredient from a previously sterile-filtered solution thereof.

Compositions may be formulated in dosage unit form for ease of administration and uniformity of dosage. Dosage unit form as used herein refers to units suited as unitary dosages for the subjects to be treated; each unit contains a predetermined quantity of active antibody which produce the desired therapeutic effect in association with the required pharmaceutical excipients.

In a particular embodiment the pharmaceutical composition is administered by intravenous infusion.

Specific Liquid Pharmaceutical Compositions of the Invention

In an aspect of the invention the antibody for use according to the invention is formulated as a liquid pharmaceutical composition and administered by intravenous infusion.

In one aspect the present invention provides a liquid pharmaceutical composition comprising a full length IgG1 monoclonal anti-alpha synuclein antibody in a concentration of about 20-230 mg/mL, such as 25-225 mg/mL, wherein said antibody comprises:
   a. a Heavy Chain CDR1 having the amino acid sequence of SEQ ID NO:1;
   b. a Heavy Chain CDR2 having the amino acid sequence of SEQ ID NO:34;
   c. a Heavy Chain CDR3 having the amino acid sequence of SEQ ID NO:3;
   d. a Light Chain CDR1 having the amino acid sequence of SEQ ID NO:4;
   e. a Light Chain CDR2 having the amino acid sequence of SEQ ID NO:5; and
   f. a Light Chain CDR3 having the amino acid sequence of SEQ ID NO:6;

and wherein the composition further comprises a buffering agent, a pharmaceutically acceptable tonicity agent, a pharmaceutically acceptable surfactant and wherein the pH of the composition is between 4.5 to 7.5, such as 5.0 to 7.0, such as 5.5. to 6.5, such as 6.0.

In a preferred embodiment the liquid pharmaceutical composition of the invention is a stable liquid pharmaceutical composition. In a preferred embodiment the liquid pharmaceutical composition of the invention is a low viscosity liquid pharmaceutical composition. In a preferred embodiment the liquid pharmaceutical composition of the invention is a stable and low viscosity liquid pharmaceutical composition. In a preferred embodiment the liquid pharmaceutical composition of the invention is suitable for clinical use and safe for patients in need of administration/dosing of the liquid pharmaceutical composition.

In certain embodiments the monoclonal anti-alpha synuclein antibody of the liquid pharmaceutical composition further comprises a heavy chain consisting of a variable domain of SEQ ID NO:31 and a light chain consisting of a variable domain of SEQ ID NO:8. In a more specific embodiment the monoclonal anti-alpha synuclein antibody further comprises a constant heavy chain domain as defined in SEQ ID NO:18 and a kappa light chain constant domain as defined in SEQ ID NO:17.

In certain embodiments the monoclonal anti-alpha synuclein antibody of the liquid pharmaceutical composition of the invention is GM37v2.

In some embodiment the liquid pharmaceutical composition comprises the monoclonal anti-alpha synuclein antibody at a concentration of more than 20 mg/mL, and in some embodiment, at a concentration of less than 230 mg/mL. In further embodiments the concentration of the monoclonal anti-alpha synuclein antibody in the pharmaceutical composition is between 20-225 mg/mL 20-220 mg/mL, 20-215 mg/mL, 20-210 mg/mL, 20-205 mg/mL, 20-200 mg/mL, 20-195 mg/mL, 20-190 mg/mL, 20-185 mg/mL, 20-180 mg/mL, 20-175 mg/mL, 20-170 mg/mL, 20-165 mg/mL, 20-160 mg/mL, 20-155 mg/mL, 20-150 mg/mL, 20-145 mg/mL, 20-140 mg/mL, 20-135 mg/mL, 20-130 mg/mL, 20-125 mg/mL, 20-120 mg/mL, 20-115 mg/mL, 20-110 mg/mL, 20-105 mg/mL, 20-100 mg/mL, 20-95 mg/mL, 20-90 mg/mL, 20-85 mg/mL, 20-80 mg/mL, 20-75 mg/mL, 20-70 mg/mL, 20-65 mg/mL, 20-60 mg/mL, 20-55 mg/mL, 20-50 mg/mL, 20-45 mg/mL, 20-40 mg/mL, 20-35 mg/mL, 20-30 mg/mL, 20-25 mg/mL, 25-230 mg/mL, 30-230 mg/mL, 35-230 mg/mL, 40-230 mg/mL, 45-230 mg/mL, 50-230 mg/mL, 55-230 mg/mL, 60-230 mg/mL, 65-230 mg/mL, 70-230 mg/mL, 75-230 mg/mL, 80-230 mg/mL, 85-230 mg/mL, 90-230 mg/mL, 95-230 mg/mL, 100-230 mg/mL, 105-230 mg/mL, 110-230 mg/mL, 115-230 mg/mL, 120-230 mg/mL, 125-230 mg/mL, 130-230 mg/mL, 135-

230 mg/mL, 140-230 mg/mL, 145-230 mg/mL, 150-230 mg/mL, 155-230 mg/mL, 160-230 mg/mL, 165-230 mg/mL, 170-230 mg/mL, 175-230 mg/mL, 180-230 mg/mL, 185-230 mg/mL, 190-230 mg/mL, 195-230 mg/mL, 200-230 mg/mL, 205-230 mg/mL, 210-230 mg/mL, 215-230 mg/mL, 220-230 mg/mL, 225-230 mg/mL, 25-225 mg/mL, 30-220 mg/mL, 35-215 mg/mL, 40-210 mg/mL, 45-205 mg/mL, 50-200 mg/mL, 55-195 mg/mL, 60-190 mg/mL, 65-185 mg/mL, 70-180 mg/mL, 75-175 mg/mL, 80-170 mg/mL, 85-165 mg/mL, 90-160 mg/mL, 95-155 mg/mL, 100-150 mg/mL, 105-145 mg/mL, 110-140 mg/mL, 115-135 mg/mL or 120-130 mg/mL; including every value in between these numbers.

In specific embodiments the liquid pharmaceutical composition comprises the monoclonal anti-alpha synuclein antibody at a concentration of about 50 mg/mL. In another specific embodiments the monoclonal anti-alpha synuclein antibody of the liquid pharmaceutical composition has a concentration of about 53 mg/mL. In some embodiment the monoclonal anti-alpha synuclein antibody of the liquid pharmaceutical composition has a concentration of within +/−30% of said values, such as +/−25%, such as +/−20%, such as +/−15%, such as +/−10% of said values, such as +/−8%, such as +/−6%, such as +/−5%, such as +/−4%, such as +/−3%, such as +/−2.5%, such as +/−2%, such as +/−1.5%, such as +/−1%, such as +/−0.75%, such as +/−0.5%, such as +/−0.25%, such as +/−0.1%, such as +/−0.05%, such as +/−0.025%, such as +/−0.01%, such as +/−0.0075%, such as +/−0.005%, such as +/−0.0025%, such as +/−0.001% or such as +/−0.0005%.

In some embodiments of the present invention the buffering agent is a single buffering agent or a mixture of buffering agents. In a further embodiment of the invention the buffering agent is selected from Acetate, Citrate, Tartrate, Histidine, Glutamate, Phosphate, Tris, Glycine, Bicarbonate, Succinate, Sulfate or Nitrate buffers or a mixture thereof. In further embodiments the buffering agents are selected from sodium phosphate, histidine (such as L-Histidine), citric acid, sodium citrate, sodium acetate or a mixture thereof. In a specific embodiment, the buffering agent is a Histidine buffer (such as L-Histidine) or a mixture of Histidine buffers. The Histidine buffer can be selected from Histidine buffers and mixtures thereof such as Histidine, L-Histidine, L-Histidine hydrochloride, L-Histidine monohydrochloride, L-Histidine monohydrate and L-Histidine hydrochloride monohydrate or mixtures thereof. In one preferred embodiment, the histidine buffer is a mixture of L-Histidine and L-Histidine monohydrochloride. In some preferred embodiments of the liquid pharmaceutical composition of the invention the buffering agent is present in a concentration between 10-60 mM, such as 15-55 mM, such as 20-50 mM, such as 20-45 mM, such as 20-40 mM, such as 25-40 mM, such as 10-40 mM, such as 15-35 mM, such as 20-30 mM or such as 25 mM. In some embodiment the buffering agent of the liquid pharmaceutical composition has a concentration of within +/−30% of said values, such as +/−25%, such as +/−20%, such as +/−15%, such as +/−10% of said values, such as +/−8%, such as +/−6%, such as +/−5%, such as +/−4%, such as +/−3%, such as +/−2.5%, such as +/−2%, such as +/−1.5%, such as +/−1%, such as +/−0.75%, such as +/−0.5%, such as +/−0.25%, such as +/−0.1%, such as +/−0.05%, such as +/−0.025%, such as +/−0.01%, such as +/−0.0075%, such as +/−0.005%, such as +/−0.0025%, such as +/−0.001% or such as +/−0.0005%.

In an embodiment the pH of the liquid pharmaceutical composition of the invention is in the range from about 4.5 to about 7.5, such as 4.5 to about 6.5, such as 5.0 to 6.5, such as from about 5.5 to about 6.5, for example from 5.7 to 6.4, 5.8 to 6.3 or 5.9 to 6.2. In one embodiment the liquid pharmaceutical composition has a pH of 5.5, 5.6, 5.7, 5.8, 5.9, 6.0, 6.1, 6.2, 6.3, 6.4, 6.5 or 7.0. Histidine buffers (such as L-histidine) are example of buffers that may be comprised in the liquid pharmaceutical composition of the invention that will control the pH in this range. In a preferred embodiment the pH of the liquid pharmaceutical composition of the invention is 6.0. In some embodiment the liquid pharmaceutical composition has a pH within +/−30% of said values, such as +/−25%, such as +/−20%, such as +/−15%, such as +/−10% of said values, such as +/−8%, such as +/−6%, such as +/−5%, such as +/−4%, such as +/−3%, such as +/−2.5%, such as +/−2%, such as +/−1.5%, such as +/−1%, such as +/−0.75%, such as +/−0.5%, such as +/−0.25%, such as +/−0.1%, such as +/−0.05%, such as +/−0.025%, such as +/−0.01%, such as +/−0.0075%, such as +/−0.005%, such as +/−0.0025%, such as +/−0.001% or such as +/−0.0005%.

In an embodiment the surfactant of the liquid pharmaceutical composition of the invention is a non-ionic surfactant. In further embodiments, the surfactant is selected from the group consisting of polysorbate (for example, polysorbate 20 and polysorbate 80); poloxamer (e.g. poloxamer 188); Triton; Triton X-100; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyldimethylamine; sodium methyl cocoyl-, or disodium methyl oleyl-taurate; polyethyl glycol, polypropyl glycol, and copolymers of ethylene and propylene glycol. In one specific embodiment, the pharmaceutically acceptable surfactant of the liquid pharmaceutical composition of the invention is polysorbate 80 also known as Tween 80. In some preferred embodiments of the liquid pharmaceutical composition of the invention the surfactant is present in an amount of between 0.001% to 0.10% (w/v), such as 0.005% to 0.08% (w/v), such as 0.008% to 0.06% (w/v), such as 0.01% to 0.05% (w/v), such as 0.015% to 0.05% (w/v), such as 0.01% to 0.05% (w/v), such as 0.01% to 0.03% (w/v) or such as 0.02% (w/v). In some embodiment the surfactant of the liquid pharmaceutical composition has a concentration of within +/−30% of said values, such as +/−25%, such as +/−20%, such as +/−15%, such as +/−10% of said values, such as +/−8%, such as +/−6%, such as +/−5%, such as +/−4%, such as +/−3%, such as +/−2.5%, such as +/−2%, such as +/−1.5%, such as +/−1%, such as +/−0.75%, such as +/−0.5%, such as +/−0.25%, such as +/−0.1%, such as +/−0.05%, such as +/−0.025%, such as +/−0.01%, such as +/−0.0075%, such as +/−0.005%, such as +/−0.0025%, such as +/−0.001% or such as +/−0.0005%.

In an embodiment the tonicity agent of the liquid pharmaceutical composition of the invention is selected from Mannitol, Sorbitol, Lactose, Dextrose, Trehalose, Sodium Chloride, Potassium Chloride, Glycerol and Glycerine. In one specific embodiment, the tonicity agent is a suitable salt such as NaCl. In one specific embodiment, the tonicity agent of the liquid pharmaceutical composition of the invention is sodium chloride (NaCl). In some preferred embodiments of the liquid pharmaceutical composition of the invention the tonicity agent is present in a concentration of 10-150 mM, such as 10-150 mM, such as 10-150 mM, such as 10-150 mM, such as 10-150 mM, such as 20-140 mM, such as 30-130 mM, such as 40-120 mM, such as 50-110 mM, such as 60-110 mM, such as 70-110 mM, such as 80-110 mM, such as 90-110 mM or such as about 100 mM. In some embodiment the tonicity agent of the liquid pharmaceutical composition has a concentration of within +/−30% of said values, such as +/−25%, such as +/−20%, such as +/−15%, such as +/−10% of said values, such as +/−8%, such as +/−6%, such as +/−5%, such as +/−4%, such as +/−3%, such as +/−2.5%, such as +/−2%, such as +/−1.5%, such as +/−1%, such as +/−0.75%, such as +/−0.5%, such as +/−0.25%, such as +/−0.1%, such as +/−0.05%, such as +/−0.025%, such as +/−0.01%, such as +/−0.0075%, such as +/−0.005%, such as +/−0.0025%, such as +/−0.001% or such as +/−0.0005%.

In an embodiment the liquid pharmaceutical composition of the invention further comprises a bulking agent which is selected from Sugars and polyols (such as Sucrose, Trehalose, Glucose, Lactose, Sorbitol, Mannitol and Glycerol); Amino Acids (such as Arginine, Aspartic Acid, Glutamic acid, Lysine, Glycine, Glutamate, Histidine, Methionine or Alanine); or Polymers and proteins (such as Gelatin, PVP, PLGA, PEG, dextran, cyclodextrin and derivatives, starch derivatives, HSA or BSA). In one specific embodiment, the bulking agent is selected from Arginine, Glutamate, Sucrose, Glycine or Sorbitol. In one specific embodiment, the bulking agent is sucrose. In some preferred embodiments of the liquid pharmaceutical composition of the invention the bulking agent is present in a concentration of 20-200 mM, such as 25-180 mM, such as 30-170 mM, such as 35-160 mM, such as 40-150 mM, such as 45-140 mM, such as 50-130 mM, such as 60-130 mM, such as 65-120 mM, such as 70-120 mM, such as 75-120 mM, such as 80-110 mM, such as 85-110 mM, such as 90-110 mM, such as 95-110 mM, such as 95-105 mM or such as 100 mM. In some embodiment the bulking agent of the liquid pharmaceutical composition has a concentration of within +/−30% of said values, such as +/−25%, such as +/−20%, such as +/−15%, such as +/−10% of said values, such as +/−8%, such as +/−6%, such as +/−5%, such as +/−4%, such as +/−3%, such as +/−2.5%, such as +/−2%, such as +/−1.5%, such as +/−1%, such as +/−0.75%, such as +/−0.5%, such as +/−0.25%, such as +/−0.1%, such as +/−0.05%, such as +/−0.025%, such as +/−0.01%, such as +/−0.0075%, such as +/−0.005%, such as +/−0.0025%, such as +/−0.001% or such as +/−0.0005%.

In an embodiment the liquid pharmaceutical composition of the invention comprises the monoclonal anti-alpha synuclein antibody, GM37v2, histidine buffer and sodium chloride (NaCl) at pH 4.5-7.5.

In an embodiment the liquid pharmaceutical composition of the invention comprises 20-230 mg/mL of the monoclonal anti-alpha synuclein antibody, GM37v2, 10-60 mM histidine buffer and 10-150 mM sodium chloride (NaCl) at pH 4.5-7.5.

In an embodiment the liquid pharmaceutical composition of the invention comprises 40-60 mg/mL of the monoclonal anti-alpha synuclein antibody, GM37v2, 20-30 mM histidine buffer and 90-110 mM sodium chloride (NaCl) at pH 5.5-6.5.

In an embodiment the liquid pharmaceutical composition of the invention comprises 53 mg/mL of the monoclonal anti-alpha synuclein antibody, GM37v2, 25 mM histidine buffer and 100 mM sodium chloride (NaCl) at pH 6.0.

In an embodiment the liquid pharmaceutical composition of the invention comprises 53 mg/mL of the monoclonal anti-alpha synuclein antibody, GM37v2, 25 mM histidine buffer and 100 mM sodium chloride (NaCl) at pH 6.0 or within +/−30% of said values, such as +/−25%, such as +/−20%, such as +/−15%, such as +/−10%, such as +/−5%, such as +/−1%, such as +/−0.5%, such as +/−0.25% or such as +/−0.1%.

In an embodiment the liquid pharmaceutical composition of the invention comprises the monoclonal anti-alpha synuclein antibody, GM37v2, histidine buffer and polysorbate 80 (tween 80) at pH 4.5-7.5.

In an embodiment the liquid pharmaceutical composition of the invention comprises 20-230 mg/mL of the monoclonal anti-alpha synuclein antibody, GM37v2, 10-60 mM histidine buffer and polysorbate 80 (tween 80) in an amount of between 0.001% to 0.10% (w/v), at pH 4.5-7.5.

In an embodiment the liquid pharmaceutical composition of the invention comprises 40-60 mg/mL of the monoclonal anti-alpha synuclein antibody, GM37v2, 20-30 mM histidine buffer and polysorbate 80 (tween 80) in an amount of between 0.01% to 0.03% (w/v), at pH 5.5-6.5.

In an embodiment the liquid pharmaceutical composition of the invention comprises 53 mg/mL of the monoclonal anti-alpha synuclein antibody, GM37v2, 25 mM histidine buffer and polysorbate 80 (tween 80) in an amount of 0.02% (w/v), at pH 6.0.

In an embodiment the liquid pharmaceutical composition of the invention comprises 53 mg/mL of the monoclonal anti-alpha synuclein antibody, GM37v2, 25 mM histidine buffer and polysorbate 80 (tween 80) in an amount of 0.02% (w/v), at pH 6.0 or within +/−30% of said values, such as +/−25%, such as +/−20%, such as +/−15%, such as +/−10%, such as +/−5%, such as +/−1%, such as +/−0.5%, such as +/−0.25% or such as +/−0.1%.

In an embodiment the liquid pharmaceutical composition of the invention comprises the monoclonal anti-alpha synuclein antibody, GM37v2, histidine buffer, sodium chloride (NaCl) and polysorbate 80 (tween 80) at pH 4.5-7.5.

In an embodiment the liquid pharmaceutical composition of the invention comprises 20-230 mg/mL of the monoclonal anti-alpha synuclein antibody, GM37v2, 10-60 mM histidine buffer, 10-150 mM sodium chloride (NaCl) and polysorbate 80 (tween 80) in an amount of between 0.001% to 0.10% (w/v), at pH 4.5-7.5.

In an embodiment the liquid pharmaceutical composition of the invention comprises 40-60 mg/mL of the monoclonal anti-alpha synuclein antibody, GM37v2, 20-30 mM histidine buffer, 90-110 mM sodium chloride (NaCl) and polysorbate 80 (tween 80) in an amount of between 0.01% to 0.03% (w/v), at pH 5.5-6.5.

In an embodiment the liquid pharmaceutical composition of the invention comprises 53 mg/mL of the monoclonal anti-alpha synuclein antibody, GM37v2, 25 mM histidine buffer, 100 mM sodium chloride (NaCl) and polysorbate 80 (tween 80) in an amount of 0.02% (w/v), at pH 6.0.

In an embodiment the liquid pharmaceutical composition of the invention comprises 53 mg/mL of the monoclonal anti-alpha synuclein antibody, GM37v2, 25 mM histidine buffer, 100 mM sodium chloride (NaCl) and polysorbate 80 (tween 80) in an amount of 0.02% (w/v), at pH 6.0 or within +/−30% of said values, such as +/−25%, such as +/−20%, such as +/−15%, such as +/−10%, such as +/−5%, such as +/−1%, such as +/−0.5%, such as +/−0.25% or such as +/−0.1%.

In an embodiment the liquid pharmaceutical composition of the invention comprises the monoclonal anti-alpha synuclein antibody, GM37v2, histidine buffer, sodium chloride (NaCl) and sucrose at pH 4.5-7.5.

In an embodiment the liquid pharmaceutical composition of the invention comprises 20-230 mg/mL of the monoclonal anti-alpha synuclein antibody, GM37v2, 10-60 mM histidine buffer, 10-150 mM sodium chloride (NaCl) and 20-200 mM sucrose, at pH 4.5-7.5.

In an embodiment the liquid pharmaceutical composition of the invention comprises 40-60 mg/mL of the monoclonal anti-alpha synuclein antibody, GM37v2, 20-30 mM histidine buffer, 90-110 mM sodium chloride (NaCl) and 90-110 mM sucrose, at pH 5.5-6.5.

In an embodiment the liquid pharmaceutical composition of the invention comprises 53 mg/mL of the monoclonal anti-alpha synuclein antibody, GM37v2, 25 mM histidine buffer, 100 mM sodium chloride (NaCl) and 100 mM sucrose, at pH 6.0.

In an embodiment the liquid pharmaceutical composition of the invention comprises 53 mg/mL of the monoclonal anti-alpha synuclein antibody, GM37v2, 25 mM histidine buffer, 100 mM sodium chloride (NaCl) and 100 mM sucrose, at pH 6.0 or within +/−30% of said values, such as +/−25%, such as +/−20%, such as +/−15%, such as +/−10%, such as +/−5%, such as +/−1%, such as +/−0.5%, such as +/−0.25% or such as +/−0.1%.

In an embodiment the liquid pharmaceutical composition of the invention comprises the monoclonal anti-alpha synuclein antibody, GM37v2, histidine buffer, sucrose and polysorbate 80 (tween 80) at pH 4.5-7.5.

In an embodiment the liquid pharmaceutical composition of the invention comprises 20-230 mg/mL of the monoclonal anti-alpha synuclein antibody, GM37v2, 10-60 mM histidine buffer, 20-200 mM sucrose and polysorbate 80 (tween 80) in an amount of between 0.001% to 0.10% (w/v), at pH 4.5-7.5.

In an embodiment the liquid pharmaceutical composition of the invention comprises 40-60 mg/mL of the monoclonal anti-alpha synuclein antibody, GM37v2, 20-30 mM histidine buffer, 90-110 mM sucrose and polysorbate 80 (tween 80) in an amount of between 0.01% to 0.03% (w/v), at pH 5.5-6.5.

In an embodiment the liquid pharmaceutical composition of the invention comprises 53 mg/mL of the monoclonal anti-alpha synuclein antibody, GM37v2, 25 mM histidine buffer, 100 mM sucrose and polysorbate 80 (tween 80) in an amount of 0.02% (w/v), at pH 6.0.

In an embodiment the liquid pharmaceutical composition of the invention comprises 53 mg/mL of the monoclonal anti-alpha synuclein antibody, GM37v2, 25 mM histidine buffer, 100 mM sucrose and polysorbate 80 (tween 80) in an amount of 0.02% (w/v), at pH 6.0 or within +/−30% of said values, such as +/−25%, such as +/−20%, such as +/−15%, such as +/−10%, such as +/−5%, such as +/−1%, such as +/−0.5%, such as +/−0.25% or such as +/−0.1%.

In an embodiment the liquid pharmaceutical composition of the invention comprises the monoclonal anti-alpha synuclein antibody, GM37v2, histidine buffer, sodium chloride (NaCl), sucrose and polysorbate 80 (tween 80) at pH 4.5-7.5.

In an embodiment the liquid pharmaceutical composition of the invention comprises 20-230 mg/mL of the monoclonal anti-alpha synuclein antibody, GM37v2, 10-60 mM histidine buffer, 10-150 mM sodium chloride (NaCl), 20-200 mM sucrose and polysorbate 80 (tween 80) in an amount of between 0.001% to 0.10% (w/v), at pH 4.5-7.5.

In an embodiment the liquid pharmaceutical composition of the invention comprises 40-60 mg/mL of the monoclonal anti-alpha synuclein antibody, GM37v2, 20-30 mM histidine buffer, 90-110 mM sodium chloride (NaCl), 90-110 mM sucrose and polysorbate 80 (tween 80) in an amount of between 0.01% to 0.03% (w/v), at pH 5.5-6.5.

In an embodiment the liquid pharmaceutical composition of the invention comprises 53 mg/mL of the monoclonal anti-alpha synuclein antibody, GM37v2, 25 mM histidine buffer, 100 mM sodium chloride (NaCl), 100 mM sucrose and polysorbate 80 (tween 80) in an amount of 0.02% (w/v), at pH 6.0.

In an embodiment the liquid pharmaceutical composition of the invention comprises 53 mg/mL of the monoclonal anti-alpha synuclein antibody, GM37v2, 25 mM histidine buffer, 100 mM sodium chloride (NaCl), 100 mM sucrose and polysorbate 80 (tween 80) in an amount of 0.02% (w/v), at pH 6.0 or within +/−30% of said values, such as +/−25%, such as +/−20%, such as +/−15%, such as +/−10%, such as +/−5%, such as +/−1%, such as +/−0.5%, such as +/−0.25% or such as +/−0.1%.

In certain embodiments the liquid pharmaceutical composition of the invention is presented in vials of 20 mL volume, wherein each vial contains about 1000-1060 mg of GM37v2, such as about 1060 mg.

Synucleinopathies and Prodromal Synucleinopathies

Synucleinopathies, refer to disorders characterized by the neural inclusion of pathologic alpha synuclein aggregates called Lewy bodies. Synucleinopathies include Parkinson's disease (PD) (including idiopathic and inherited forms of Parkinson's disease) and Diffuse Lewy Body (DLB) disease (also known as Dementia with Lewy Bodies (DLB), Lewy body variant of Alzheimer's disease (LBV), Combined Alzheimer's and Parkinson disease (CAPD), pure autonomic failure (PAF) and multiple system atrophy (MSA; e.g., Olivopontocerebellar Atrophy, Striatonigral Degeneration and Shy-Drager Syndrome)).

In one aspect the present invention provides suitable dosage regimens for treating synucleinopathies, such as Parkinson's disease (PD) (including idiopathic and inherited forms of Parkinson's disease), Gauchers Disease (GD), Diffuse Lewy Body Disease (DLBD), Dementia with Lewy Bodies (DLB), Lewy body variant of Alzheimer's disease (LBV), Combined Alzheimer's and Parkinson's disease, pure autonomic failure and multiple system atrophy (MSA). In preferred embodiments the synucleinopathy is PD. In another preferred embodiment the synucleinopathy is DLB. In yet another preferred embodiment the synucleinopathy is MSA.

In another aspect the present invention provides suitable dosage regimens for treating prodromal synucleinopathies in a human subject in risk of developing synucleinopathy being identifiable by exhibiting one or more clinical markers of prodromal synucleinopathies. Such clinical markers of prodromal synucleinopathies may be selected from REM Sleep Behaviour Disorder (RBD) such as isolated RBD (iRBD), dysfunctional olfaction such as hyposmia, abnormal cognitive performance in neuropsychological testing, subtle motor dysfunction or abnormal motor performance assessed by objective testing, abnormal color vision, autonomic dysfunctions (such as constipation, urinary symptoms, erectile dysfunction, orthostatic hypotension), reduced nigrostriatal dopaminergic binding in the putamen and striatum (abnormal DAT-SPECT), Seborrhoeic dermatitis, and a genotype associated with increasing phenoconversion risk such as mutations in glucocerebrosidase (encoded by the GBA gene).

In some embodiments of these aspects, the human subject is identified as having signs of synucleinopathies or prodromal synucleinopathies in the form of abnormal accumulation or deposition of alpha synuclein in the central nervous system. In certain embodiments, the human subject is identified by in vivo imaging of alpha synuclein (e.g. in the brain) by a method comprising positron emission tomography (PET), single photon emission tomography (SPECT), near infrared (NIR) optical imaging, magnetic resonance imaging (MRI), dopamine transporter (DAT) imaging, or substantia nigra ultrasonography.

In some embodiments, the human subject is identified as having signs of synucleinopathies or prodromal synucleinopathies by assaying the level of alpha synuclein in a blood, plasma, or cerebrospinal fluid (CSF) sample obtained from the subject and comparing the assayed level of alpha synuclein in the subject to a reference standard, wherein the difference or similarity between the level of alpha synuclein in the blood, plasma, or CSF sample and the reference standard correlates with the level of alpha synuclein in the brain of the subject. The level of alpha synuclein may be assessed by methods known in the art comprising, e.g., analyzing alpha synuclein by one or more techniques chosen from Western blot, immunoprecipitation, enzyme-linked immunosorbent assay (ELISA), radioimmunoassay (RIA), fluorescent activated cell sorting (FACS), two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), and laser densitometry.

In some embodiments the human subject has been identified by having symptoms of synucleinopathies or prodromal synucleinopathies via acknowledged methods and criteria in the field.

Recently new diagnostic criteria for MSA "The Movement Disorder Society Criteria for the Diagnosis of Multiple System Atrophy" was published by Wenning et al. which is hereby incorporated by reference (Wenning et al., Movement Disorders, 2022, Volume 37, Issue 6, Pages 1131-1148). These new criteria describe "Research criteria for possible prodromal MSA" which may be used to identify a patient with prodromal synucleinopathy, as shown in the table below:

| | |
|---|---|
| Essential features | A sporadic, progressive adult (>30 years) onset disease |
| Clinical non-motor features (entry criteria) | At least one of the following: RBD (polysomnography proven) Neurogenic OH (≥20/10 mmHg blood pressure drop) within 10 minutes of standing or head-up tilt Urogenital failure (erectile dysfunction in males below age of 60 years combined with at least one of unexplained voiding difficulties with post-void urinary residual volume >100 ml and unexplained urinary urge incontinence) |
| Clinical motor features | At least one of the following: Subtle parkinsonian signs Subtle cerebellar signs |
| Exclusion criteria | Absence Exclusion criteria |

At least one of unexplained anosmia on olfactory testing or abnormal cardiac sympathetic imaging ($^{123}$I-MIBG-scintigraphy)
Fluctuating cognition with pronounced variation in attention and alertness and early decline in visuoperceptual abilities
Recurrent visual hallucinations not induced by drugs within 3 years of disease onset
Dementia according to DSM-V within 3 years of disease onset
Downgaze supranuclear gaze palsy or slowing of vertical saccades
Brain MRI findings suggestive of an alternative diagnosis (eg, PSP, multiple sclerosis, vascular parkinsonism, symptomatic cerebellar disease, etc.)
Documentation of an alternative condition (MSA look-alike, including genetic or symptomatic ataxia and parkinsonism) known to produce autonomic failure, ataxia, or parkinsonism and plausibly connected to the patient's symptoms Abbreviations: MSA, multiple system atrophy; RBD, rapid eye movement sleep behavior disorder; OH, orthostatic hypotension; DSM-V, Diagnostic and Statistical Manual of Mental Disorders, Fifth Edition; MRI, magnetic resonance imaging; PSP, progressive supranuclear palsy.

Parkinson's Disease (PD)

Parkinson's Disease (PD) is a synucleinopathy disorder. There are no well-defined diagnostic criteria for PD, however, there are various symptoms and diagnostic tests that can be used in combination to support a PD diagnosis. Making an accurate diagnosis of Parkinson's, particularly in its early stages, is difficult, but a skilled practitioner can come to a reasoned conclusion that the human subject suffers from PD by using clinical assesment tools. In some embodiments the PD diagnosis may be based on the presence of at least two of the four main symptoms of PD:
 a) Shaking or tremor
 b) Slowness of movement, called bradykinesia
 c) Stiffness or rigidity of the arms, legs or trunk
 d) Trouble with balance and possible falls, also called postural instability.

Imaging techniques such as MRI, ultrasound of the brain, PET scans, and/or specific single-photon emission computerized tomography (SPECT) scan e.g. to analyse dopamine transport (DaTscan) may also be useful in supporting the diagnosis of PD.

Dementia with Lewy Bodies (DLB)

Dementia with Lewy bodies is a type of synucleinopathy that involves progressive dementia that leads to a decline in thinking, reasoning and independent function. Dementia with Lewy bodies is often hard to diagnose because its early symptoms may resemble those of Alzheimer's disease or a psychiatric illness. There are no definitive diagnostic criteria but some core clinical symptoms of DLB are Dementia, Movement problems/parkinsonism, Cognitive fluctuations, Visual hallucinations and REM sleep behavior disorder. Some supportive clinical symptoms are Extreme sensitivity to antipsychotic medications, Falls or fainting, Severe problems with involuntary functions (maintaining blood pressure, incontinence, constipation, loss of smell), Changes in personality and mood (depression, apathy, anxiety).

A diagnosis of Lewy body dementia requires a progressive decline in ability to think, as well as at least two of the following:
a) Fluctuating alertness and thinking function
b) Repeated visual hallucinations
c) Parkinsonian symptoms
d) REM sleep behaviour disorder Autonomic dysfunction, which involves instability in blood pressure and heart rate, poor regulation of body temperature, sweating, and related signs and symptoms, further supports a Lewy body dementia diagnosis, and so does sensitivity to antipsychotic drugs.

Physical and neurological examinations and various tests can help distinguish DLB from other illnesses and support the diagnosis of DLB. Such specific test can be positron emission tomography (PET) scan or a single-photon emission computerized tomography (SPECT) scan showing reduced dopamine transporter (DAT) uptake in the basal ganglia (brain region), Abnormal $^{123}$iodine-MIBG myocardial scintigraphy showing reduced communication of cardiac nerves or Sleep study confirming REM sleep behaviour disorder without loss of muscle tone.

Multiple System Atrophy (MSA)

Multiple system atrophy (MSA) is the most rapidly progressive of the synucleinopathies, a group of disorders characterized by the abnormal deposition of the protein alpha synuclein in the central and peripheral autonomic nervous system. In the present context the term MSA is meant to refer to all types of MSA such as the multiple system atrophy parkinsonian type (MSA-P) or multiple system atrophy cerebellar type (MSA-C). MSA is sometimes denoted as Olivopontocerebellar Atrophy, progressive autonomic failure with multiple system atrophy, Striatonigral Degeneration or Shy-Drager Syndrome. The present invention provides dosage regimens for the treatment of MSA in all stages of disease progression including prodromal, early, moderate and advanced stages and all stages between.

Diagnosing multiple system atrophy (MSA) can be challenging as certain signs and symptoms of MSA, such as muscle rigidity and unsteady gait, also occur with other disorders, such as Parkinson's disease. A proper clinical examination, with various autonomic tests and imaging studies, may assist in determining whether the diagnosis is probable MSA or possible MSA. Examples of clinical methods which can be useful in supporting the MSA diagnosis of patients with suspected MSA is structural and functional brain imaging, cardiac sympathetic imaging, cardiovascular autonomic testing, olfactory testing, sleep study, urological evaluation, and dysphagia, cognitive assessments, skin biopsy, retinal biomarkers, blood and/or cerebrospinal fluid biomarkers, and genetic testing. Diagnosis of possible or probable MSA can for example be facilitated by the so-called Gilman criteria (Gilman et al., Neurology. 2008 Aug. 26; 71(9): 670-676).

In some embodiments the human subject to be treated has probable MSA, which may be identifiable by:

a) Autonomic failure involving urinary incontinence or an orthostatic decrease of blood pressure within 3 min of standing by at least 30 mmHg systolic or 15 mmHg diastolic; and
b) Poorly levodopa-responsive parkinsonism (bradykinesia with rigidity, tremor or postural instability); or
c) A cerebellar syndrome (gait ataxia with cerebellar dysarthria, limb ataxia or cerebellar oculomotor dysfunction).

In some embodiments the human subject to be treated has possible MSA, which may be identifiable by:
a) Parkinsonism (bradykinesia with rigidity tremor or postural instability); or
b) Cerebellar syndrome (gait ataxia with cerebellar dysarthria limb ataxia or cerebellar oculomotor dysfunction); and
c) At least one feature suggesting autonomic dysfunction (otherwise unexplained urinary urgency frequency or incomplete bladder emptying erectile dysfunction in males or significant orthostatic blood pressure decline that does not meet the level required in probable MSA); and
d) At least one of the following features:

For Possible MSA-P or MSA-C:
i. Babinski sign with hyperreflexia
ii. Stridor

For Possible MSA-P:
iii. Rapidly progressive parkinsonism
iv. Poor response to levodopa
v. Postural instability within 3 years of motor onset
vi. Gait ataxia, cerebellar dysarthria, limb ataxia, or cerebellar oculomotor dysfunction
vii. Dysphagia within 5 year of motor onset
viii. Atrophy on MRI of putamen middle cerebellar peduncle, pons or cerebellum
ix. Hypometabolism on fluorodeoxyglucose positron emission tomography (FDG-PET) in putamen, brainstem or cerebellum For Possible MSA-C:
x. Parkinsonism (bradykinesia and rigidity)
xi. Atrophy on MRI of putamen, middle cerebellar peduncle, or pons
xii. Hypometabolism on FDG-PET in putamen
xiii. Presynaptic nigrostriatal dopaminergic denervation on single photon emission computed tomography (SPECT) or PET.

Currently, a definite MSA diagnosis can only be confirmed post-mortem by examination of:
a) Widespread and abundant cerebral alpha synuclein-positive glial cytoplasmic inclusions; and/or
b) Neurodegenerative changes in striatonigral or olivopontocerebellar region.

Recently new diagnostic criteria for MSA "The Movement Disorder Society Criteria for the Diagnosis of Multiple System Atrophy" was published by Wenning et al. (Wenning et al., Movement Disorders, 2022, Volume 37, Issue 6, Pages 1131-1148).

These criteria include diagnosis of clinically established MSA and clinically probable MSA, as shown in the table below:

| | Division into clinically established MSA-P or MSA-C according to predominant motor syndrome | |
|---|---|---|
| Essential features | A sporadic, progressive adult (>30 years) onset disease | |
| | Clinically established MSA | Clinically probable MSA |
| Core clinical features | 1. Autonomic dysfunction defined as (at least one is required) | At least two of: 1. Autonomic dysfunction defined as (at least one is required): |

| Division into clinically established MSA-P or MSA-C according to predominant motor syndrome | | |
|---|---|---|
| | Unexplained voiding difficulties with post-void urinary residual volume ≥100 mL<br>Unexplained urinary urge incontinence<br>Neurogenic OH (≥20/10 mmHg blood pressure drop) within 3 minutes of standing or head-up tilt test<br>and at least one of<br>1. Poorly L-dopa-responsive parkinsonism<br>2. Cerebellar syndrome (at least two of gait ataxia, limb ataxia, cerebellar dysarthria, or oculomotor features) | Unexplained voiding difficulties with post-void urinary residual volume<br>Unexplained urinary urge incontinence<br>Neurogenic OH (≥20/10 mmHg blood pressure drop) within 10 minutes of standing or head-up tilt test<br>2. Parkinsonism<br>3. Cerebellar syndrome (at least one of gait ataxia, limb ataxia, cerebellar dysarthria, or oculomotor features) |
| Supportive clinical (motor or non-motor) features | At least two | At least one[a] |
| MRI marker | At least one | Not required |
| Exclusion criteria | Absence | Absence |

Supportive clinical features

| Supportive motor features | Rapid progression within 3 years of motor onset<br>Moderate to severe postural instability within 3 years of motor onset<br>Craniocervical dystonia induced or exacerbated by L-dopa in the absence of limb dyskinesia<br>Severe speech impairment within 3 years of motor onset<br>Severe dysphagia within 3 years of motor onset<br>Unexplained Babinski sign<br>Jerky myoclonic postural or kinetic tremor<br>Postural deformities | Supportive non-motor features | Stridor<br>Inspiratory sighs<br>Cold discolored hands and feet<br>Erectile dysfunction (below age of 60 years for clinically probable MSA)<br>Pathologic laughter or crying |
|---|---|---|---|

MRI markers of clinically established MSA
Each affected brain region as evidenced by either atrophy or increased diffusivity counts as one MRI marker.

| For MSA-P | For MSA-C |
|---|---|
| Atrophy of:<br>Putamen (and signal decrease on iron-sensitive sequences)<br>Middle cerebellar peduncle<br>pons<br>Cerebellum<br>"Hot cross bun" sign<br><br>Increased diffusivity of:<br>Putamen<br>Middle cerebellar peduncle | Atrophy of:<br>Putamen (and signal decrease on iron-sensitive sequences)<br>Infratentorial structures (pons and middle cerebellar peduncle)<br>"Hot cross bun" sign<br><br>Increased diffusivity of:<br>Putamen |

| Division into clinically established MSA-P or MSA-C according to predominant motor syndrome |
| --- |
| Exclusion criteria |

Substantial and persistent beneficial response to dopaminergic medications
Unexplained anosmia on olfactory testing
Fluctuating cognition with pronounced variation in attention and alertness and early decline in visuoperceptual abilities
Recurrent visual hallucinations not induced by drugs within 3 years of disease onset
Dementia according to DSM-V within 3 years of disease onset
Downgaze supranuclear palsy or slowing of vertical saccades
Brain MRI findings suggestive of an alternative diagnosis (eg, PSP, multiple sclerosis, vascular parkinsonism, symptomatic cerebellar disease, etc.)
Documentation of an alternative condition (MSA look-alike, including genetic or symptomatic ataxia and parkinsonism) known to produce autonomic failure, ataxia, or parkinsonism and plausibly connected to the patient's symptoms

[a]Excluding erectile dysfunction as an isolated feature.
Abbreviations: MSA, multiple system atrophy; MSA-P, MSA-parkinsonian type; MSA-C, MSA-cerebellar type; OH, orthostatic hypotension; MRI, magnetic resonance imaging; DSM-V, Diagnostic and Statistical Manual of Mental Disorders, Fifth Edition; PSP, progressive supranuclear palsy.

REM Sleep Behaviour Disorder (RBD)

Rapid eye movement (REM) sleep behavioral disorder (RBD) is considered to be an early manifestation of synucleinopathy. REM Sleep Behavior Disorder (RBD) is characterized by "acting out" of dreams and is diagnosed by video-polysomnography (vPSG) demonstrating a loss of muscle atonia that normally accompanies REM sleep. REM Sleep Behavior Disorder (RBD), such as clinically Isolated RBD (iRBD) (previously sometimes referred to as idiopathic RBD), is the most reliable clinical marker of prodromal synucleinopathies, a group of neurodegenerative disorders including Parkinson's disease (PD), Dementia with Lewy Bodies (DLB) and Multiple System Atrophy (MSA). The vast majority of individuals with REM Sleep Behavior Disorder (RBD), such as iRBD are diagnosed with a synucleinopathy within 20 years of onset of iRBD, such as within 3 years, within 5 years, within 8 years or within 16 years. Therefore, the REM Sleep Behavior Disorder (RBD) populations can serve as an ideal group for administering the antibodies for use according to the invention to modify synuclein-specific neurodegeneration progression, i.e. to obtain a disease-modifying treatment that delays or prevent phenoconversion to an overt synucleinopathy.

RBD diagnosis may be based on certain consensus criteria, such as the ones established by the International Classification of Sleep Disorders (ICSD-3), or the Diagnostic and Statistical Manual of Mental Disorders 5th edition (DSM-V), or the American Academy of Sleep Medicine (AASM) Manual for the Scoring of Sleep and Associated Events. A confirmatory RBD diagnosis may require confirmation by vPSG analysis. RBD diagnosis may be further supported by assessment using varoius imaging techniques which are also useful to identify synucleinopathies such as positron emission tomography (PET), single photon emission tomography (SPECT), near infrared (NIR) optical imaging, magnetic resonance imaging (MRI), dopamine transporter (DAT) imaging, or substantia nigra ultrasonography.

Unified Multiple System Atrophy Rating Scale (UMSARS)

The UMSARS is a well-known combined clinician and patient/caregiver-reported scale to assess disease progression in patients with MSA. The UMSARS scale can be used in clinical settings to assess MSA patients both for monitoring disease progression and/or to quantify treatment response.

The UMSARS Consists of Four Parts:

Part I assesses historical information on symptoms and activities of daily living over the past two weeks as reported by patients and caregivers (12 items) rated on a scale ranging from 0=not affected to 4=unable to do the activity (Note; each item uses different anchor descriptors as relevant to the question addressed).

Part II consist of a clinical examination of key MSA motor signs and symptoms (14 items) rated on a scale ranging from 0=normal to 4=marked/severe impairment (Note; each item uses different anchor descriptors as relevant to the question addressed).

Part III includes an autonomic examination (4 items), individual measures of systolic and diastolic blood pressure, heart rate and orthostatic symptoms (yes/no).

Part IV assess global disability (1 item) ranging on a scale from 1=completely independent to 5=totally dependent and helpless/bedridden.

The total UMSARS score (UMSARS TS) is obtained by the sum of the items from Part I and Part II. Part I scores range between 0 to 48, and Part II scores range between 0 and 56. A higher score indicates greater impairment. An experienced neurologist can use the UMSARS after a short training session.

The modified UMSARS (mUMSARS) score in the present context consist of UMSARS Part 1 where the response option scores of 0 and 1 will be collapsed to one category in the analysis.

The abbreviated UMSARS (aUMSARS) score can be derived from a subset of items from UMSARS Part I and Part II shown to be patient centric and sensitive to progression in MSA. Abbreviated UMSARSs can be developed to be patient centric (relevant to patients) and sensitive to detect change in patients diagnosed with possible MSA, probable MSA, clinically established MSA or clinically probable MSA. The abbreviated UMSARS score is based on a subset of items from Part I and Part II in the original UMSARS scale. The items to be included in the aUMSARS score can for example be identified by 1) Finding items that are sensitive to change based on slopes and/or Patient centric/focused based on correlations with QoL scales, 2) Combining them into an abbreviated version of the UMSARS; i.e by excluding items with low patient centricity/focus and with low ability to detect change over time. Data used to develop the aUMSARS can for example be taken from the European MSA study group natural history study and the MSA-Ras trial. Sensitivity of change of a sub-item of the Unified MSA Rating Scale can be assessed by calculation of a sensitivity to change ratio using its mean slope of progression divided by the standard deviation of the slope when modelling its progression over time with a Linear Mixed Model. Patient-centricity can be assessed on the basis of correlation of Unified MSA Rating Scale items with quality of life measures.

An example of such aUMSARS is presented below and this specific aUMSARS include the following 19 Part I and Part II UMSARS items:

| Part 1 | |
|---|---|
| Swallowing | P1 Q2 |
| Handwriting | P1 Q3 |
| Dressing | P1 Q5 |
| Hygiene | P1 Q6 |
| Walking | P1 Q7 |
| Orthostatic symptoms | P1 Q9 |
| Urinary symptoms | P1 Q10 |
| Bowel function | P1 Q12 |
| Part 2 | |
| Facial expression | P2 Q1 |
| Ocular motor dysfunction | P2 Q3 |
| Action tremor | P2 Q5 |
| Increased tone | P2 Q6 |
| Rapid alternating movement hands | P2 Q7 |
| Finger taps | P2 Q8 |
| Leg agility | P2 Q9 |
| Heel-knee-shin test | P2 Q10 |
| Arising from chair | P2 Q11 |
| Posture | P2 Q12 |
| Gait | P2 Q14 |

SPECIFIC EMBODIMENTS

The following embodiments describes the invention in further detail.

In one embodiment the invention provides a monoclonal alpha synuclein antibody for use in the treatment of synucleinopathies or prodromal synucleinopathies, wherein the use comprises administering a monoclonal alpha synuclein antibody intravenously to a human subject suffering from synucleinopathy or in risk of developing synucleinopathy, at a dose of more than 700 mg and less than 7000 mg, such as between 900 mg to 5000 mg, or such as between 1000 mg to 4500 mg, and wherein the monoclonal alpha synuclein antibody is a full-length antibody that binds an epitope within amino acids 112-117 (SEQ ID NO:9 (ILEDMP)) of human alpha synuclein (SEQ ID NO:10).

In one embodiment the invention provides a monoclonal-alpha synuclein antibody for use in the treatment of synucleinopathies, wherein the use comprises administering a monoclonal alpha synuclein antibody intravenously to a human subject suffering from synucleinopathy or in risk of developing synucleinopathy, at a dose of more than 700 mg and less than 7000 mg, such as between 900 mg to 5000 mg, or such as between 1000 mg to 4500 mg, and wherein the monoclonal alpha synuclein antibody is a full-length antibody that binds an epitope within amino acids 112-117 (SEQ ID NO:9 (ILEDMP)) of human alpha synuclein (SEQ ID NO:10).

In one embodiment the invention provides a monoclonal alpha synuclein antibody for use in the treatment of prodromal synucleinopathies, wherein the use comprises administering a monoclonal alpha synuclein antibody intravenously to a human subject suffering from synucleinopathy or in risk of developing synucleinopathy, at a dose of more than 700 mg and less than 7000 mg, such as between 900 mg to 5000 mg, or such as between 1000 mg to 4500 mg, and wherein the monoclonal alpha synuclein antibody is a full-length antibody that binds an epitope within amino acids 112-117 (SEQ ID NO:9 (ILEDMP)) of human alpha synuclein (SEQ ID NO:10).

In certain embodiments the monoclonal anti-alpha synuclein antibody has an estimated KD value of binding to the oligomeric form of alpha synuclein of about 0.5 nM.

In a further embodiment the monoclonal alpha synuclein antibody has a KD value of binding to the monomeric form of alpha synuclein of about 36 nM.

In a further embodiment the monoclonal alpha synuclein antibody has a KD value of binding to the monomeric form of alpha synuclein of about 36 nM, and an estimated binding to the oligomeric form of alpha synuclein of about 0.5 nM.

In one embodiment, the ratio between the monomeric and oligomeric binding values is approximately 65 fold enhanced to the oligomeric form as compared to the monomeric form.

In a further embodiment the monoclonal alpha synuclein antibody has a human T½ of about 25-35 days, such as about 4 weeks, such as about 27-33 days, such as 28-32 days, such as 28-30 days, such as 28 days, such as 29 days, such as 30 days.

In a further embodiment the monoclonal alpha synuclein antibody has a KD value of binding to the monomeric form of alpha synuclein of about 36 nM, and an estimated binding to the oligomeric form of alpha synuclein of 0.5 nM, such that the ratio between the monomeric and oligomeric binding is approximately 65 fold enhancement.

In a further embodiment the monoclonal alpha synuclein antibody has a KD value of binding to the monomeric form of alpha synuclein of about 36 nM, and an estimated Kd value of binding to the oligomeric form of alpha synuclein of 0.5 nM, such that the ratio between the monomeric and oligomeric binding is approximately 65 fold enhancement, and the antibody has a T½ of about 28-30 days, such as 29 days.

In a further embodiment the monoclonal alpha synuclein antibody comprises:
    a. a Heavy Chain CDR1 having the amino acid sequence of SEQ ID NO:1;
    b. a Heavy Chain CDR2 having the amino acid sequence of SEQ ID NO:2;
    c. a Heavy Chain CDR3 having the amino acid sequence of SEQ ID NO:3;
    d. a Light Chain CDR1 having the amino acid sequence of SEQ ID NO:4;
    e. a Light Chain CDR2 having the amino acid sequence of SEQ ID NO:5; and
    f. a Light Chain CDR3 having the amino acid sequence of SEQ ID NO:6.

In a further embodiment the monoclonal alpha synuclein antibody comprises a heavy chain consisting of a variable domain of SEQ ID NO:7 and a light chain consisting of a variable domain of SEQ ID NO:8.

In a further embodiment the monoclonal alpha synuclein antibody comprises:
    a. a Heavy Chain CDR1 having the amino acid sequence of SEQ ID NO:1;
    b. a Heavy Chain CDR2 having the amino acid sequence of SEQ ID NO:33;
    c. a Heavy Chain CDR3 having the amino acid sequence of SEQ ID NO:3;

d. a Light Chain CDR1 having the amino acid sequence of SEQ ID NO:4;
e. a Light Chain CDR2 having the amino acid sequence of SEQ ID NO:5; and
f. a Light Chain CDR3 having the amino acid sequence of SEQ ID NO:6.

In a further embodiment the monoclonal alpha synuclein antibody comprises a heavy chain consisting of a variable domain of SEQ ID NO:30 and a light chain consisting of a variable domain of SEQ ID NO:8.

In a further embodiment the monoclonal alpha synuclein antibody comprises:
a. a Heavy Chain CDR1 having the amino acid sequence of SEQ ID NO:1;
b. a Heavy Chain CDR2 having the amino acid sequence of SEQ ID NO:34;
c. a Heavy Chain CDR3 having the amino acid sequence of SEQ ID NO:3;
d. a Light Chain CDR1 having the amino acid sequence of SEQ ID NO:4;
e. a Light Chain CDR2 having the amino acid sequence of SEQ ID NO:5; and
f. a Light Chain CDR3 having the amino acid sequence of SEQ ID NO:6.

In a further embodiment the monoclonal alpha synuclein antibody comprises a heavy chain consisting of a variable domain of SEQ ID NO:31 and a light chain consisting of a variable domain of SEQ ID NO:8.

In a further embodiment the monoclonal alpha synuclein antibody comprises:
a. a Heavy Chain CDR1 having the amino acid sequence of SEQ ID NO:1;
b. a Heavy Chain CDR2 having the amino acid sequence of SEQ ID NO:35;
c. a Heavy Chain CDR3 having the amino acid sequence of SEQ ID NO:3;
d. a Light Chain CDR1 having the amino acid sequence of SEQ ID NO:4;
e. a Light Chain CDR2 having the amino acid sequence of SEQ ID NO:5; and
f. a Light Chain CDR3 having the amino acid sequence of SEQ ID NO:6.

In a further embodiment the monoclonal alpha synuclein antibody comprises a heavy chain consisting of a variable domain of SEQ ID NO:32 and a light chain consisting of a variable domain of SEQ ID NO:8.

In a further embodiment the monoclonal alpha synuclein antibody is a full-length human antibody.

In a further embodiment the monoclonal alpha synuclein antibody is a human IgG1 antibody.

In a further embodiment the monoclonal alpha synuclein antibody is GM37.

In a further embodiment the monoclonal alpha synuclein antibody is GM37 variant 1.

In a further embodiment the monoclonal alpha synuclein antibody is GM37 variant 2.

In a further embodiment the monoclonal alpha synuclein antibody is GM37 variant 3.

In a further embodiment the monoclonal alpha synuclein antibody further comprises a constant heavy chain domain as defined in SEQ ID NO:18 and a kappa light chain constant domain as defined in SEQ ID NO:17.

In a further embodiment the monoclonal alpha synuclein antibody is administered every 4 weeks or 28 days.

In a further embodiment the monoclonal alpha synuclein antibody is administered once monthly.

In a further embodiment the monoclonal alpha synuclein antibody is administered at a dose of more than 700 mg and less than 7000 mg, such as between 900 mg to 5000 mg, or such as between 1000 mg to 4500 mg, at intervals of 3-5 weeks.

In a further embodiment the monoclonal alpha synuclein antibody is administered at a dose of 750 mg, 2250 mg, or 4500 mg.

In a further embodiment the monoclonal alpha synuclein antibody is administered at a dose of 1000 mg to 4500 mg, such as between 2000 mg to 4500 mg, or between 3500 mg to 4500 mg.

In a further embodiment the monoclonal alpha synuclein antibody is administered at a dose of 750 mg, 1050 mg, 1400 mg, 1750 mg, 2100 mg, 2450 mg, 2800 mg, 3150 mg, 3500 mg, 3850 mg, 4200 mg, 4550 mg, 4900 mg, 5250 mg, 5600 mg, 5950 mg, 6300 mg, or 6650 mg.

In a further embodiment the monoclonal alpha synuclein antibody is administered at a dose of 1050 mg, 2100 mg or 4200 mg.

In a further embodiment the monoclonal alpha synuclein antibody is administered at a dose 4200 mg.

In one embodiment, the dose is a fixed dose.

In a further embodiment the monoclonal alpha synuclein antibody is administered at a dose of 1050 mg, 2100 mg or 4200 mg every 28-30 days.

In a further embodiment the monoclonal alpha synuclein antibody is administered at a dose of 4200 mg every 4 weeks or every 28-30 days, such as every 28 days, every 29 days or every 30 days.

In a further embodiment the monoclonal alpha synuclein antibody is administered by intravenous infusion over 30 minutes ±10 minutes.

In a further embodiment the monoclonal alpha synuclein antibody is administered by intravenous infusion over 15 minutes ±5 minutes.

In a further embodiment the monoclonal alpha synuclein antibody is administered by intravenous infusion at a speed of between 25 mg/min to 300 mg/min.

In a further embodiment the monoclonal alpha synuclein antibody is administered by intravenous infusion at a speed of between 30 mg/min to 150 mg/min, such as 35 mg/min, 70 mg/min or 140 mg/min.

In a further embodiment the monoclonal alpha synuclein antibody is administered by intravenous infusion at a speed of between 60 mg/min to 300 mg/min, such as 70 mg/min, 140 mg/min or 280 mg/min.

In a further embodiment the monoclonal alpha synuclein antibody is administered in an amount and a frequency sufficient to achieve an estimated CSF mean steady state concentration of the antibody of at least 0.5 nM, such as at least 1 nM, such as at least 2 nM, such as at least 3 nM, such as at least 6 nM, or such as at least 12 nM.

In a further embodiment the monoclonal alpha synuclein antibody is administered in an amount and a frequency sufficient to achieve an estimated CSF mean steady state concentration of the antibody of at least 3 nM.

In a further embodiment the monoclonal alpha synuclein antibody is administered in an amount and a frequency sufficient to achieve an estimated CSF mean steady state concentration of the antibody of at least 6 nM.

In a further embodiment the monoclonal alpha synuclein antibody is administered in an amount and a frequency sufficient to achieve an estimated CSF mean steady state concentration of the antibody of at least 12 nM.

In a further embodiment the monoclonal alpha synuclein antibody is administered in an amount and a frequency sufficient to achieve an estimated target engagement to oligomeric forms of alpha synuclein in CSF of at least 50%, such as at least 60%, such as at least 75%, such as at least 80%, such as at least 85%, such as at least 90%, such as at least 95%, or such as at least 99%.

In a further embodiment the monoclonal alpha synuclein antibody is administered in an amount and a frequency sufficient to achieve an estimated target engagement to oligomeric forms of alpha synuclein in CSF of at least 85%.

In a further embodiment the monoclonal alpha synuclein antibody is administered in an amount and a frequency sufficient to achieve an estimated target engagement to oligomeric forms of alpha synuclein in CSF of at least 90%.

In a further embodiment the monoclonal alpha synuclein antibody is administered in an amount and a frequency sufficient to achieve an estimated target engagement to oligomeric forms of alpha synuclein in CSF of at least 95%.

In a further embodiment the synucleinopathy to be treated is selected from the list consisting of: Parkinson's disease (PD) (including idiopathic and inherited forms of Parkinson's disease), Gauchers Disease (GD), Diffuse Lewy Body Disease (DLBD), Dementia with Lewy Bodies (DLB), Lewy body variant of Alzheimer's disease (LBV), Combined Alzheimer's and Parkinson's disease, pure autonomic failure and multiple system atrophy (MSA).

In a further embodiment the synucleinopathy to be treated is selected from: Parkinson's disease (PD), Dementia with Lewy Bodies (DLB), or multiple system atrophy (MSA).

In a further embodiment the synucleinopathy to be treated is multiple system atrophy (MSA) or a MSA subtype selected from: possible MSA, probable MSA, MSA type C, MSA type P, clinically established MSA or clinically probable MSA.

In a further embodiment the synucleinopathy to be treated is selected from: Parkinson's disease (PD) (including idiopathic and inherited forms of Parkinson's disease), Gauchers Disease (GD), Diffuse Lewy Body Disease (DLBD), Dementia with Lewy Bodies (DLB), Lewy body variant of Alzheimer's disease (LBV), Combined Alzheimer's and Parkinson's disease, pure autonomic failure and multiple system atrophy (MSA), and the treatment comprising administering to a patient the monoclonal alpha synuclein antibody in an amount and a frequency sufficient to achieve a CSF steady state concentration of the antibody of at least 0.5 nM, such as at least 1 nM, such as at least 2 nM, such as at least 3 nM, such as at least 6 nM, or such as at least 12 nM.

In a further embodiment the synucleinopathy to be treated is selected from: Parkinson's disease (PD) (including idiopathic and inherited forms of Parkinson's disease), Gauchers Disease (GD), Diffuse Lewy Body Disease (DLBD), Dementia with Lewy Bodies (DLB), Lewy body variant of Alzheimer's disease (LBV), Combined Alzheimer's and Parkinson's disease, pure autonomic failure and multiple system atrophy (MSA), and the treatment comprising administering to a patient the monoclonal alpha synuclein antibody in an amount and a frequency sufficient to achieve a CSF steady state concentration of the antibody of at least 3 nM, such as at least 6 nM, or such as at least 12 nM.

In a further embodiment the invention provides a method of treating a synucleinopathy selected from: Parkinson's disease (PD) (including idiopathic and inherited forms of Parkinson's disease), Gauchers Disease (GD), Diffuse Lewy Body Disease (DLBD), Dementia with Lewy Bodies (DLB), Lewy body variant of Alzheimer's disease (LBV), Combined Alzheimer's and Parkinson's disease, pure autonomic failure and multiple system atrophy (MSA), where the treatment comprising administering to a patient the monoclonal alpha synuclein antibody in an amount and a frequency sufficient to achieve an estimated target engagement to oligomeric forms of alpha synuclein in CSF of at least 50%, such as at least 60%, such as at least 75%, such as at least 80%, such as at least 85%, such as at least 90%, such as at least 95%, or such as at least 99%.

In a further embodiment the invention provides a method of treating a synucleinopathy selected from: Parkinson's disease (PD) (including idiopathic and inherited forms of Parkinson's disease), Gauchers Disease (GD), Diffuse Lewy Body Disease (DLBD), Dementia with Lewy Bodies (DLB), Lewy body variant of Alzheimer's disease (LBV), Combined Alzheimer's and Parkinson's disease, pure autonomic failure and multiple system atrophy (MSA), where the treatment comprising administering to a patient the monoclonal alpha synuclein antibody in an amount and a frequency sufficient to achieve an estimated target engagement to oligomeric forms of alpha synuclein in CSF of at least 85%, such as at least 90%, such as at least 95%.

In a further embodiment the invention provides a method of treating a synucleinopathy selected from: Parkinson's disease (PD) (including idiopathic and inherited forms of Parkinson's disease), Gauchers Disease (GD), Diffuse Lewy Body Disease (DLBD), Dementia with Lewy Bodies (DLB), Lewy body variant of Alzheimer's disease (LBV), Combined Alzheimer's and Parkinson's disease, pure autonomic failure or multiple system atrophy (MSA).

In a further embodiment the invention provides a method of treating a synucleinopathy selected from: Parkinson's disease (PD), Dementia with Lewy Bodies (DLB), or multiple system atrophy (MSA).

In a further embodiment the invention provides a method of treating a synucleinopathy which is multiple system atrophy (MSA) such as a MSA subtype selected from: possible MSA, probable MSA, MSA type C, MSA type P, clinically established MSA or clinically probable MSA.

In a further embodiment the invention provides a monoclonal alpha synuclein antibody, for treating a human subject suffering from multiple system atrophy (MSA), which is identifiable by having been diagnosed with MSA of the multiple system atrophy parkinsonian type (MSA-P) or multiple system atrophy cerebellar type (MSA-C) subtype.

In a further embodiment the invention provides a monoclonal alpha synuclein antibody, treating a human subject suffering from multiple system atrophy (MSA), which is identifiable by having had onset of motor and/or autonomic (orthostatic or urinary) MSA symptoms within the last 5 years, such as within the last 4 years, or such as within the last 3 years, or such as within the last 2 years, or such as within the last year.

In a further embodiment the invention provides a monoclonal alpha synuclein antibody, for treating a human subject suffering from multiple system atrophy (MSA), which is identifiable by having an UMSARS Part I score <16 (omitting question 11 on sexual function).

In a further embodiment the invention provides a monoclonal alpha synuclein antibody, for treating a human subject suffering from multiple system atrophy (MSA), which is identifiable by having a cognitive performance evaluated by the Montreal Cognitive Assessment (MoCA) with a score >22.

In an embodiment the treatment of synucleinopathy consists of delaying disease progression.

In a further embodiment the treatment of synucleinopathy consists of delaying disease progression by at least 5%, such as at least 10%, such as at least 15%, such as at least 20%, such as at least 25%, such as at least 30%, such as at least 35%, such as at least 40%, such as at least 45%, such as at least 50%, such as at least 55%, such as at least 60%, such as at least 65%, such as at least 70%, such as at least 75%, such as at least 80%, such as at least 85% or such as at least 90%.

In a further embodiment the treatment of synucleinopathy consists of delaying disease progression by at least 25%, such as at least 30%, such as at least 35% or such as at least 40%.

In a further embodiment the treatment effect on synucleinopathy is observed following administration of at least 10 doses of the monoclonal alpha synuclein antibody, such as at least 11 doses, such as at least 12 doses, such as at least 13 doses, such as at least 14 doses, such as at least 15 doses, such as at least 16 doses, such as at least 17 doses, such as at least 18 doses, such as at least 19 doses or such as at least 20 doses.

In a further embodiment the treatment effect on synucleinopathy is observed following treatment with the monoclonal alpha synuclein antibody for at least 24 weeks, such as at least 48 weeks, such as at least 72 weeks or such as at least 96 weeks.

In a further embodiment the treatment effect on synucleinopathy is observed following treatment with the monoclonal alpha synuclein antibody for at least 44 weeks or at least 48 weeks.

In a further embodiment the treatment effect of synucleinopathy is observed following administration of at least 10 doses of the monoclonal alpha synuclein antibody, such as at least 11 doses or such as at least 12 doses.

In an embodiment the delay in disease progression is quantified by longitudinal changes from baseline in any of the relevant Unified Multiple System Atrophy Rating Scale (UMSARS) scores described herein or any relevant parts of these scales, such as Part I, Part II, Part III or Part IV or a change from baseline in any combination of these parts of the UMSARS.

In a further embodiment the delay in disease progression is quantified by longitudinal changes from baseline in the Unified Multiple System Atrophy Rating Scale (UMSARS) Part I and/or Part I or in the modified UMSARS Part I (mUMSARS) or in the abbreviated UMSARS (aUMSARS) scores.

In a further embodiment the delay in disease progression is quantified by longitudinal changes from baseline in the Unified Multiple System Atrophy Rating Scale (UMSARS) Part I or Part II scores.

In a further embodiment the delay in disease progression is quantified by longitudinal changes from baseline in the Unified Multiple System Atrophy Rating Scale (UMSARS) Part I and Part II scores.

In a further embodiment the delay in disease progression is quantified by longitudinal changes from baseline in the Unified Multiple System Atrophy Rating Scale (UMSARS) Part I, modified UMSARS Part I (mUMSARS) and/or UMSARS Part II scores.

In a further embodiment the delay in disease progression is quantified by longitudinal changes from baseline in UMSARS TS, UMSARS Part I, mUMSARS and/or UMSARS Part II scores.

In a further embodiment the delay in disease progression is quantified by longitudinal changes from baseline in an abbreviated UMSARS (aUMSARS) score.

In a further embodiment the delay in disease progression is quantified by longitudinal changes from baseline in the modified UMSARS (mUMSARS) score.

In a further embodiment the delay in disease progression is quantified by longitudinal changes from baseline in the total Unified Multiple System Atrophy Rating Scale (UMSARS TS) score.

In a further embodiment the delay in disease progression is quantified by longitudinal changes from baseline in Brain Volume, as measured by Volumetric MRI (vMRI).

In a further embodiment the delay in disease progression is quantified by longitudinal changes from baseline in Neurofilament Light Chain (NfL) blood concentrations.

In a further embodiment the delay in disease progression is quantified by longitudinal changes from baseline in one or more parameter selected from: Schwab and England Activities of Daily Living (SE-ADL) Score; as change from baseline in Clinical Global Impression—Severity of Illness (CGI-S) Score; as change from baseline in Patient Global Impression—Severity of Illness (PGI-S) Score; as change from baseline in Observer-Reported Global Impression—Severity of Illness (OGI-S) Score; as change from baseline in Composite Autonomic Symptom Score Select Change (COMPASS Select Change) Score; as change from baseline in UMSARS Part IV Score; as change from baseline in Speech, Swallowing, Falls, and Walking, as assessed by the UMSARS Part I Item Scores; as change from baseline in Frequency, Cause, and Consequence of Falls, as assessed by the Fall Diary Periods; as change from baseline in EuroQol 5-Dimension, 5-Level (EQ-5D-5L) Score; as change from baseline in Brain Volume, as Measured by Volumetric MRI (vMRI); as change from baseline in Tissue Integrity, as Measured by Diffusion-Tensor Imaging (DTI) MRI; as change from baseline in Neurofilament Light Chain (NfL) blood concentrations; as change from baseline in heart rate, blood pressure, and orthostatic symptoms, as assessed in UMSARS Part III; as change from baseline in gait parameters or frequency of falls, as assessed by digital wearable sensor-based devices that are capable of tracking relevant gait parameters and/or registering falls; as change from baseline in cerebral blood flow, as measured by arterial spin labelling (ASL) MRI; as change from baseline in t-tau and NfL CSF concentrations; or as change from baseline in concentration of pathological species of α-synuclein in CSF.

In a further embodiment the human subject in risk of developing synucleinopathy or suffering from prodromal synucleinopathy is identifiable by exhibiting one or more clinical markers of prodromal synucleinopathies selected from the group comprising: REM Sleep Behaviour Disorder (RBD) such as isolated RBD (iRBD), dysfunctional olfaction such as hyposmia, abnormal cognitive performance in neuropsychological testing, subtle motor dysfunction or abnormal motor performance assessed by objective testing, abnormal color vision, autonomic dysfunctions (such as constipation, urinary symptoms, erectile dysfunction, orthostatic hypotension), reduced nigrostriatal dopaminergic binding in the putamen and striatum (abnormal DAT-SPECT), Seborrhoeic dermatitis, and a genotype associated with increasing phenoconversion risk such as mutations in glucocerebrosidase (encoded by the GBA gene).

In a further embodiment the human subject in risk of developing synucleinopathy or suffering from prodromal synucleinopathy is identifiable by exhibiting RBD such as isolated RBD (iRBD), and at least one additional clinical marker of prodromal synucleinopathies, such as hyposmia and/or abnormal DAT-SPECT.

In a further embodiment the treatment of prodromal synucleinopathy consists of delaying disease onset.

In a further embodiment the treatment of prodromal synucleinopathy consists of delaying disease onset or time of disease diagnosis by at least 5%, such as at least 10%, such as at least 15%, such as at least 20%, such as at least 25%, such as at least 30%, such as at least 35%, such as at least 40%, such as at least 45%, such as at least 50%, such as at least 55%, such as at least 60%, such as at least 65%, such as at least 70%, such as at least 75%, such as at least 80%, such as at least 85% or such as at least 90%.

In a further embodiment the treatment of prodromal synucleinopathy consists of delaying disease onset or time of disease diagnosis by at least 6 months, such as at least 8 months, such as at least 10 months, such as at least 12 months, such as at least 14 months, such as at least 16 months, such as at least 18 months, such as at least 20 months, such as at least 22 months, such as at least 24 months, such as at least 2 years, such as at least 3 years, such as at least 4 years, such as at least 5 years.

In a further embodiment the invention provides a method of treatment of prodromal synucleinopathy where the treatment comprises administering the monoclonal alpha synuclein antibody in an amount and a frequency sufficient to achieve a CSF steady state concentration of the antibody of at least 0.5 nM, such as at least 1 nM, such as at least 2 nM, such as at least 3 nM, such as at least 6 nM, or such as at least 12 nM.

In a further embodiment the invention provides a method of treatment of prodromal synucleinopathy where the treatment comprises administering the monoclonal alpha synuclein antibody in an amount and a frequency sufficient to achieve a CSF steady state concentration of the antibody of at least 3 nM, such as at least 6 nM, or such as at least 12 nM.

In a further embodiment the invention provides a method of treatment of prodromal synucleinopathy where the treatment comprises administering the monoclonal alpha synuclein antibody in an amount and a frequency sufficient to achieve an estimated target engagement to oligomeric forms of alpha synuclein in CSF of at least 50%, such as at least 60%, such as at least 75%, such as at least 80%, such as at least 85%, such as at least 90%, such as at least 95%, or such as at least 99%.

In a further embodiment the invention provides a method of treatment of prodromal synucleinopathy where the treatment comprises administering the monoclonal alpha synuclein antibody in an amount and a frequency sufficient to achieve an estimated target engagement to oligomeric forms of alpha synuclein in CSF of at least 85%, such as at least 90%, or such as at least 95%.

In an aspect the present invention also provides a liquid pharmaceutical composition comprising a full length IgG1 monoclonal anti-alpha synuclein antibody in a concentration of 25-225 mg/mL, wherein said antibody comprises:
  a. a Heavy Chain CDR1 having the amino acid sequence of SEQ ID NO:1;
  b. a Heavy Chain CDR2 having the amino acid sequence of SEQ ID NO:34;
  c. a Heavy Chain CDR3 having the amino acid sequence of SEQ ID NO:3;
  d. a Light Chain CDR1 having the amino acid sequence of SEQ ID NO:4;
  e. a Light Chain CDR2 having the amino acid sequence of SEQ ID NO:5; and
  f. a Light Chain CDR3 having the amino acid sequence of SEQ ID NO:6;
  and wherein the composition further comprises histidine buffer, a pharmaceutically acceptable tonicity agent, a pharmaceutically acceptable surfactant and wherein the pH of the composition is between 5.5 to 6.5, this liquid pharmaceutical composition is suitable to be used to administer the monoclonal alpha synuclein antibody in any of the treatment, the methods of treatment of uses described in the aspects, embodiments or claims of this application.

In an embodiment of the invention the monoclonal antibody of the liquid pharmaceutical composition comprises a heavy chain consisting of a variable domain of SEQ ID NO:31 and a light chain consisting of a variable domain of SEQ ID NO:8.

In an embodiment of the invention the monoclonal antibody of the liquid pharmaceutical composition is a human antibody.

In an embodiment of the invention the monoclonal antibody of the liquid pharmaceutical composition is a human IgG1 antibody.

In an embodiment of the invention the monoclonal antibody of the liquid pharmaceutical composition is GM37 variant 2.

In a further embodiment of the invention the monoclonal antibody of the liquid pharmaceutical composition comprises a constant heavy chain domain as defined in SEQ ID NO:18 and a kappa light chain constant domain as defined in SEQ ID NO:17.

In an embodiment the tonicity agent of the liquid pharmaceutical composition is selected from Mannitol, Sorbitol, Lactose, Dextrose, Trehalose, Sodium Chloride (NaCl), Potassium Chloride (KCl), Glycerol or Glycerine.

In an embodiment the tonicity agent of the liquid pharmaceutical composition is Sodium Chloride (NaCl).

In an embodiment the tonicity agent of the liquid pharmaceutical composition is Sodium Chloride (NaCl) in a concentration of about 70-140 mM.

In an embodiment the tonicity agent of the liquid pharmaceutical composition is Sodium Chloride (NaCl) in a concentration of about 50-150 mM.

In an embodiment the tonicity agent of the liquid pharmaceutical composition is Sodium Chloride (NaCl) in a concentration of about 100 mM.

In an embodiment the surfactant of the liquid pharmaceutical composition is selected from Polysorbate 20 (Tween 20), Polysorbate 80 (Tween 80), Poloxamer 188 or Triton X-100.

In an embodiment the surfactant of the liquid pharmaceutical composition is Polysorbate 80 (Tween 80) in an amount between 0.02% to 0.05% (w/v).

In an embodiment the surfactant of the liquid pharmaceutical composition is Polysorbate 80 (Tween 80) in an amount of about 0.02% (w/v).

In an embodiment the tonicity agent of the liquid pharmaceutical composition is Sodium Chloride (NaCl) and the surfactant is Polysorbate 80 (Tween 80).

In an embodiment the concentration of the histidine buffer of the liquid pharmaceutical composition is between 25-40 mM.

In an embodiment the concentration of the histidine buffer of the liquid pharmaceutical composition is about 25 mM.

In an embodiment the pH of the liquid pharmaceutical composition is 6.0.

In an embodiment the monoclonal anti-alpha synuclein antibody concentration of the liquid pharmaceutical composition is about 30-225 mg/mL.

In an embodiment the monoclonal anti-alpha synuclein antibody concentration of the liquid pharmaceutical composition is about 30-200 mg/mL.

In an embodiment the monoclonal anti-alpha synuclein antibody concentration of the liquid pharmaceutical composition is about 30-150 mg/mL.

In an embodiment the monoclonal anti-alpha synuclein antibody concentration of the liquid pharmaceutical composition is about 30-100 mg/mL.

In an embodiment the monoclonal anti-alpha synuclein antibody concentration of the liquid pharmaceutical composition is about 45-55 mg/mL.

In an embodiment the monoclonal anti-alpha synuclein antibody concentration of the liquid pharmaceutical composition is about 50 mg/mL.

In an embodiment the monoclonal anti-alpha synuclein antibody concentration of the liquid pharmaceutical composition is about 53 mg/mL.

In an embodiment the liquid pharmaceutical composition of any of the proceeding embodiments further comprises at least one bulking agent selected from Sucrose, Trehalose, Glucose, Lactose, Sorbitol, Mannitol, Glycerol, Arginine, Aspartic Acid, Glutamic acid, Glutamate, Lysine, Glycine, Histidine, Methionine, Alanine, Gelatin, PVP, PLGA, PEG, dextran, cyclodextrin and derivatives, starch derivatives, HSA or BSA.

In an embodiment the bulking agent of the liquid pharmaceutical composition is Arginine, Glutamate, Sucrose, Glycine or Sorbitol in a concentration of 100-200 mM.

In an embodiment the bulking agent of the liquid pharmaceutical composition agent is Sucrose in a concentration of 100 mM.

In an embodiment the liquid pharmaceutical composition comprises 53 mg/mL of the monoclonal anti-alpha synuclein antibody, 25 mM histidine buffer, 100 mM Sucrose, 100 mM sodium chloride (NaCl) and 0.02% polysorbate 80 (Tween 80) (w/v) at pH 6.0.

In an embodiment the liquid pharmaceutical composition is essentially consisting of 53 mg/mL of the monoclonal anti-alpha synuclein antibody, 25 mM histidine buffer, 100 mM Sucrose, 100 mM sodium chloride (NaCl), 0.02% polysorbate 80 (Tween 80) (w/v) and water at pH 6.0.

In an embodiment the liquid pharmaceutical composition comprises 53±5 mg/mL of the monoclonal anti-alpha synuclein antibody, 1.40 mg/mL L-Histidine, 3.34 mg/mL L-Histidine monohydrochloride, 34.16 mg/mL Sucrose, 5.83 mg/mL sodium chloride (NaCl), 0.20 mg/mL polysorbate 80 (Tween 80) at pH 6.0.

In an embodiment the liquid pharmaceutical composition is essentially consisting of 53±5 mg/mL of the monoclonal anti-alpha synuclein antibody, 1.40 mg/mL L-Histidine, 3.34 mg/mL L-Histidine monohydrochloride, 34.16 mg/mL Sucrose, 5.83 mg/mL sodium chloride (NaCl), 0.20 mg/mL polysorbate 80 (Tween 80) and water at pH 6.0.

In an embodiment the liquid pharmaceutical composition comprises 53 mg/mL of the monoclonal anti-alpha synuclein antibody, 25 mM histidine buffer, 100 mM Sucrose, 100 mM sodium chloride (NaCl) and 0.02% polysorbate 80 (Tween 80) (w/v) or having amounts of each constituent within +/−10% of said values, and having a pH of 6.0 or within +/−10% of said value.

In an embodiment the liquid pharmaceutical composition is essentially consisting of 53 mg/mL of the monoclonal anti-alpha synuclein antibody, 25 mM histidine buffer, 100 mM Sucrose, 100 mM sodium chloride (NaCl), 0.02% polysorbate 80 (Tween 80) (w/v) and water or having amounts of each constituent within +/−10% of said values, and having a pH of 6.0 or within +/−10% of said value.

In an embodiment the liquid pharmaceutical composition comprises 53 mg/mL of the monoclonal anti-alpha synuclein antibody, 1.40 mg/mL L-Histidine, 3.34 mg/mL L-Histidine monohydrochloride, 34.16 mg/mL Sucrose, 5.83 mg/mL sodium chloride (NaCl), 0.20 mg/mL polysorbate 80 (Tween 80) or having amounts of each constituent within +/−10% of said values, and having a pH of 6.0 or within +/−10% of said value.

In an embodiment the liquid pharmaceutical composition is essentially consisting of 53 mg/mL of the monoclonal anti-alpha synuclein antibody, 1.40 mg/mL L-Histidine, 3.34 mg/mL L-Histidine monohydrochloride, 34.16 mg/mL Sucrose, 5.83 mg/mL sodium chloride (NaCl), 0.20 mg/mL polysorbate 80 (Tween 80) and water or having amounts of each constituent within +/−10% of said values, and having a pH of 6.0 or within +/−10% of said value.

In an embodiment the liquid pharmaceutical composition comprises 53 mg/mL of the monoclonal anti-alpha synuclein antibody, 25 mM histidine buffer, 100 mM Sucrose, 100 mM sodium chloride (NaCl) and 0.02% polysorbate 80 (Tween 80) (w/v) or having amounts of each constituent within +/−5% of said values, and having a pH of 6.0 or within +/−5% of said value.

In an embodiment the liquid pharmaceutical composition is essentially consisting of 53 mg/mL of the monoclonal anti-alpha synuclein antibody, 25 mM histidine buffer, 100 mM Sucrose, 100 mM sodium chloride (NaCl), 0.02% polysorbate 80 (Tween 80) (w/v) and water or having amounts of each constituent within +/−5% of said values, and having a pH of 6.0 or within +/−5% of said value.

In an embodiment the liquid pharmaceutical composition comprises 53 mg/mL of the monoclonal anti-alpha synuclein antibody, 1.40 mg/mL L-Histidine, 3.34 mg/mL L-Histidine monohydrochloride, 34.16 mg/mL Sucrose, 5.83 mg/mL sodium chloride (NaCl), 0.20 mg/mL polysorbate 80 (Tween 80) or having amounts of each constituent within +/−5% of said values, and having a pH of 6.0 or within +/−5% of said value.

In an embodiment the liquid pharmaceutical composition is essentially consisting of 53 mg/mL of the monoclonal anti-alpha synuclein antibody, 1.40 mg/mL L-Histidine, 3.34 mg/mL L-Histidine monohydrochloride, 34.16 mg/mL Sucrose, 5.83 mg/mL sodium chloride (NaCl), 0.20 mg/mL polysorbate 80 (Tween 80) and water or having amounts of each constituent within +/−5% of said values, and having a pH of 6.0 or within +/−5% of said value.

In an embodiment the liquid pharmaceutical composition comprises 53 mg/mL of the monoclonal anti-alpha synuclein antibody, 25 mM histidine buffer, 100 mM Sucrose, 100 mM sodium chloride (NaCl) and 0.02% polysorbate 80 (Tween 80) (w/v) or having amounts of each constituent within +/−1% of said values, and having a pH of 6.0 or within +/−1% of said value.

In an embodiment the liquid pharmaceutical composition is essentially consisting of 53 mg/mL of the monoclonal anti-alpha synuclein antibody, 25 mM histidine buffer, 100 mM Sucrose, 100 mM sodium chloride (NaCl), 0.02% polysorbate 80 (Tween 80) (w/v) and water or having amounts of each constituent within +/−1% of said values, and having a pH of 6.0 or within +/−1% of said value.

In an embodiment the liquid pharmaceutical composition comprises 53 mg/mL of the monoclonal anti-alpha synuclein antibody, 1.40 mg/mL L-Histidine, 3.34 mg/mL L-Histidine monohydrochloride, 34.16 mg/mL Sucrose, 5.83 mg/mL sodium chloride (NaCl), 0.20 mg/mL polysorbate 80 (Tween 80) or having amounts of each constituent within +/−1% of said values, and having a pH of 6.0 or within +/−1% of said value.

In an embodiment the liquid pharmaceutical composition is essentially consisting of 53 mg/mL of the monoclonal anti-alpha synuclein antibody, 1.40 mg/mL L-Histidine, 3.34 mg/mL L-Histidine monohydrochloride, 34.16 mg/mL Sucrose, 5.83 mg/mL sodium chloride (NaCl), 0.20 mg/mL polysorbate 80 (Tween 80) and water or having amounts of each constituent within +/−1% of said values, and having a pH of 6.0 or within +/−1% of said value.

In an embodiment the liquid pharmaceutical composition comprises 53 mg/mL of the monoclonal anti-alpha synuclein antibody, 25 mM histidine buffer, 100 mM Sucrose, 100 mM sodium chloride (NaCl) or having amounts of each constituent within +/−20% of said values and 0.02% polysorbate 80 (Tween 80) (w/v) or having a concentration within +/−30% of said concentration, and having a pH of 6.0 or within +/−20% of said value.

In an embodiment the liquid pharmaceutical composition comprises 53 mg/mL of the monoclonal anti-alpha synuclein antibody, 25 mM histidine buffer, 100 mM Sucrose, 100 mM sodium chloride (NaCl) or having amounts of each constituent within +/−15% of said values and 0.02% polysorbate 80 (Tween 80) (w/v) or having a concentration within +/−25% of said concentration, and having a pH of 6.0 or within +/−15% of said value.

In an embodiment the liquid pharmaceutical composition comprises 53 mg/mL of the monoclonal anti-alpha synuclein antibody, 25 mM histidine buffer, 100 mM Sucrose, 100 mM sodium chloride (NaCl) or having amounts of each constituent within +/−10% of said values and 0.02% polysorbate 80 (Tween 80) (w/v) or having a concentration within +/−20% of said concentration, and having a pH of 6.0 or within +/−10% of said value.

In an embodiment the liquid pharmaceutical composition is a stable liquid pharmaceutical composition.

In an embodiment the liquid pharmaceutical composition is a low viscosity liquid pharmaceutical composition.

It will be recognized that one or more features of any embodiments disclosed herein may be combined and/or rearranged within the scope of the invention to produce further embodiments that are also within the scope of the invention. All embodiments are meant to apply to all aspects of the present invention.

In specific embodiments of the invention the monoclonal alpha synuclein antibody of any of the preceding embodiments is administered to the patient in any one of the liquid pharmaceutical compositions of any of the preceding embodiments.

Those skilled in the art will recognize or be able to ascertain using no more than routine experimentation, many equivalents to the specific embodiments of the invention described herein. Such equivalents are intended to be within the scope of the present invention.

Experimental Section—Dosing Regimens

The examples provided below serve to facilitate a more complete understanding of the invention. However, the scope of the invention is not limited to specific embodiments disclosed in these Examples, which are for purposes of illustration only, since alternative methods can be utilized to obtain similar results.

Example 1—Model to Establish Dosage Regimens for Antibodies for Use According to the Invention Illustrated by GM37 Variant 2

This example outlines the inventive efforts performed by the inventors to enable establishment of clinically relevant human dosing regimens required to obtain a neutralization of oligomeric/aggregated pathological species of alpha synuclein in CSF of a patient with synucleinopathy. The dosing regimens are based on a model which requires extensive and in-depth knowledge of GM37v2 and its binding properties to different alpha synuclein species as illustrated by the experiments below (examples 2, 6, 6A, 7 and 7A) and the PK properties of GM37v2 including exposure in CSF and target engagement between GM37v2 and alpha synuclein (example 3).

The inventors of the present invention were able to arrive at the claimed dosing regimens by establishing the specific relationship for GM37v2 between the binding to monomeric alpha synuclein and binding to the oligomeric form of alpha synuclein. This specific relationship is unique for each alpha synuclein antibody and is essential to establish clinically relevant dosing regimens which provides the desired target engagement to the pathological forms of alpha synuclein in the CSF of the patient. In vitro, the KD value of binding to the monomeric form of alpha synuclein for GM37v2 was measured to 36 nM (5,400 ng/mL) (see example 6A) and the avidity-mediated enhanced KD to the oligomeric forms for GM37v2 was estimated to be approximately 65-fold (64.1+/−5.2) lower (that is, 0.5 nM; 83 ng/mL) (see example 2).

In addition to this fold change between the monomeric and oligomeric binding, detailed PK knowledge of GM37v2 is also required to obtain the dosing regimens of the invention. The PK properties were obtained via the experiment disclosed in example 3. GM37 variant 2 was found to have a clearance of approximately 0.25 L/day, such as 0.24 L/day and a T½ of approximately 30 days, such as 29 days.

Target engagement of GM37 variant 2 to alpha-synuclein can be calculated from the percentage free alpha-synuclein in plasma or CSF (not bound to GM37 variant 2).

Figure 6A:
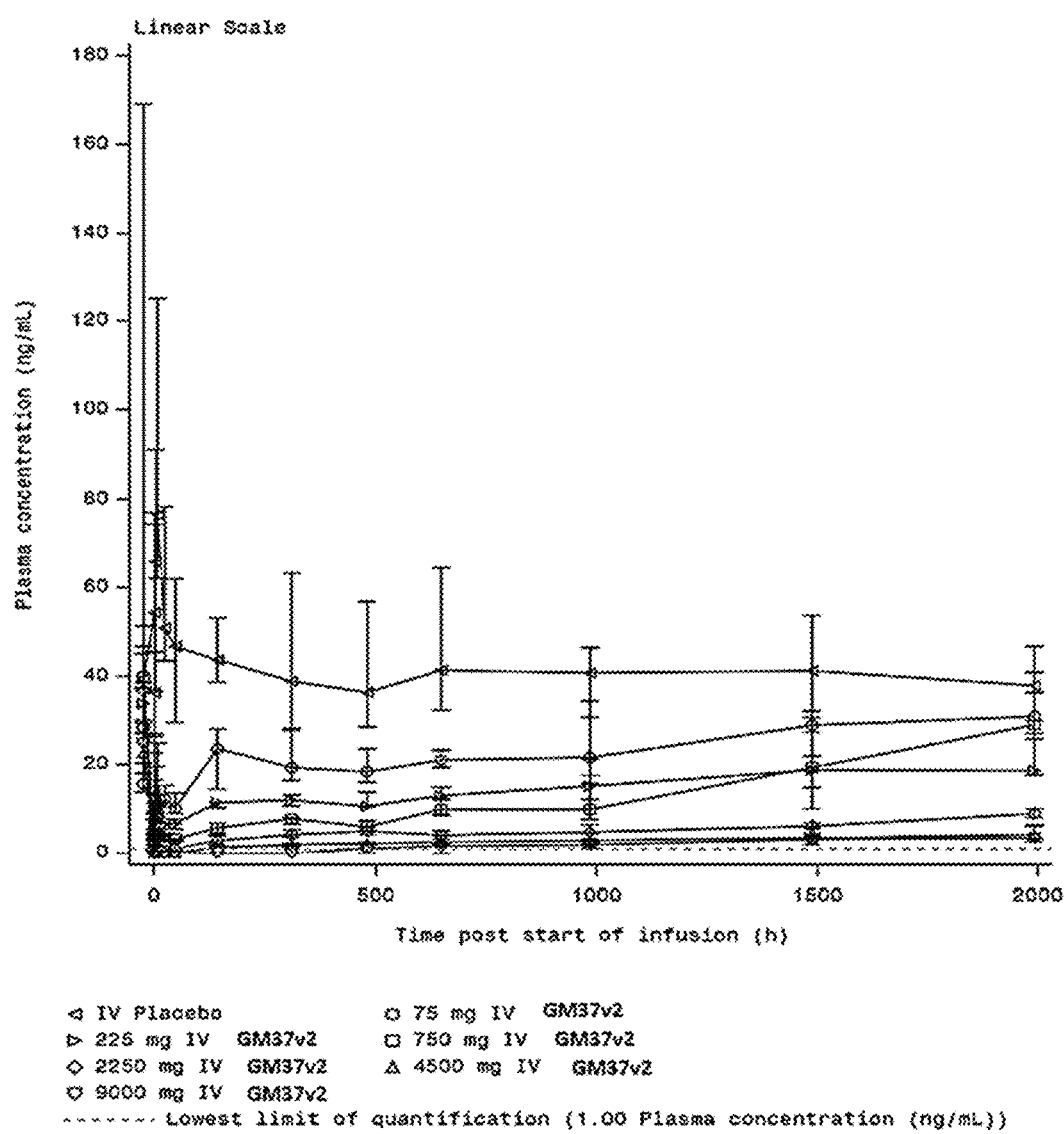
FIGS. 6A and 6B shows the free alpha synuclein plasma concentrations versus time for healthy subjects (FIG. 6A) and patients (FIG. 6B) following a single dose of GM37v2 at each dose level.
Figure 6B:
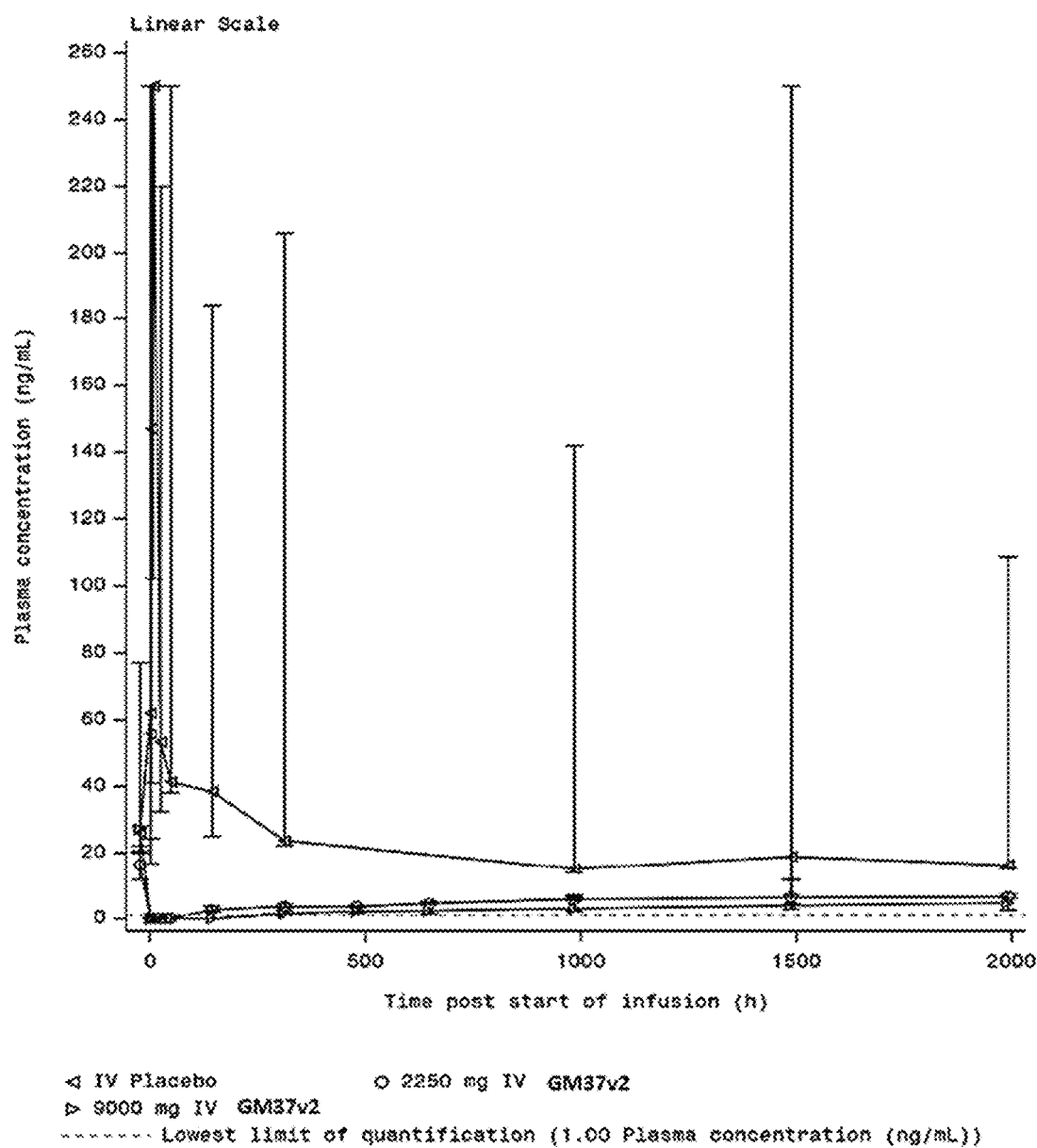
Figure 7A:
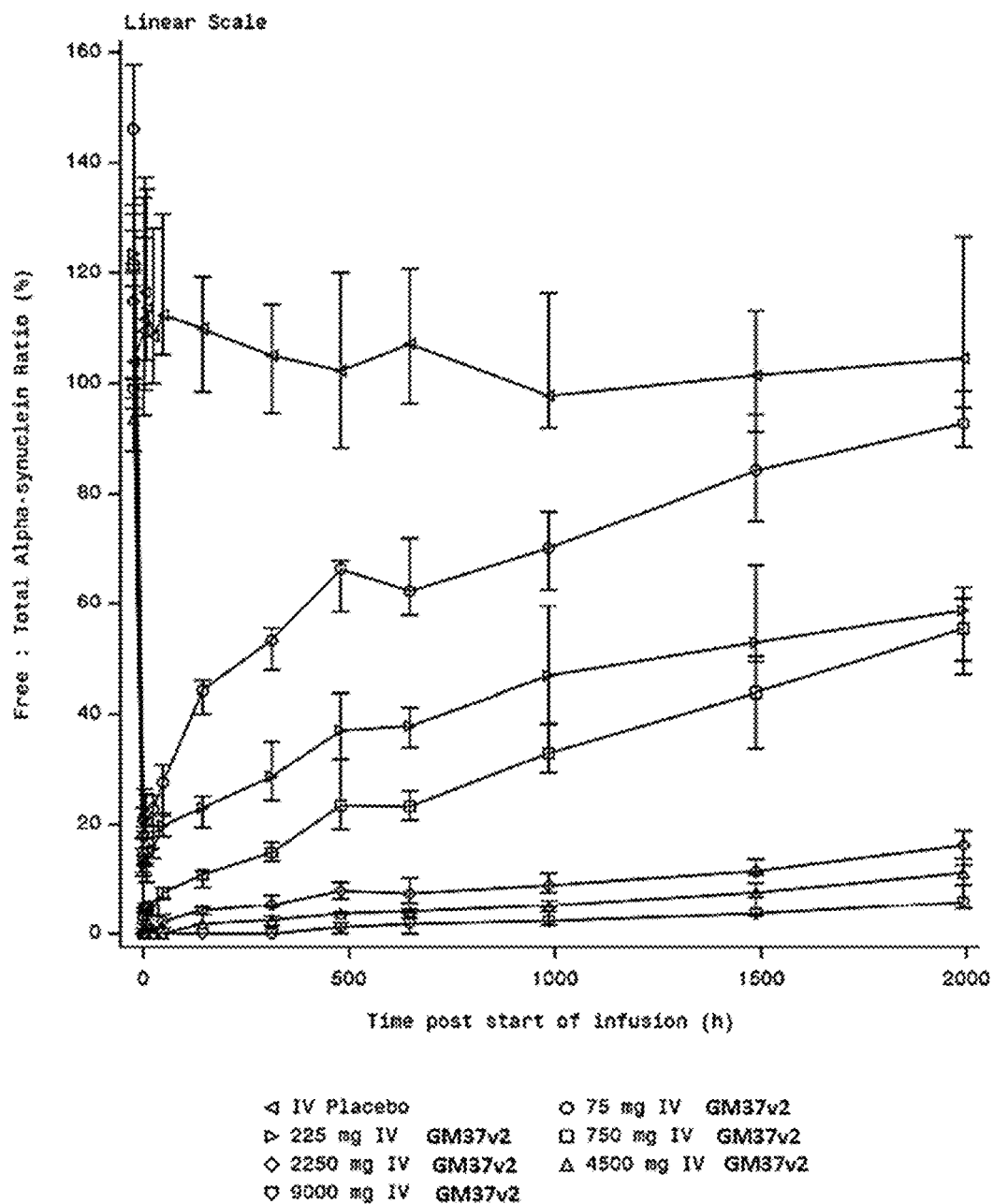
FIGS. 7A and 7B shows the free/total alpha synuclein plasma concentrations versus time for healthy subjects (FIG. 7A) and patients (FIG. 7B) following a single dose of GM37v2 at each dose level.
Figure 7B:
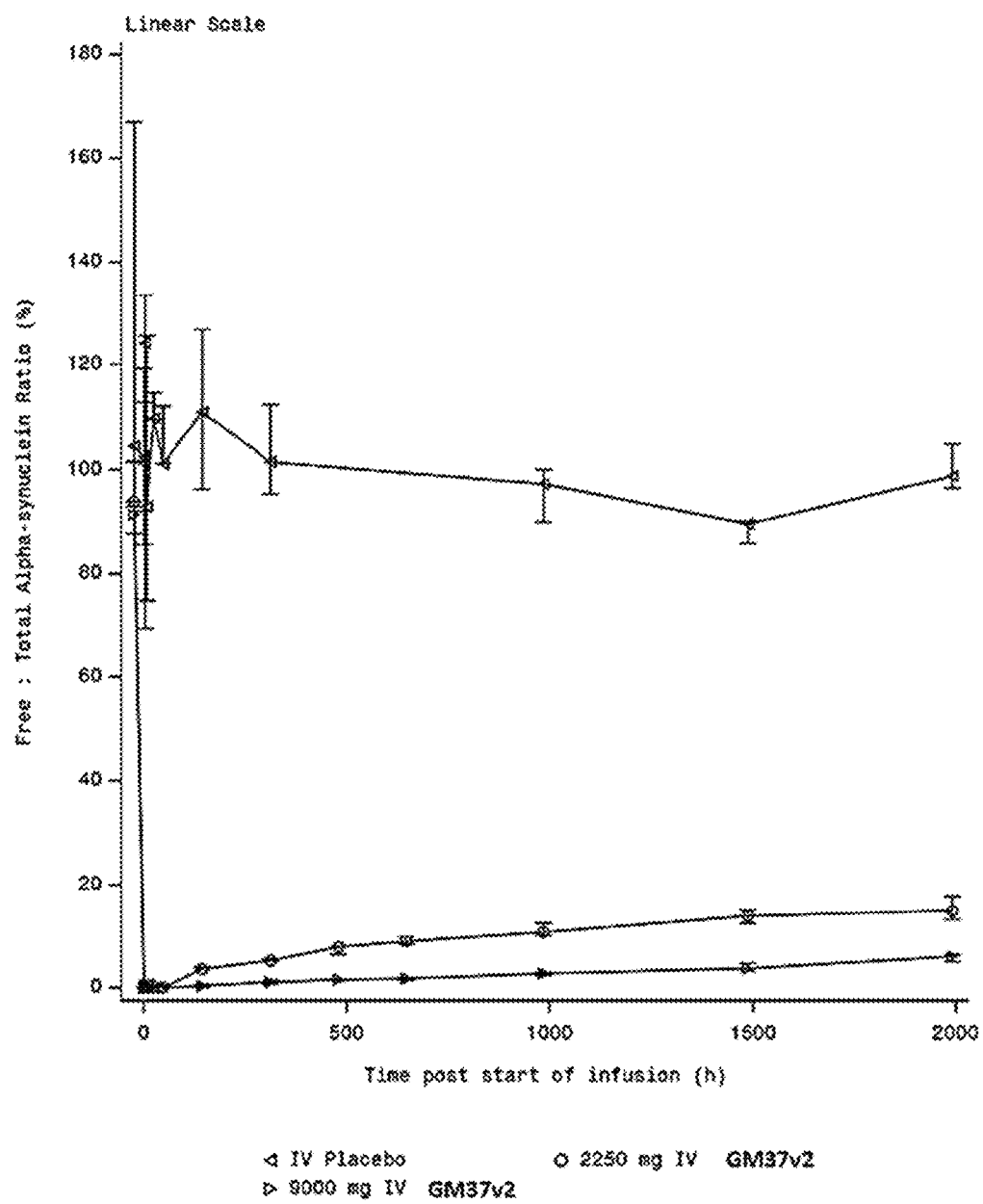
Figure 8:
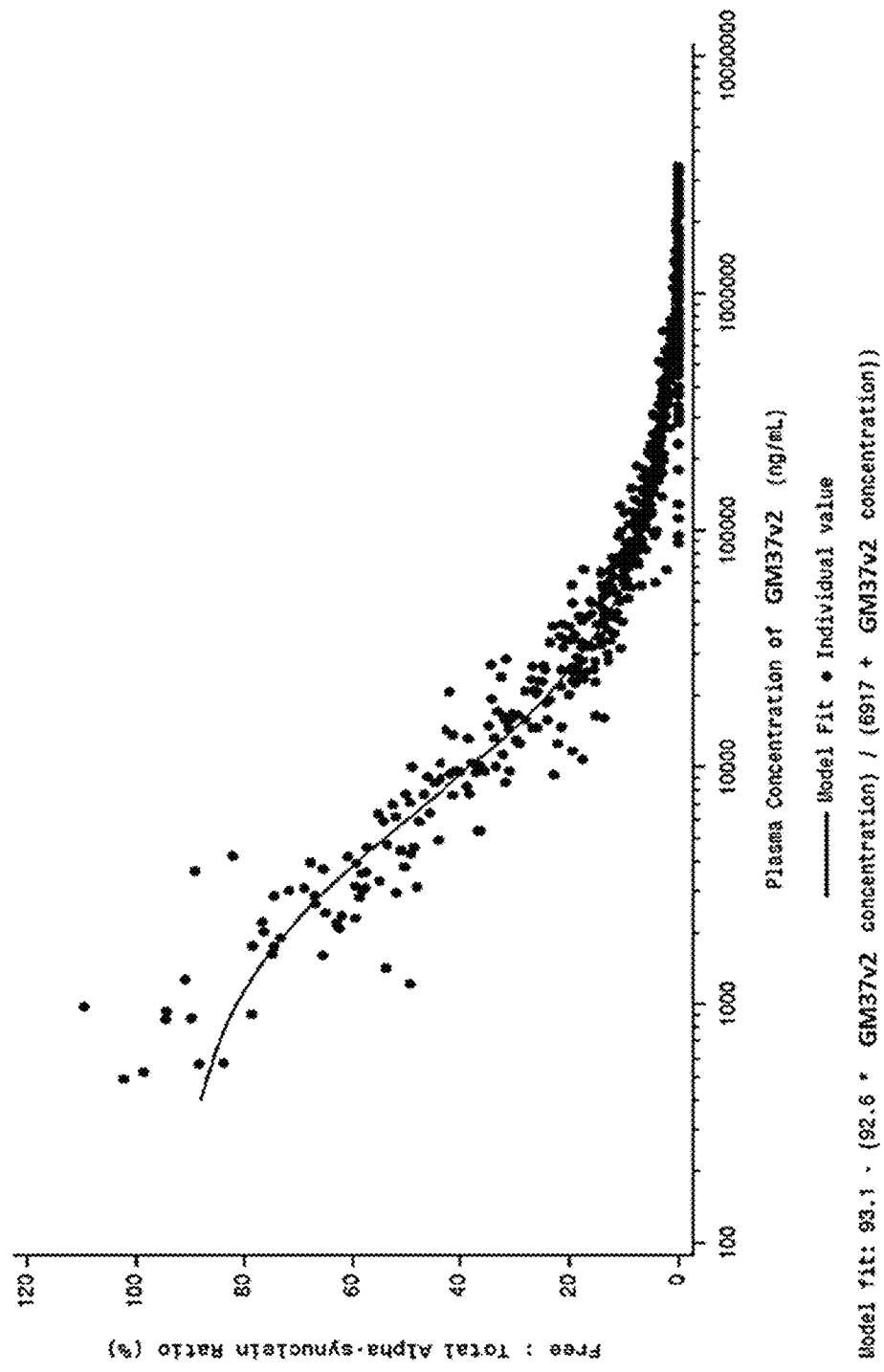
FIG. 8 shows the free/total alpha synuclein plasma concentrations versus individual GM37 variant 2 plasma concentrations.

FIG. 6 shows median free alpha synuclein plasma concentrations versus time for healthy subjects and patients. A clear dose related inhibition was observed. The same was observed for the % free/total alpha synuclein (FIG. 7). A good correlation between plasma concentrations of % free/total alpha synuclein and GM37 variant 2 is also seen in FIG. 8, where an Emax model (see below) was fitted to the data.

Notably the observed IC50 value was similar to the KD value measured in vitro providing experimental validation of the maximum inhibition Emax model described below.

According to the simple maximum inhibition $E_{max}$ model % free/total relevant for monomeric alpha synuclein target engagement is given by:

$$\% \text{ free/total alpha synuclein}_{mono} = E_{max} \cdot (Css/(KD+Css))$$

Wherein Emax is set to 100%, Css is the estimated mean steady state concentration of GM37v2 and KD is the in vitro measured binding to monomeric alpha synuclein (36 nM for GM37v2).

In order to establish relevant clinical doses of GM37v2 for treating synucleinopathies where the aggregated alpha synuclein is the primary target for the treatment and not the monomeric forms, it is required to adapt this model to take into account the avidity gain of 65-fold between the monomer and the oligomeric binding for GM37v2—this avidity gain obtained when targeting the aggregates vs. the monomers as described in example 2 and depicted in FIG. 1. For GM37v2 the avidity gain is 65-fold and hence the model for the aggregated species of alpha synuclein as primary target should employ a KD proxy value which is 65-fold lower than the monomeric KD of 36 nM (36 nM/65=0.5 nM). In the model below this estimated KD enhancement is denoted "(KD-avidity-gain)".

Accordingly, the $E_{max}$ model % free/total relevant for target engagement of aggregated forms of alpha synuclein is given by:

% free/total alpha synuclein$_{agg}$=$E_{max}$·(Css/(KD-avidity-gain+Css))

Css values can be calculated based on the results obtained in example 3:

For example, these parameters: dose=4200 mg; dosing interval=28 days; clearance=0.25 L/day; gives an estimated average plasma Css of (4200 mg/28 day)/0.25 L/day=600 mg/L=600 μg/mL.

Correspondingly, the average CSF Css is 0.3% of 600 μg/mL=1.8 μg/mL, equals 12 nM (because 1 μg/mL=6.67 nM, see below).

When Emax is set to 100% and the KD-avidity-gain is 0.5 nM it follows that in this specific example where GM37v2 CSF Css=12 nM, the estimated CSF target engagement to oligomeric/aggregated alpha synuclein is 96% following the below calculation:

% free/total alpha synuclein$_{agg}$=$E_{max}$·(Css/(KD-avidity-gain+Css))=100%·(12 nM/(0.5 nM+12 nM))=96%.

Based on the data summarized above and the value for the fold difference in the affinity/avidity to the target; alpha synuclein monomer versus oligomeric forms found in example 2, the doses of GM37 variant 2 that yield a predicted 85% to 95% target engagement in the CSF at steady state to alpha synuclein oligomeric forms at the following fixed doses (body weight 70 kg): 1050 mg (15 mg/kg), 2100 mg (30 mg/kg), and 4200 mg (60 mg/kg) every 4 weeks were modelled and are presented in FIG. 1; The plots are based on the predicted average CSF Css of GM37 variant 2 (calculated as dose/dosing interval/clearance as exemplified above) and a fraction in the CSF of 0.3% of the CSF Css. The binding is assumed to follow a simple sigmoid model of the Emax type and 1 nM GM37v2=0.15 μg/mL (1 μg/mL=6.67 nM).

Predictions Based on these Calculations:

1050 mg IV infusion once every 4 weeks is predicted to maintain GM37 variant 2 concentration in CSF and brain interstitial fluid (ISF) at around IC85, that is the average concentration for 85% of the oligomeric alpha synuclein to be bound.

2100 mg IV infusion once every 4 weeks is predicted to maintain GM37 variant 2 concentration in CSF and brain interstitial fluid (ISF) at around IC90, that is the average concentration for 90% of the oligomeric alpha synuclein to be bound.

4200 mg IV infusion once every 4 weeks is predicted to maintain GM37 variant 2 concentration in CSF and brain interstitial fluid (ISF) at around IC95, that is the average concentration for 95% of the oligomeric alpha synuclein to be bound.

Example 2—Competition ELISA—Target Engagement Monomers Vs Oligomers Illustrated by GM37 Variant 2

The binding profile of GM37 Variant 2 to the monomeric and fibril forms of alpha synuclein was characterized in this assay also referred to as a competition ELISA to determine the fold difference between binding to monomeric and fibrillar alpha synuclein.

Figure 2:
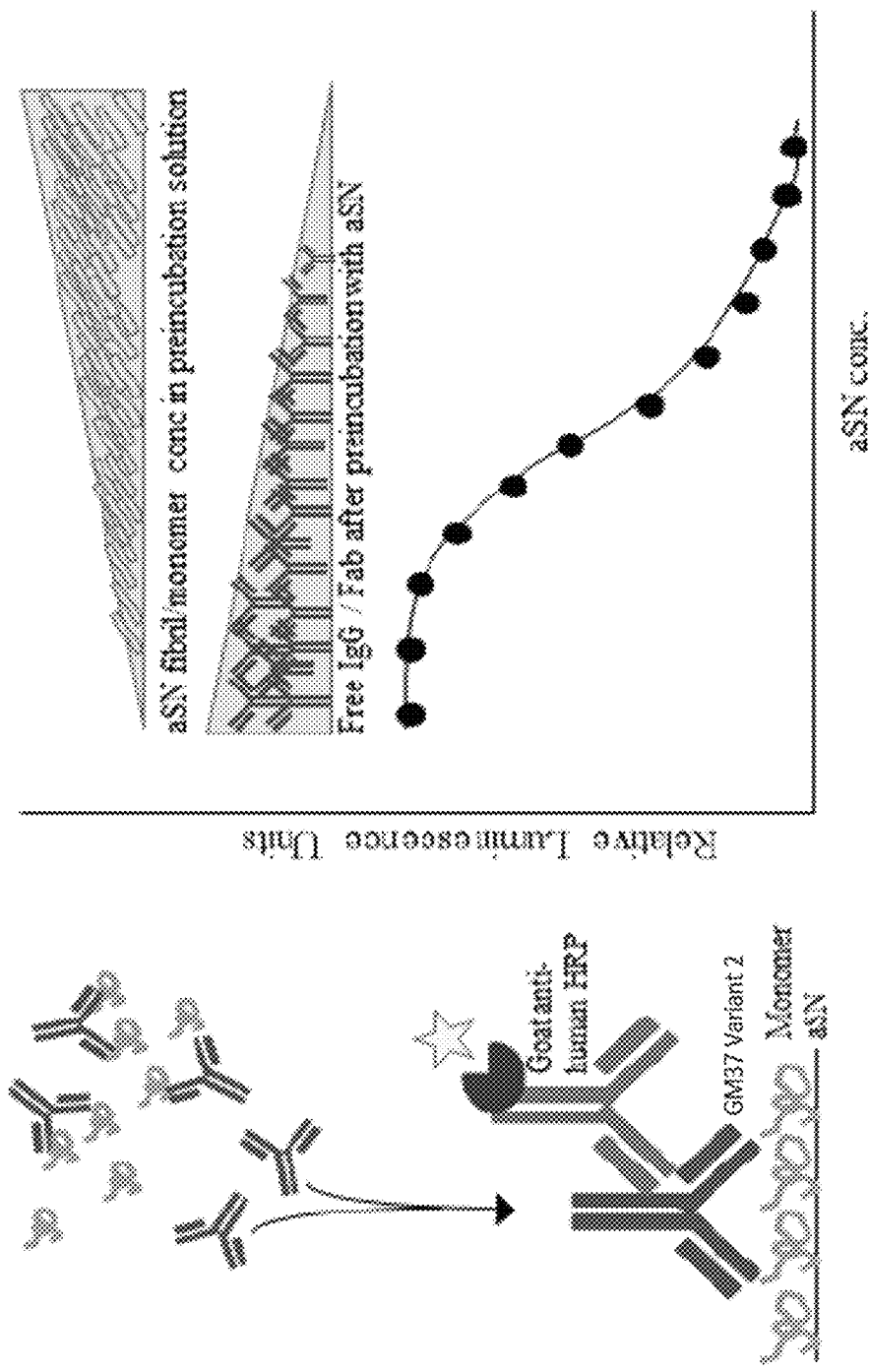
FIG. 2 shows the principle of the competition ELISA assay. Following preincubation with increasing concentrations of alpha synuclein (aSN) monomer or fibrils, free IgG is bound by coated aSN monomer and detected with an anti-human IgG (H+L) HRP labelled antibody (Left). Captured IgG levels, reversely proportional with the aSN monomer or fibril concentration, are plotted as relative Luminescence units, and IC50 values are calculated using a four-parameter non-linear fit (Right).

The assay principle is based on high density coating of monomeric alpha synuclein for capture of unbound anti-alpha synuclein mAb post preincubation with increasing concentrations of either monomer alpha synuclein or alpha synuclein fibrils. The observed IC50 values for either alpha synuclein monomer or alpha synuclein fibrils is thereby a relative measurement of the differential binding strength to the two representative biologically active species of alpha synuclein. The assay principle is illustrated in FIG. 2.

Production of Preformed Fibrils

The alpha synuclein monomer for preformed fibrils (PFFs) was produced from an eukaryotic source and fibrillated according to the protocol published in Polinski et al. J Parkinsons Dis. 2018; 8(2): 303-322.

Briefly, 400 μL monomeric alpha synuclein at 4 mg/mL in PBS was agitated at 37° C. by thermomixer at 1000 rpm in a 2 mL round-bottom tube for a duration of 5 days. The fibrillation of the protein was verified by increased fluorescence in response to Thioflavin T and increased hydrodynamic diameter measured by dynamic light scattering (DLS). The fibrils were sonicated by QSonica R800 (Amplitude 50, 20 s on, 10 s off, 10 min) to obtain a monodisperse size distribution (Z-average) below 100 nm measured by DLS. The PFFs were then aliquoted to 10 μL volumes and stored at −80 C until use.

On day one, 384 well plates are coated with alpha synuclein monomer, 1.4 μg/ml, 50 μl per well. The plates were incubated at 4° C. All solutions and plates were kept on ice and transferred directly to the fridge. The assay is continued the following day.

Serial twofold dilutions of alpha synuclein monomers and fibrils, ranging from 60 μM to 7.15 μM, were prepared in blocking buffer in a low bind polypropylene plate. Alpha synuclein fibril preparations were thawed at RT, whereas the alpha synuclein monomer preparations were thawed on ice. Just before use, monomer and fibrillar stock solutions were mixed gently by pipetting half the total volume three times. Equal volumes of mAb (40 ng/ml) were added to all wells containing the dilution series of alpha synuclein, and the low bind plate incubate for 2 hrs at RT with gentle agitation on a vertical plate shaker (300 rpm) to allow antibody-antigen complexes to form. Two wells with blocking buffer were included as blanks and two wells with mAb+blocking buffer were included as positive controls. 1 hr before the above-described pre-incubation is completed, the alpha synuclein coated assay plates were washed three times with PBS-T using the 384-well automated plate washer, and 100 μl of blocking buffer is added to each well and the plates were incubated for 1 hr at RT.

Prior to use, the assay plates were emptied over a sink and thoroughly tapped on a paper towel to ensure that the wells are completely emptied. The pre-incubated samples were added to the assay plates in duplicates of 50 μl per well, and the plates were incubated for 10 min at RT.

The plates were washed three times with PBS-T using the 384-well automated plate washer. 50 μl of the secondary goat anti-human—HRP antibody, diluted 1:15.000 in blocking buffer, was added per well followed by incubation for 1 hr at RT.

The plates were washed three times with PBS-T using the 384-well automated plate washer. The two ELISA substrate components were mixed 1:1 in appropriate volumes and 50 μl is added to all wells. Immediately after addition the Luminescence signals were quantified in an Envision microtiter plate reader.

IgG binding curves were fitted and IC50 values calculated using equation: Sigmoidal, 4PL, X is log(concentration) Y=Bottom+(Top-Bottom)/(1+((X^HillSlope)/(IC50^Hillslope))).

Results

The binding of GM37 Variant 2 to monomeric and fibrillar alpha synuclein was characterized in a competition ELISA. The analysis was performed in two independent replicates per day which were repeated at three different days, using one monomer alpha synuclein preparation and three different alpha synuclein fibril batches. The used antibody concentration (final 20 ng/ml or 133 pM) was, before this analysis, shown to be in the dynamic range of the antibody titration curve when using a 1.4 µg/ml monomer solution for coating the wells. This enables differentiation of free antibody levels.

Based on the six independent competition ELISA analyses, GM37 Variant 2 has an average IC50 value to monomeric alpha synuclein of 183.9±20.5 nM and an average IC50 value to fibrillar alpha synuclein of 2.9±4 nM (see Table below). Based on these numbers GM37 Variant 2 has an average preference for binding to fibrillar alpha synuclein of 64.1±5.2 fold, about 65 fold.

Table showing the six specific experiments for GM37 Variant 2 binding properties to monomer and fibril alpha synuclein

| mAb tested | IC50 monomer alpha synuclein (nM) | IC50 fibrillar alpha synuclein (nM) | Fold preference for fibril binding |
| --- | --- | --- | --- |
| GM37 Variant 2 | 162.2 | 2.65 | 61.3 |
| GM37 Variant 2 | 169.6 | 2.30 | 73.7 |
| GM37 Variant 2 | 211.8 | 3.28 | 64.5 |
| GM37 Variant 2 | 193.0 | 2.91 | 66.4 |
| GM37 Variant 2 | 161.2 | 2.84 | 56.8 |
| GM37 Variant 2 | 205.7 | 3.32 | 61.9 |
| Average | 183.9 | 2.9 | 64.1 |
| SD | 20.5 | 0.4 | 5.2 |

Figure 3:
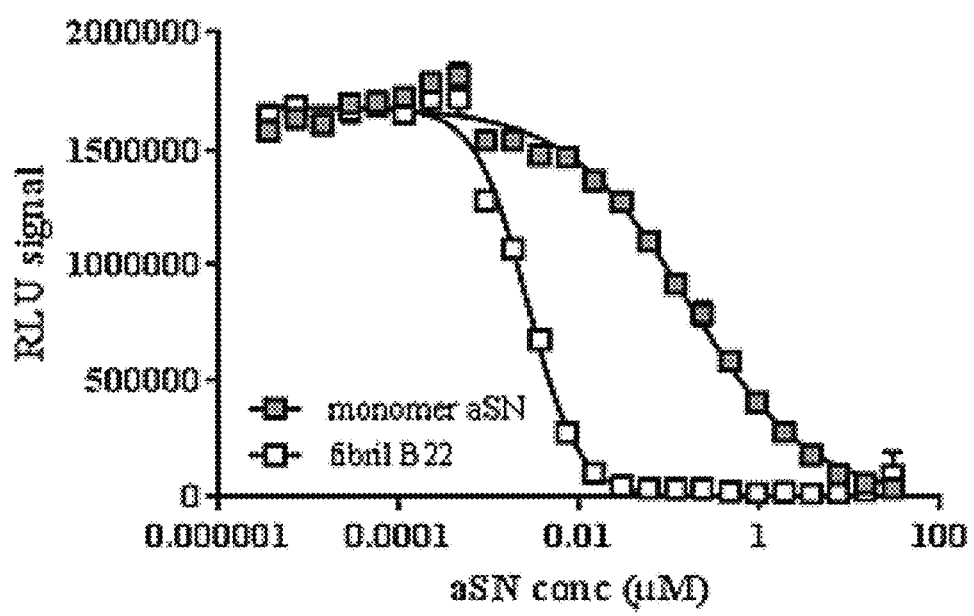
FIG. 3 shows Representative GM37 variant 2 binding curves to monomer (R2=0.9895) and fibrillar aSN (R2=0.994).

As seen in FIG. 3 the GM37 Variant 2 IC50 values are calculated from accurate curve fits and full titration curves of both monomer and alpha synuclein fibrils. In addition, the assay reproducibility across measurements was good with IC50 CV (%) values of 11.2% (monomer alpha synuclein) and 12.3% (fibrillar alpha synuclein). Likewise, the calculated GM37 Variant 2-fold preference for binding to aSN fibrils presented with a low CV value of 8,1%. Noteworthy, the numbers are based on analyses of three different fibril batches, demonstrating the assay stability.

A similar analysis was performed using a Fab fragment derived from GM37v2, to discriminate between the contribution of avidity by the IgG format or the existence of a fibril induced conformational epitope. The Fab fragment has no preference for binding to fibrillar alpha synuclein. Together, these data indicate that the GM37v2 preference for binding to fibrillar alpha synuclein is solely driven by avidity, with no indication of fibrillar selectivity or a specific conformational fibril epitope.

In summary, the competition ELISA experiment showed that GM37 Variant 2 has around 65-fold preferential binding to fibril compared to monomer alpha synuclein; this number can be referred to as an avidity gain in binding and was used for developing the dosage regimen model described in example 1.

Further, the inventors also evaluated the binding affinity/avidity of GM37var2 to MSA and PD brain homogenates enriched for aggregated, insoluble alpha synuclein by ELISA (data not shown). The EC50 of GM37var2 to brain derived alpha synuclein oligomers and fibrils in these samples was shown to be around 0.09-0.16 nM, supporting the clinical relevance of the sub-nanomolar binding to fibrils seen with recombinant material in the experimental setup described above.

Example 3—Single Ascending Dose (SAD) Study for Antibodies for Use According to the Invention Illustrated by GM37 Variant 2

This was an interventional, randomized, double-blind, sequential-group, placebo-controlled, single-ascending-dose study. The study was conducted to determine the safety, tolerability, PK, and pharmacodynamic properties of GM37 variant 2 in healthy non-Japanese and Japanese subjects (Part A) and in patients with PD (Part B).

Part A consisted of 6 sequential cohorts (Cohorts A1 to A6):
  Cohorts A1 to A3: 8 healthy subjects per cohort: 6 randomized to GM37v2 and 2 randomized to placebo.
  Cohorts A4 to A6: 11 to 12 healthy subjects per cohort stratified by ethnicity, aiming for an equal number of non-Japanese and Japanese; per ethnic group: up to 4 subjects randomized to GM37v2 and 1 to 2 subjects randomized to placebo.
Part B consisted of two cohorts (Cohorts B1 and B2):
  Cohorts B1 and B2: 7 to 8 patients with Parkinson's disease (PD): 6 patients randomized to GM37v2 and 1 to 2 patients randomized to placebo.
The dose range was 75 to 9000 mg; the exact dose increments were decided at dosing conferences. Part A: 6 doses tested; 75 mg-225 mg-750 mg-2250 mg-4500 mg-9000 mg in healthy subjects. Part B: 2 doses tested; 2250 mg and 9000 mg in PD patients.
The GM37v2 and placebo doses were administered by intravenous (IV) infusions over a 60-minute period (±10 minutes).
Within each cohort, the first 2 subjects/patients received either GM37v2 or placebo (1:1) and hence served as sentinel subjects/patients to assess safety and tolerability before the remaining subjects/patients were dosed.
In Cohorts A1, A2, A3, 81, and B2, following the sentinel subjects: up to 6 subjects received GM37v2 or placebo (5:1) at least 14 days after the sentinel subjects were dosed and their safety data reviewed. The 6 subjects were dosed at staggered intervals, with a maximum of 3 subjects initiated on the same day (with a maximum of 30 minutes overlap between each infusion) and a minimum of 1 day before initiation of the next staggered group.
In Cohorts A4, A5, and A6, following the sentinel subjects: between 9 to 10 subjects received GM37v2 or placebo (7:2 in Cohort A4, 7:3 in Cohort A5, and 6:3 in Cohort A6) at least 14 days after the sentinel subjects were dosed and their safety data reviewed. The 10 subjects were dosed at staggered intervals, with a maximum of 3 subjects initiated on the same day (with a maximum of 30 minutes overlap between each infusion) and a minimum of 1 day before initiation of the next staggered group.
Parts A and B were run in parallel. However, the dose administered to patients with PD in Cohort B1 did not exceed the dose tested in healthy subjects in Part A. Initiation of Cohort B1 was based on the safety and tolerability evaluation of the first 6 subjects in Cohort A4 (that is, at the same dose).

All subjects/patients were screened within 3 and 7 weeks, respectively, before administration of GM37v2. Eligible subjects/patients were confined to the clinic from 2 days before dosing (Day −2) until 3 days after dosing (afternoon of Day 4). The subjects/patients subsequently returned at regular intervals for outpatient visits until the final assessment 12 weeks after administration of IMP.

Safety and tolerability were assessed throughout the study.

Blinded safety and tolerability data, preliminary pharmacokinetic data, and preliminary peripheral blood and CSF pharmacodynamic (target engagement) data for Part A were evaluated and discussed at dosing conferences prior to dose escalation and initiation of each cohort in Part A. Dose escalation for the second cohort in Part A (Cohort A2) was based on the evaluation of 4 weeks of safety data from the first cohort (Cohort A1); for each subsequent cohort in Part A, dose escalation was based on at least 2 weeks of safety data from the previous cohorts in Part A.

Pharmacokinetic Results:

Following an IV infusion of GM37v2, median tmax occurred within 8 to 90 minutes after the end of infusion (individual range 1.00 to 5.00 hours post start of infusion) in non-Japanese subjects, slightly later, within 15 to 150 minutes after the end of infusion (individual range 1.00 to 5.00 hours post start of infusion) in Japanese subjects, and within 38 to 45 minutes after the end of infusion (individual range 1.00 to 5.00 hours post start of infusion) in patients with PD. By the end of infusion (1 hour post-dose), Cmax had not been reached in the majority of subjects/patients (that is, 35 of the 41 subjects who received GM37v2 in Part A and 10 of the 12 patients who received GM37v2 in Part B). There was no apparent effect of GM37v2 dose on tmax for healthy subjects (Japanese or non-Japanese) or patients with PD, with similar median values and overlapping ranges between the dose groups.

Following Cmax, the "free" concentration of GM37v2 in plasma declined in a multi-phasic manner and was quantifiable up to the last collected pharmacokinetic sample for all subjects/patients (Day 84 for all except 1 subject in Cohort A5 who's last sample collected on Day 63) in both Parts A and B.

Clearance was found to be an approximated overall mean CL of 0.01 L/h (0.24 L/d) across all dose groups and parts of the study (range 0.00883 to 0.0121 L/h) and with an approximated overall mean t½ of approximately 700 hours (29 days; range 565 to 843 hours); for comparison, endogenous immunoglobulin G1 has a CL of 0.21 L/d and a t½ of 21 days.

The exposure (Cmax and AUCs) of GM37v2 was comparable between Japanese and non-Japanese subjects and between healthy subjects and patients with PD. Half-life, clearance, and volume of distribution were comparable at all doses as well as in Japanese and non-Japanese subjects and between healthy subjects and patients with PD.

The pharmacokinetics of "free" GM37v2 was linear, with an increase in dose over the 75 to 9000 mg dose range in Part A and the 2250 to 9000 mg dose range in Part B resulting in approximately dose-proportional increases in exposure.

"Free" GM37v2 crossed the blood brain barrier and was detectable in all CSF samples collected on Days 3 and 21 from subjects/patients in Parts A and B, with the exception of 1 subject (75 mg GM37v2) where "free" GM37v2 was below the limit of quantification in CSF on both Days 3 and 21. The CSF:plasma ratios were between 0.0955% to 0.137% on Day 3 and between 0.164% to 0.512% on Day 21. The CSF:plasma ratios were comparable at all doses and between healthy subjects and patients with PD.

Figure 4A:
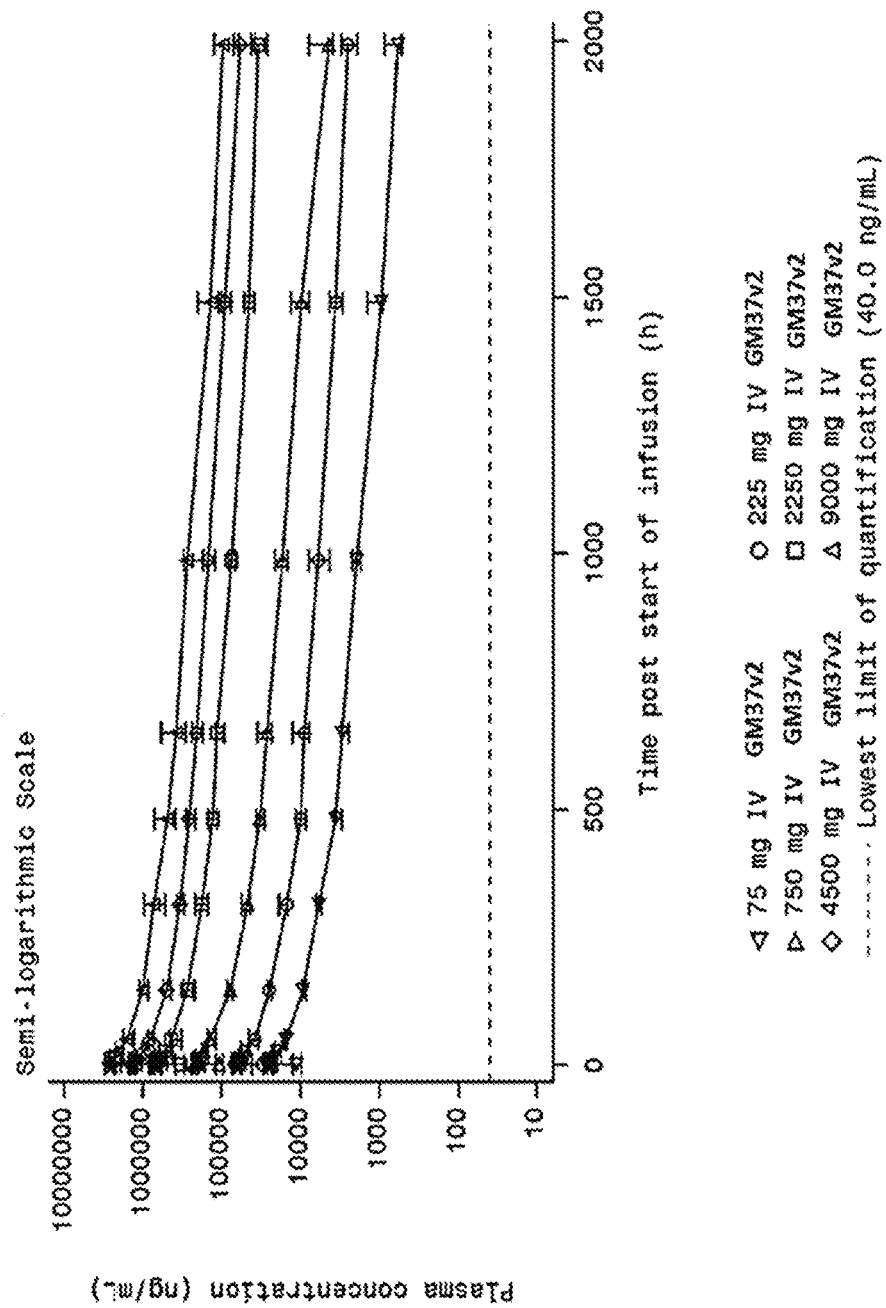
FIGS. 4A and 4B shows the median (including quartiles) plasma concentration (ng/mL) versus time of GM37 variant 2 for healthy subjects (FIG. 4A) and patients (FIG. 4B) following a single dose of GM37v2 at each dose level.
Figure 4B:
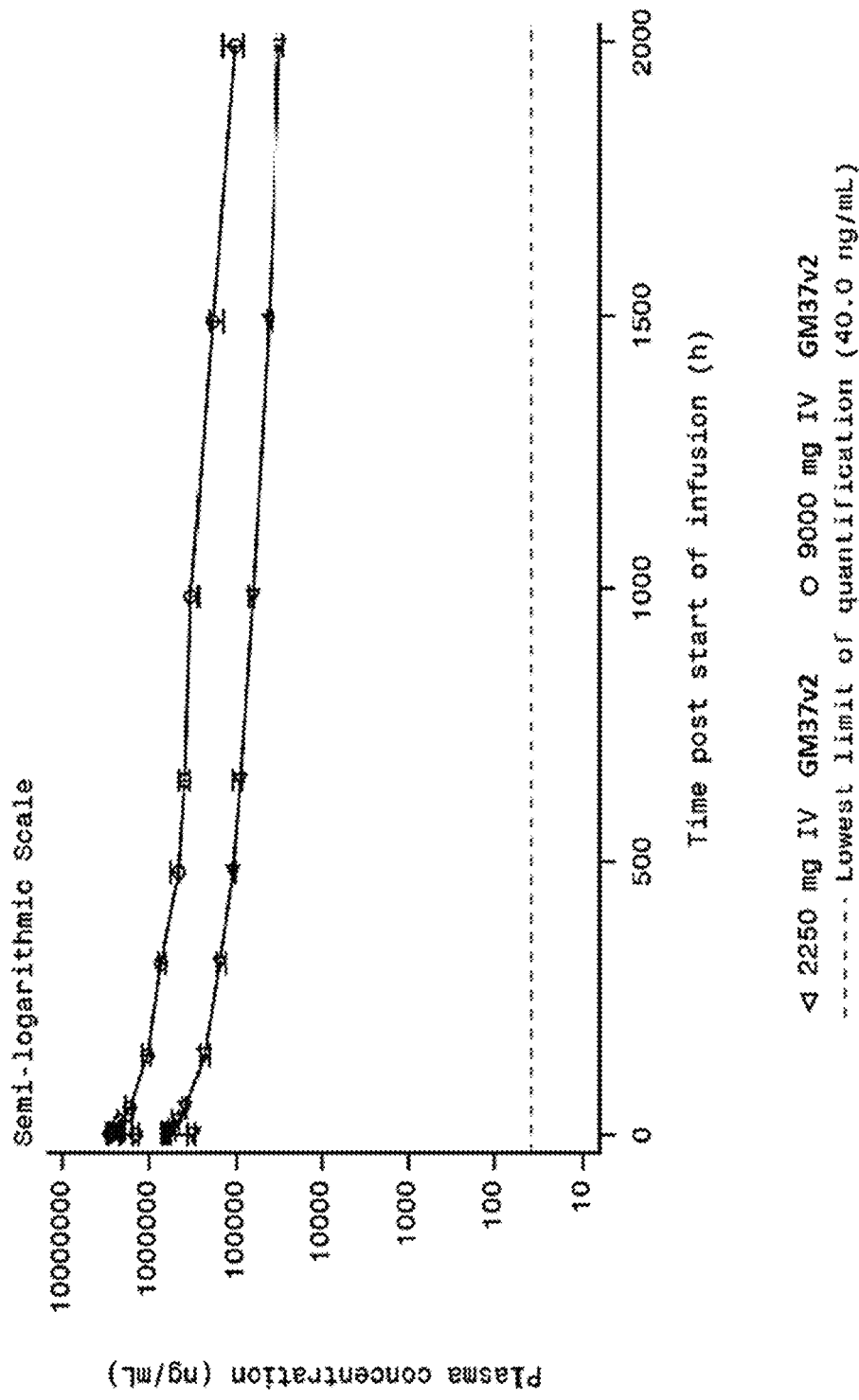

The median (including quartiles) plasma concentration (ng/mL) of GM37 variant 2 for healthy subjects (Cohort A1 to A6) and patients (Cohort B1 to B2) at each dose level versus time is depicted in FIG. 4a and b.

Pharmacodynamic Results

In both Parts A and B, a dose-dependent reduction in "free" alpha synuclein in plasma, as a result of GM37v2 binding, was observed starting immediately after the infusion of GM37v2. A similar pattern was evident for free:total alpha synuclein but with apparently less variability (FIGS. 6 and 7). There was a transient increase in "total" alpha synuclein concentrations following all doses of GM37v2, presumably due to binding to GM37v2, returning to baseline prior to Day 84.

There was no apparent difference in "free" or "total" plasma alpha synuclein levels between Japanese and non-Japanese subjects in the 2250, 4500, and 9000 mg dose groups.

The mean "free" alpha synuclein levels in plasma had not returned to baseline by the last sampling time on Day 84 for healthy subjects in Part A or patients with PD in Part B.

There was a small dose-dependent reduction in mean free:total alpha synuclein CSF ratios on Day 3, both in healthy subjects in Part A at the highest doses of GM37v2 (4500 and 9000 mg) and in patients with PD in Part B.

In Part A, the mean change from baseline in free:total alpha synuclein CSF ratios on Day 3 ranged between −27.9% and 8.06% with the largest decreases (−6.56% and −27.9%) occurring at the highest 4500 and 9000 mg doses. On Day 21, the mean free:total ratio of alpha synuclein decreased from baseline in the placebo (−2.15%) and the 225 to 4500 mg GM37v2 dose groups by between −1.7% to −15.1%. In Part B, the ratios changed from baseline by −8.08% on Day 3 for the 2250 mg dose of GM37v2 and −38.8% on Day 3 and −36.6% on Day 21 for the 9000 mg dose GM37v2.

"Free" plasma alpha synuclein and plasma free:total alpha synuclein could be fitted to maximum inhibition (Emax) models where increasing concentrations of GM37v2 were related to lower plasma "free" synuclein levels and free:total plasma alpha synuclein ratios. The estimated drug concentration required to produce 50% of maximal inhibition values were 11049 ng/mL for "free" plasma alpha synuclein and 6917 ng/mL for free:total plasma alpha synuclein ratios (FIG. 8).

Figure 11:
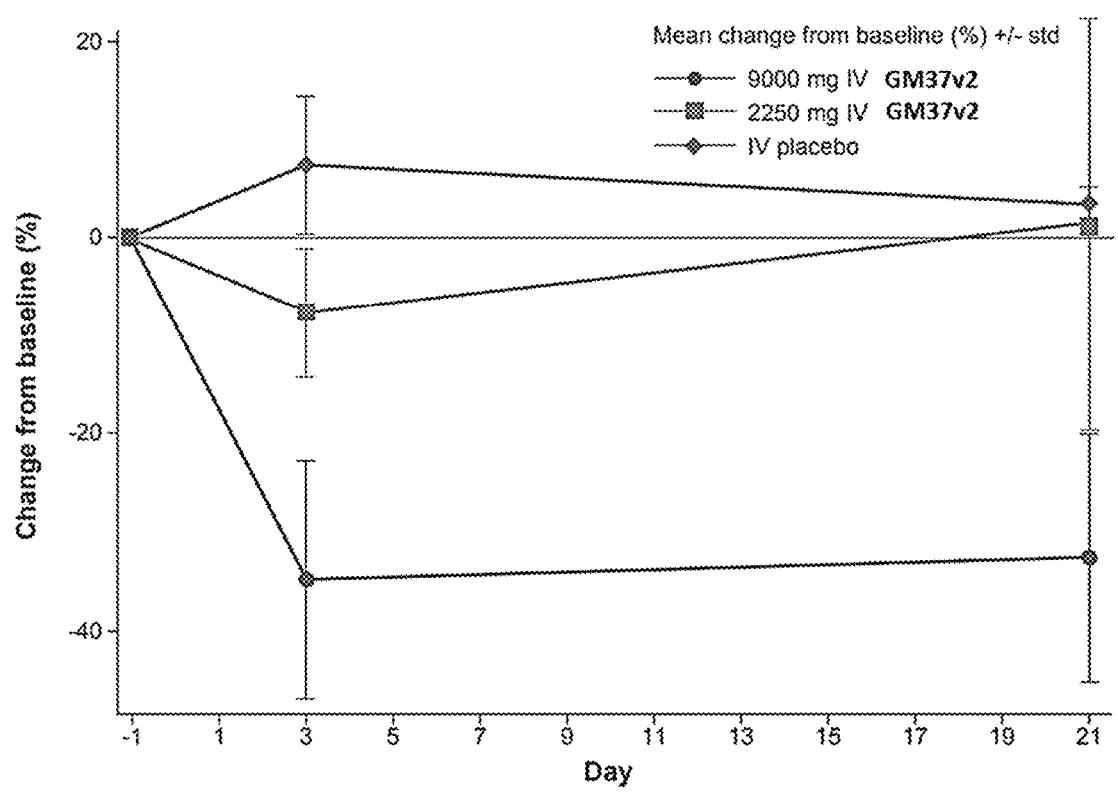
FIG. 11 shows the CSF concentrations of % free/total alpha synuclein in patients with Parkinson's Disease (PD) by GM37v2 dose at day 3 and day 21 of the study described in example 3 (N=15).

Target Engagement Results:

In addition to the target engagement of the monomeric alpha synuclein in plasma (FIG. 8), the inventors of the present invention were also surprisingly able to show target engagement to monomeric alpha synuclein in CSF of parkinson's patients after a single dose with GM37v2 (FIG. 11). To the best of our knowledge this is the first time that such target engagement has been demonstrated in clinical studies with antibodies against alpha synuclein although other such antibodies with similar or stronger monomeric binding have been tested in the clinical. E.g., Prasinezumab (PRX002 or 9E4) has been reported to have 20 nM binding to monomeric alpha synuclein, but no effect was seen on free alpha synuclein in CSF in a clinical trial of this antibody including Parkinson's patients and doses between 0.3 mg/kg and 60 mg/kg (Jankovic et al., JAMA Neurol. 2018 October; 75(10): 1206-1214).

The high dose in the SAD study (9000 mg) described above was chosen to reach concentrations in CSF that are comparable to those expected after multiple dosing with 4500 mg dose after accumulation of the antibody. FIG. 11 shows the change from baseline in % of free/total alpha synuclein measured in CSF samples obtained on day 3 and 21 from patients with parkinson's disease, with around 36% reduction in free/total monomeric alpha synuclein form baseline at the 9000 mg dose. As the binding of GM37v2 to oligomeric form is approximately 65-fold higher, this supports the estimation by the inventors that even much higher target engagement of aggregated, oligomeric alpha synuclein in the CNS may be achieved, up to the 95% as estimated by the model (see FIG. 1 and example 1). These data support that the dosing regimens of the present invention will be able to slow disease progression of synucleinopathies by neutralisation and clearance of oligomeric alpha synuclein bound with antibody in the extracellular matrix.

Example 4—Population PK (PopPK) Analysis from Data Collected in Example 3

The objective of the PopPK analysis was to obtain PK data to support the dose selected for the Clinical investigation in patients with synucleinopathies. The PopPK model was developed to describe the time course of GM37 variant 2 PK following single dosing in healthy subjects and to explore the impact of covariates on relevant PK parameters.

In total, 694 PK measurements from 41 subjects from Part A (Cohorts A1 to A6) were included in the PopPK analysis. The GM37 variant 2 plasma concentrations were analysed using nonlinear mixed effects methods. First, a structural model was developed, starting from a simple one-compartment model and continuing with increasing complexity. Different interindividual variability (IIV) models and different residual variability models were investigated to arrive at a stable structural model. Subsequently, covariate relationships were examined in a stepwise procedure (forward inclusion step using a significance criterion of p <0.01 followed by a backward elimination step using a significance criterion of p<0.005) to examine the impact of individual subject characteristics (body weight [WT], height [HT], age, sex, race, and baseline alpha synuclein) on model parameters. Model selection was informed using the objective function value, by the evaluation of numerical checks (such as parameter estimates and respective precision), graphical goodness-of-fit checks, and scientific and physiological plausibility.

Results of PopPK

Figure 5:
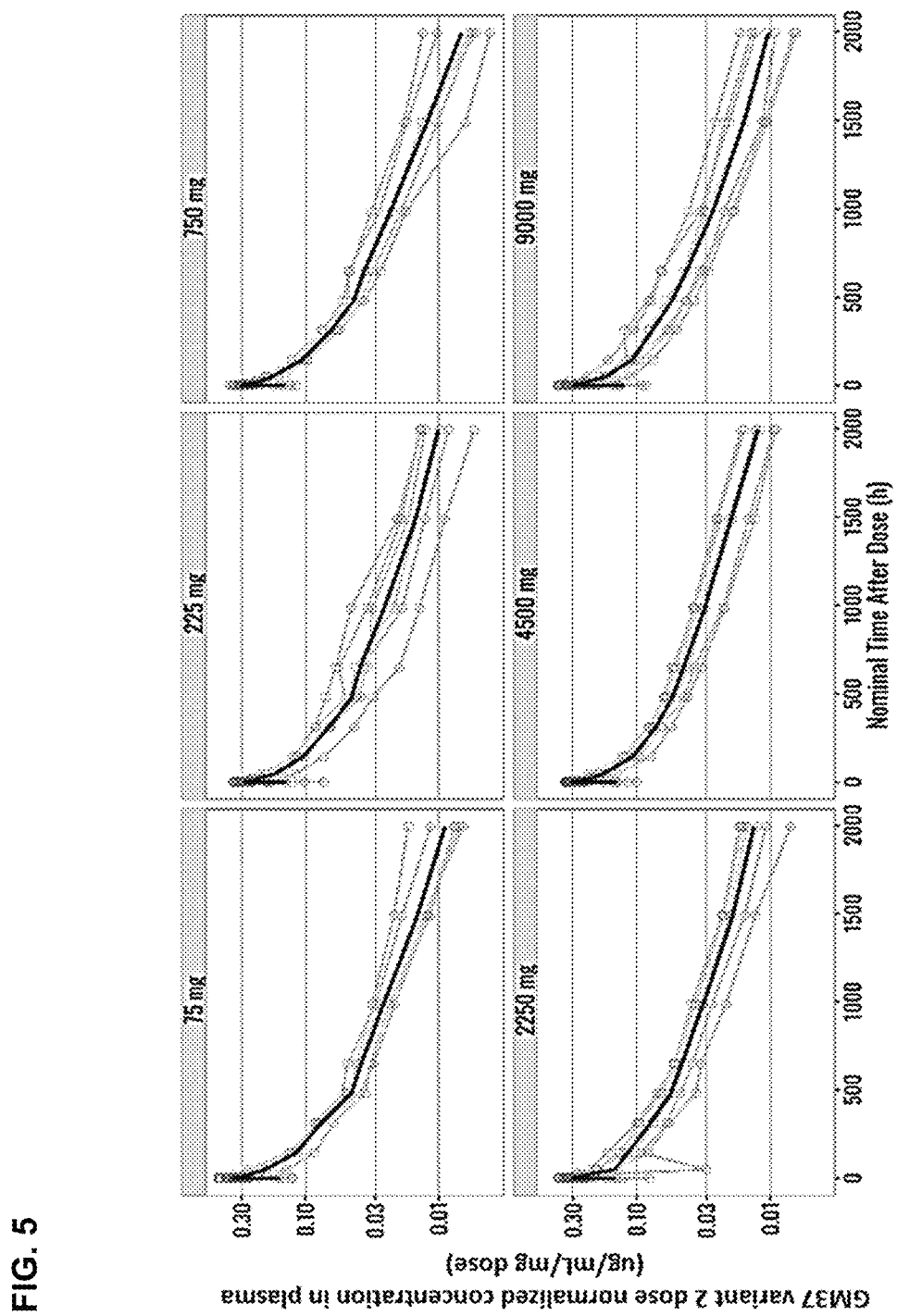
FIG. 5 shows the dose-normalized GM37 variant 2 plasma concentrations versus time (log-scale) at each dose level.

The dose-normalized GM37 variant 2 plasma concentrations versus time (log-scale) are presented in FIG. 5 (all subjects); solid line is mean, grey line and circles are individual data. No obvious deviation from dose linearity was seen.

The overall PK profile of GM37 variant 2 was described by a three-compartment model with first order elimination from the central compartment. CL (clearance) and Vss (volume of distribution) were estimated to 0.254 L/day and 8.64 L, respectively. The GM37 variant 2 geometric mean terminal elimination t½ was estimated to 30.5 days (17.5% CV). IV was estimated to 16.1% CV for CL and 10.1% CV for V (central volume of distribution). The residual unexplained variability was low (6.91%). There was no significant relationship between predicted individual CL and dose, confirming the dose-proportional PK of GM37 variant 2. ADAs were detected in 3 of 41 subjects receiving GM37 variant 2; No apparent difference in GM37 variant 2 PK was seen in these subjects. Among the primary covariates (WT, HT, age, sex, race (including Japanese), albumin, and baseline alpha synuclein), only WT and HT had a statistically significant impact on the PK parameters.

WT had the largest impact on PK parameters with 25% lower CL in a reference subject with the 5th percentile of the baseline covariate value and 24% higher CL in a reference subject with the 95th percentile of the baseline covariate value. The impact of WT on exposure (AUCss and Cmax;ss) at steady state was considered modest (approximately 0.8 to 1.3-fold for AUCss) at the 5th and 95th percentiles of the baseline covariate distribution as compared to the reference subject (74.6 kg and 171 cm), supporting flat fixed dosing.

The final model demonstrated appropriate agreement between predicted and observed data values.

Figure 9:
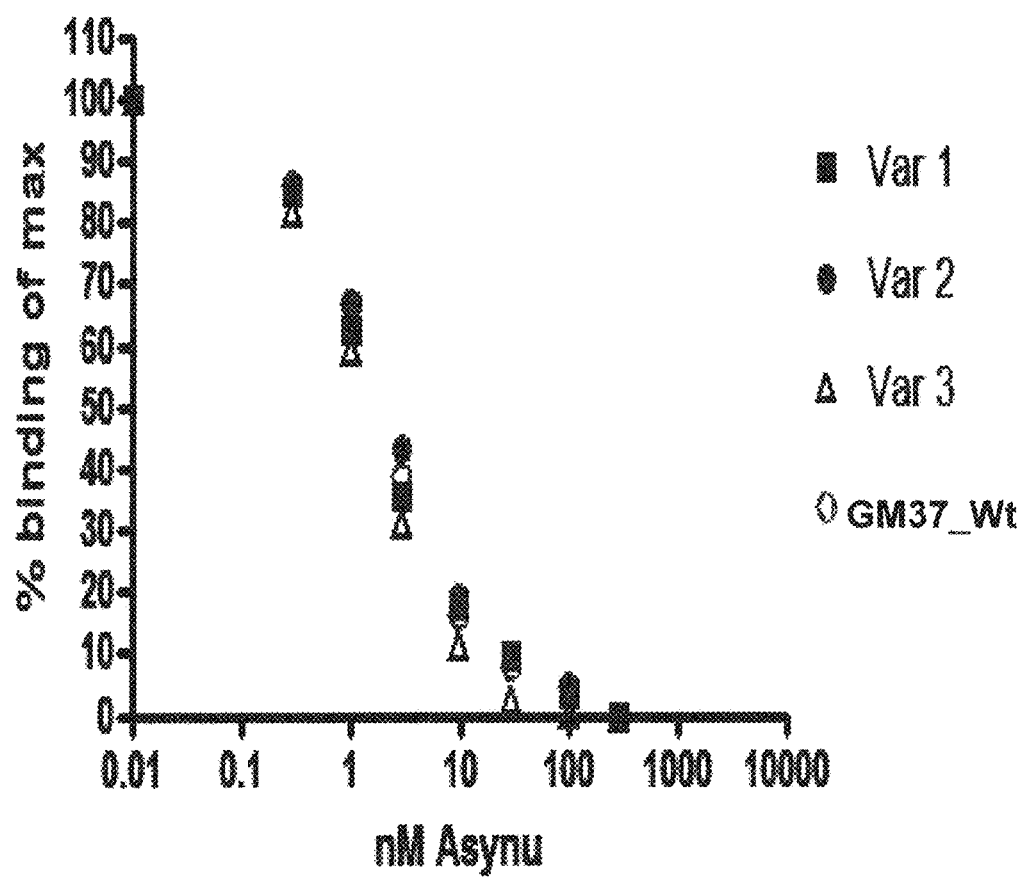
FIG. 9 shows a competition ELISA measuring binding of four antibodies GM37 wt, GM37 var 1, GM37 var 2 and GM37 var 3 to human alpha synuclein. Plates coated with alpha synuclein are used to detect the amount of antibody remaining after preincubation in solution of each antibody (0.3 µg/mL) with increasing concentration of alpha synuclein (0-1000 nM). All four antibodies show similar binding to alpha synuclein.

Example 6—Antibodies for Use According to the Invention and their Binding to Human Alpha Synuclein Using a competition ELISA experiment we evaluated the impact that change at residue 54 would have on the ability of GM37 wt to bind alpha synuclein in solution. By evaluating the concentration of synuclein able to inhibit binding of the antibody to synuclein coated ELISA plates we showed that GM37 variants maintained the same binding properties and bind to alpha synuclein with and IC50s of 1-2 nM in this specific assay design (FIG. 9). The competition assay was performed using preincubation of a fixed concentration (0.3 µg/ml) of each of the following antibodies, GM37 (named GM 37 wt), GM37 variant1, GM37 variant2 and GM37 variant3 with a range of 0-1000 nM human alpha synuclein for 60 minutes at room temperature. The remaining unbound antibody was captured and measured on ELISA plates coated with 100 ng/ml of recombinant human alpha synuclein using an anti-human detection antibody by electro-chemiluminescence (MSD, Gathersburg, MD). The IC50s of the interaction are 1.9 nM, 1.6 nM, 2.1 nM and 1.4 nM for GM37, GM37 variant 1, GM37 variant 2 and GM37 variant 3, respectively in this specific assay (as determined using Prism Graphpad®).

Example 6A—Determination of Exact KD for Binding of GM37v2 to Monomeric Alpha Synuclein The exact KD value of the binding of GM37 variant 2 to monomeric α-synuclein was measured using repeated SPR analyses with a standardized set-up.

The SPR set-up were as follows: The equivalence of ~3000 RU anti-human IgG antibody were amine coupled to the alpha synuclein antibody on a CM4 chip following the protocol from GE (Cat #BR1008-39 from GE Healthcare). The alpha synuclein antibody was diluted to 1 µg/mi and injected with contact time of 30 s to obtain capture levels of ~ 50-200 RU, using either PBS-P with additives: 1 mg/ml BSA (A7979-Sigma Aldrich) and additional 0.05% P20 (total 0.1%) or HBS-P with additives: 5 mg/ml BSA, and additional 0.05% P20 (total 0.1%) as running buffer.

Monomeric α-synuclein was used in a 3-fold dilution series from max 600 nM. The removal (regeneration) of captured antibodies was achieved by injection of 3M MgCl2 regeneration buffers provided in the capture Ab kits (GE Healthcare). The assay running was either PBS-P with additives: 1 mg/ml BSA (A7979-Sigma Aldrich) and additional 0.05% P20 (total 0.1%) or HBS-P with additives: 5 mg/ml BSA, and additional 0.05% P20 (total 0.1%).

The data were analyzed using Biacore S200 Evaluation software 1.1. The KD and kinetic parameters were determination by global fit of sensorgrams to 1:1 kinetics model. The results of the repeated analysis are given in the table below:

| Experiment # | Antibody | Monomeric alpha synuclein | Ka (1/Ms) | Kd (1/s) | KD (nM) | Chi (RU) | Stoichiometry |
|---|---|---|---|---|---|---|---|
| 1 | GM37 variant 2 | Ab51189 | 7.40E+05 | 0.03 | 45 | 0.27 | 1.5 |
| 2 | GM37 variant 2 | Ab51189 | 4.60E+05 | 0.02 | 49 | 0.06 | 1.4 |
| 3 | GM37 variant 2 | Ab51189 | 6.70E+05 | 0.03 | 44 | 0.09 | 1.4 |
| 4 | GM37 variant 2 | Ab51189 | 5.80E+05 | 0.02 | 30 | 0.46 | 1.7 |
| 5 | GM37 variant 2 | Ab51189 | 1.00E+06 | 0.03 | 29 | 0.06 | 1.6 |
| 6 | GM37 variant 2 | Ab51189 | 1.43E+06 | 0.02 | 31 | 0.05 | 1.9 |
| 7 | GM37 variant 2 | Ab51189 | 7.20E+05 | 0.05 | 32 | 0.06 | 1.1 |
| 8 | GM37 variant 2 | Ab51189 | 6.90E+05 | 0.02 | 35 | 0.10 | 1.9 |
| 9 | GM37 variant 2 | Ab51189 | 7.00E+05 | 0.02 | 28 | 0.08 | 1.8 |
| 10 | GM37 variant 2 | Ab51189 | 6.70E+05 | 0.02 | 33 | 0.16 | 1.7 |
| 11 | GM37 variant 2 | Ab51189 | 6.00E+05 | 0.02 | 35 | 0.08 | 1.5 |

Based on repeated SPR analyses using a standardized set-up, the binding of GM37 variant 2 to monomeric α-synuclein has an average measured KID of 36 nM (S.D 7 nM).

Similar KID values were found for binding of GM37 variant 2 to human, rabbit and rodent monomeric alpha synuclein (data not shown), and hence this parameter was stable and reproducible across measurements from different species. These data support that the modelling underlaying performed to reach the dosing regimens of the present invention are based on well-established binding properties of GM37v2 and hence support the validity of the estimations for e.g. CSF/ISF target engagement of aggregated alpha synuclein.

Figure 10:
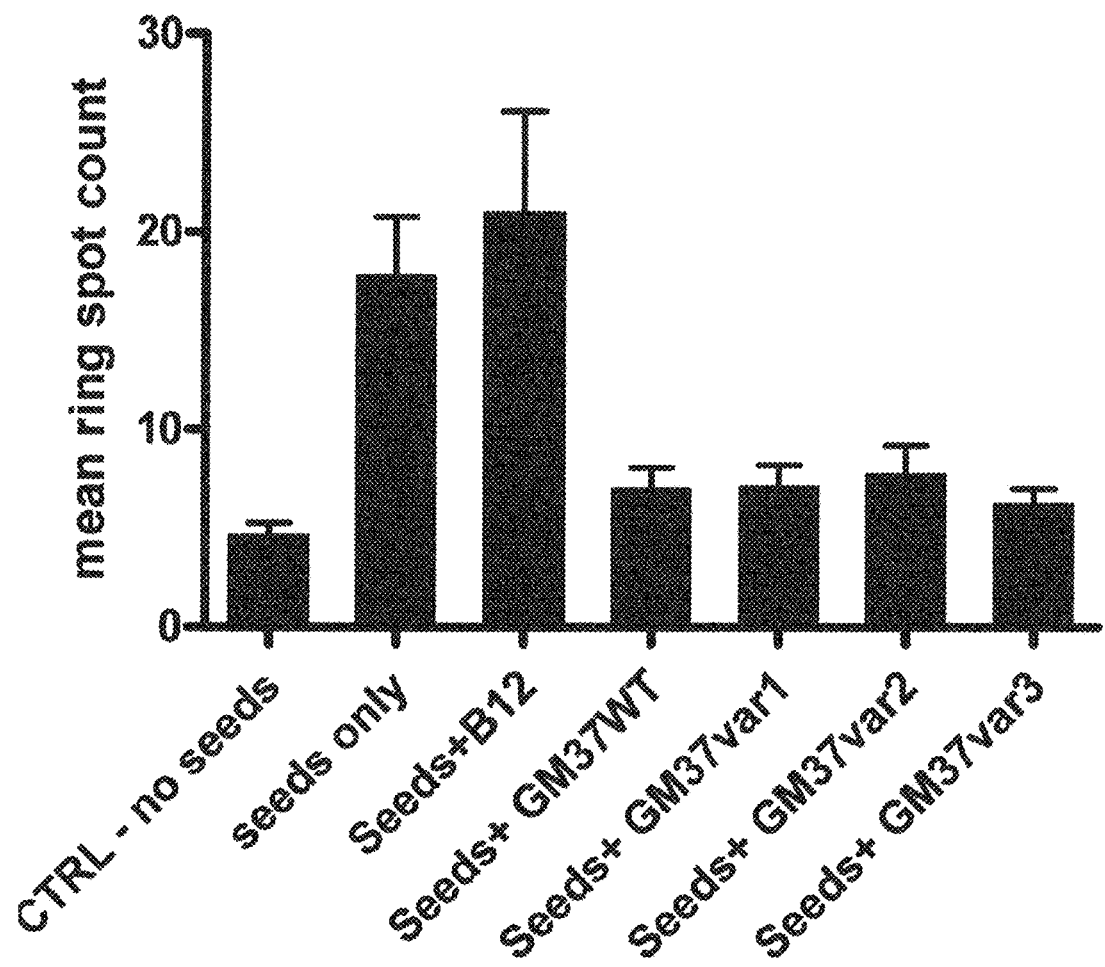
FIG. 10 compares the effect of anti-alpha synuclein antibodies on phosphorylated alpha synuclein levels in murine primary neurons treated with pathological alpha synuclein fibrillary seeds. Primary neurons were treated with seeds (10 ng) in the presence or absence of four antibodies for use according to the invention GM37, GM37 var 1, GM37 var 2 and GM37 var 3 (2 µg). Neurons were fixed and stained after 3 weeks and analysed by Cellomics ARRAYSCAN™ for alpha synuclein phosphoserine 129 positive spots. Cells treated with seeds alone or with seeds plus the isotype control antibody (B12) show significantly increased levels phosphorylation. Cells treated with GM37 wt and the 3 variants are able to inhibit phosphorylation of alpha synuclein, they all show the same level of phosphorylation as cells that did not receive seeds. Data is shown as mean±SD as determined from seven images per well in five wells. N=2.

Example 7—Ability of the Antibodies for Use According to the Invention to Block Synuclein Seeding Activity in a Culture of Primary Neurons The level of seeding was measured using an antibody specific for phospho-synuclein. GM37 (named GM 37 wt), GM37 variant1, GM37 variant2 and GM37 variant 3 were all able to block seeding as measured by the phospho-synuclein signal (FIG. 10). Furthermore, the level of inhibition was the same for all 4 antibodies. This cell based data further confirms the binding data that amino acid 54 in the VH domain is not required for binding affinity to human alpha synuclein or for inhibition of seeding in a primary cell based assay. Furthermore, we found that all three of these antibodies were capable of production using standard expression and purification methods. Interestingly one of the variants N54Q showed improvement in production over the other variants, which is of great importance when the antibody is to be produced commercially on large scale. These data support the possibility of reducing the potential risk of deamidation by replacing asparagine (N) with another amino acid without concern over the loss of potency.

Several studies have shown that exogenous addition of recombinant alpha synuclein fibrillar aggregates can enter cells and recruit endogenous alpha synuclein and induce alpha synuclein aggregation and phosphorylation in vitro and in vivo, which resemble LB. (Volpicelli-Daley et al. 2011, Luk et al. 2012a, Luk et al. 2012b, Recasens et al. 2013, Peelaerts et al. 2015). To study seeding of endogenous mouse alpha synuclein by recombinant alpha synuclein seeds, mouse primary cortical neurons prepared as above are plated in 96 well plates (15,000 cells per well). On day 5 in vitro culture (DIV), 50% of media is changed and supplemented with cytosine arabinoside (final conc. of 1 uM). On DIV 6, half of the media is changed with glia conditioned media along with alpha synuclein fibrillary material, either crude fibril seeds or pure seeds. The crude fibril seeds are made from recombinant monomeric human alpha synuclein, which was isolated from bacteria and the monomers were filtered through an Amicon Ultra 100.000 cut off filter (Millipore cat. No UFC510096) and adjusted to concentration of 1 mg/ml in PBS, pH 7.4. To make fibril crude seeds, the monomer solution was incubated in thermomixer at 37C with continuous mixing (800 rpm) until plateau is reached (evaluated by daily measures with Thioflavin S). To minimize evaporation a drop of mineral oil was added to cover the solution. The total time for incubation was 5-7 days, The pure seeds are made from crude fibril seeds that are centrifuged to purify them and the aggregated pellet is resuspended in fresh PBS and sonicated. The antibodies are added once on DIV 6 along with alpha synuclein crude seeds. Half of the media in the primary neurons is replaced with glia conditioned media every week to maintain them up to DIV21. The neurons are fixed and stained for Phospho-synuclein using a rabbit antibody specific for phosphorylation of alpha synuclein at amino acid S129 (abcam 51253), followed by a fluorescently labelled anti-rabbit antibody, fluorescence is quantified using automated fluorescent microscopy, Cellomics Arrayscan. Nuclei were detected in one channel and defined the number of valid cells. Phosphorylated alpha synuclein spots were detected in another channel in a pre-defined ring-formed area surrounding the nucleus, thus representing the cytoplasm of the cells. The average number of spots per cell was calculated.

For fractionation studies cells were harvested in phosphate buffered saline solution (PBS) and centrifuged. Pellet was resuspended in 1% triton buffer with protease inhibitors. Samples were kept on ice for 15 min. followed by sonication. The samples were centrifuged at 100,000×g for 30 min. at 4 C. The supernatant is collected and labelled as soluble fraction. The pellet was washed once in triton buffer and re-suspended in 1% SDS buffer followed by sonication. Samples were centrifuged again at 100,000×g for 30 min. The supernatant is collected as insoluble fraction. The protein concentrations were measured and samples were run on 4-12% SDS_PAGE gel, blotted on membranes and alpha synuclein and phosphorylated alpha synuclein (S129P) are detected by 4B12/1904 antibody (Thermo scientific: MA1-90346-human synuclein), S129P-asyn antibody (abcam 51253) and mouse synuclein antibody (cell signalling-D37A6), respectively.

To test if antibodies can inhibit seeding, alpha synuclein seeds were used at conc. of 6.6 nM (10 ng/well). Different concentration of antibody and alpha synuclein seeds were added together on DIV 6, to make a dose response (starting from highest antibody conc. at 133 nM down to 133 µM). The neurons were again fixed and stained for Phospho-synuclein (abcam 51253) and fluorescence from cells was quantified using automated fluorescent microscopy, Cellomics arrayscan. The spots/puncta per cell were counted in Cellomics arrayscan. Both antibody GM37, GM37v2 and antibody GM285 reduced alpha synuclein phosphorylation in neurons in a dose dependent manner with similar maximal inhibition for GM37, GM37v2 and 285 (around 70-75%) and IC50 around 5 nM. Fractionation of the cellular proteins to soluble and insoluble fraction after treatment with antibody at the highest concentration (133 nM) shows that both antibodies GM37, GM37v2 and GM285 inhibited the truncation of the recombinant crude seeds and accumulation of C terminally truncated fragment (CT a-syn), and reduced the accumulation of phosphorylated endogenous mouse alpha synuclein and aggregated forms of mouse alpha synuclein in the insoluble fraction.

Example 7A—Free and Total Alpha Synuclein Quantification in Human CSF and Plasma Free (unbound) and total alpha synuclein levels were measured in CSF and plasma using an ECLIA (MSD) quantification assay. An MSD Gold streptavidin plate was washed three times with wash buffer (300 µl/well), followed by well emptying. In the free assay, all wells were subsequently blocked with 150 µl Superblock T20 for 1 hr at room temperature, 500 RPM, followed by addition of 50 µl of 1 ng/ml coating antibody (GM37v2) in PBS. In the total assay, the plate was simultaneously blocked and coated with 25 uL of 1 ng/ml coating antibody (GM37v2) in diluent 49. After 1 hr of incubation at room temperature, 500 RPM, the plate was again washed three times with wash buffer (300 uL/well), followed by well emptying. Next 25 ul detection antibody was added to all wells together with 25 uL diluted samples, alpha synuclein calibration curve (4 ng/mL-0.030 ng/ml) and QC samples in duplicates. In the free alpha synuclein assay the samples were prediluted 5× in diluent 49, whereas in the total alpha synuclein assay, the samples were pre-diluted 500× in diluent 49 followed by 10 min heat treatment at 95° C., 500 RPM and centrifugation of the samples at 13.000 RPM at room temperature for 10 min prior to transfer to the assay plates. Samples, calibrators, QC samples and detection mAb were incubated for 2 hrs at room temperature, 500 RPM. Subsequently, the plate was washed three times with wash buffer (300 µL/well), followed by well emptying and addition of 150 µl Read Buffer T (1×) to all wells of the plate. The ELC response was measured using a QuickPlex SQ 120 within 5 minutes after the read buffer was added to the MSD streptavidin plate. Alpha synuclein sample levels were interpolated using a 4 PL curve fit of the calibration curve.

Example 8—Methods of Confirming Clinical Efficacy of the Dosage Regimens Provided by the Invention for Treating Synucleinopathies or Prodromal Synucleinopathies The clinical efficacy or treatment effect of the dosage regimens provided by the invention can for example be confirmed by conducting a randomized, double-blind, placebo-controlled clinical trial. Such trial may investigate the efficacy or treatment effect of antibodies of the invention administered in a dose above 700 mg and below 7000 mg every 3-5 week by intravenous infusion. Said infusion may be done over a time period of 15 minutes ±5 minutes, 30 minutes ±10 minutes or another suitable timeframe. The dosage regimens to be tested may be fixed doses of the invention, such as 1050 mg, 2100 mg and/or 4200 mg administered intravenously about every 4 weeks for 24 weeks, 48 weeks, 72 weeks, 96 weeks or more in a suitable formulation such as the liquid pharmaceutical compositions of the invention. Such efficacy can be measured as the ability of the antibody administered (such as GM37v2) to delay or slow the disease progression of the synucleinopathy (such as MSA) or to delay disease onset if the patient suffers from prodromal synucleinopathy. In such clinical trial the control group, i.e., the non-active arm of the trial can be a classic placebo arm included in the trial where a group of patients are administered a suitable placebo treatment. However, data from the active arm of such trial may also be compared against historical data on disease progression obtained from relevant patients suffering from the type of synucleinopathy treated in the trial. Finally, the treatment effect in the active arm of such trial may be quantified by comparing the disease progression in the treated patients with a group of placebo-controlled patients and this control group may further be enriched by historical data on disease progression obtained from patients with synucleinopathy. An example of such clinical trial is NCT05104476 (The National Clinical Trial number), which protocol is hereby incorporated by reference.

Patients to be included in such trial are patients suffering from synucleinopathies or prodromal synucleinopathies as defined by the current consensus diagnostic criteria. Such patients may be diagnosed with MSA, such as possible MSA, probable MSA, clinically established MSA, clinically probable MSA, MSA type C or MSA type P; PD; or DLB according to known diagnostic methods and criteria or exhibiting clinical markers for prodromal synucleinopathies such as RBD or other prodromal markers described herein.

The outcome measures to quantify clinical efficacy or treatment effect can be any suitable way of measuring slowing or delay in disease progression, for example as assessed by longitudinal changes from baseline in the Unified Multiple System Atrophy Rating Scale (UMSARS) Part I and Part II Total score (UMSARS TS) or in the modified UMSARS (mUMSARS) or in the abbreviated UMSARS (aUMSARS) up to End-of-Treatment (EoT), i.e. at the end of the treatment period of 24 weeks, 48 weeks, 72 weeks, 96 weeks or more.

The outcome measures to quantify clinical efficacy or treatment effect can also be measuring slowing or delay in disease progression, for example as assessed by longitudinal changes from baseline in the UMSARS Part I, modified UMSARS (mUMSARS) and/or UMSARS Part II scores up to EoT. Such disease progression could also for example be assessed as the change from baseline up to EoT in UMSARS TS, UMSARS Part I, mUMSARS and/or UMSARS Part II scores. The disease progression can also for example be assessed by longitudinal changes from baseline in the abbreviated UMSARS (aUMSARS) up to EoT or as change from baseline in Brain Volume, as Measured by Volumetric MRI (vMRI) or as change from baseline in Neurofilament Light Chain (NfL) blood concentrations.

The clinical efficacy or treatment effect can for example also be evaluated at EoT as change from baseline in one or more parameter selected from: Schwab and England Activities of Daily Living (SE-ADL) Score; as change from baseline in Clinical Global Impression—Severity of Illness (CGI-S) Score; as change from baseline in Patient Global Impression—Severity of Illness (PGI-S) Score; as change from baseline in Observer-Reported Global Impression—Severity of Illness (OGI-S) Score; as change from baseline in Composite Autonomic Symptom Score Select Change (COMPASS Select Change) Score; as change from baseline in UMSARS Part IV Score; as change from baseline in Speech, Swallowing, Falls, and Walking, as assessed by the UMSARS Part I Item Scores; as change from baseline in Frequency, Cause, and Consequence of Falls, as assessed by the Fall Diary Periods; as change from baseline in EuroQol 5-Dimension, 5-Level (EQ-5D-5L) Score; as change from baseline in Brain Volume, as Measured by Volumetric MRI (vMRI); as change from baseline in Tissue Integrity, as Measured by Diffusion-Tensor Imaging (DTI) MRI; as change from baseline in Neurofilament Light Chain (NfL) blood concentrations; as change from baseline in heart rate, blood pressure, and orthostatic symptoms, as assessed in UMSARS Part III; as change from baseline in gait parameters or frequency of falls, as assessed by digital wearable sensor-based devices that are capable of tracking relevant gait parameters and/or registering falls; as change from baseline in cerebral blood flow, as measured by arterial spin labelling (ASL) MRI; as change from baseline in t-tau and NfL CSF concentrations; or as change from baseline in concentration of pathological species of α-synuclein in CSF.

During the trial plasma and CSF samples is be collected at various timepoints such as at Baseline and one or more of weeks 4, 6, 8, 12, 24, 36, 48, 60, 72, 88 and 96 to investigate biological markers and exposure levels of the administered antibody.

Experimental Section—Formulation Development

The pharmaceutical formulations of the present invention may be prepared and/or analysed and/or characterized by the methods such as analytical methods described below. These methods are all well known in the art of pharmaceutical sciences.

The examples and studies described below presents the work performed by the inventors of the present invention to identify a clinically suitable pharmaceutical formulation comprising the antibody GM37 variant 2 (GM37v2).

Generalized Description of Analytical Methods Used in Studies 1A, 1B and 1C Presented Below:

GP-HPLC

The gel permeation HPLC method was carried out on an Agilent 1200 HPLC system using a standardised TSK SWXL G3000 column. The mobile phase used was 0.2 M sodium phosphate at pH 7.0 at a flow rate of 1.0 mL/min. The sample injection volume was 50 uL. Protein loadings of approximately 250 ug were analysed using single determinations. The results were expressed to two decimal places as % monomer, % aggregate and % fragment in each sample.

Differential Scanning Calorimetry (DSC)

DSC was performed as per the instrument operating procedure. Samples were heated to 120° C. and the melting temp measured to determine the formulation stability.

Dynamic Light Scattering (DLS)

DLS was performed as per the instrument operating procedure. DLS was used to determine the hydrodynamic radius of a sample by applying the Stokes-Einstein equation. The particles present in the sample created time dependent scattering of light, due to Brownian motion and the DLS monitors the light scatter using a high sensitivity detector.

Analysis was performed on the Viscoteck 802 DLS, with associated OmniSIZE 2.0 software. Samples were analysed in ten replicates.

Particulates

The absorbance of each sample at 340 nm and 620 nm was recorded as an indication of particulate levels and turbidity. Determinations were made singly using 1 mL of undiluted product. The product formulation buffer was used as a blank with the absorbance readings of the product taken at 340 nm and 620 nm by one operator only. Results were expressed to 3 decimal places.

Subvisible Particle Analysis

The particle counts were tested by light obscuration and the results reported according to the principals of USP<788> where required. 1 mL of sample was used as a wash through and discarded. Three readings were then taken using 1 mL of sample each and a cumulative result reported.

SDS-PAGE (Reduced and Non-Reduced)

Analysis using Novex Pre-cast Minigels, SimplyBlue SafeStain and the Bio-Rad GS-800 Imaging Densitometer.

Samples were denatured by heating and treatment with sodium dodecyl sulphate. For reduced analysis, the disulphide bonds were disrupted with 2-mercaptoethanol.

Polypeptides were separated on the basis of molecular size by electrophoresis through 4% to 20% gradient SDS PAGE gels. Following separation, the protein bands were visualised by SimplyBlue™ Safetstain (Coomassie Blue G-250). Polypeptide bands were quantified by white light densitometry using the Bio-Rad GS-800 densitometer. The standard load mass was 3 ug (non-reducing) or 5 ug (reducing).

Example A—pH and Buffer Type of Formulations

Example A focuses on identifying the most favorable pH range and buffer type for GM37v2 formulations. Example A consists of two separate studies hereafter denoted Study 1A testing eight formulation candidates and Study 2A testing 16 formulation candidates.

Study 1A: pH and Buffer Type of Formulations

Eight formulation candidates, Formulation 1 to Formulation 8, were investigated and denoted F1-F8 (Table 1).

TABLE 1

Formulations investigated in study 1A of impact of pH/buffer type on GM37v2 formulations

| pH Formulation ID | Formulation Buffer | pH of Formulation |
|---|---|---|
| F1 | 25 mM Sodium acetate | 4.5 |
| F2 | 25 mM Sodium acetate | 5.0 |
| F3 | 25 mM Sodium acetate | 5.5 |
| F4 | 25 mM Sodium citrate | 6.0 |
| F5 | 25 mM Histidine | 6.0 |
| F6 | 25 mM Sodium citrate | 6.5 |
| F7 | 25 mM Sodium phosphate | 7.0 |
| F8 | 25 mM Sodium phosphate | 7.5 |
| Control (SC) | PBS | 7.4 |

The stability of GM37v2 was assessed in the eight formulation candidates at the target storage temperature 5° C.±3 and at elevated temperature 40° C.±2 at not more than 30% RH. The GM37v2 concentration in each formulation buffer was 30 mg/ml.

The stability of each formulation was measured by various well-known methods at baseline (Time zero, 0 weeks; T=0) and after one week (T=1, 1 week) for each formulation. Further, the stability study for each formulation included application of the following analytical methods (Table 2):

TABLE 2

Analytical methods to assess stability:

| | Time point | | |
|---|---|---|---|
| Analytical method | Time zero | 1 week @ 5° C. | 1 week @ 40° C. |
| GP-HPLC | X | X | X |
| DSC | X | X | X |
| DLS | X | X | X |

GP-HPLC = Gel Permeation-High Performance Liquid Chromatography
DSC = Differential Scanning Calorimetry
DLS = Dynamic Light Scattering The results of this stability study are summarized below.

TABLE 3

GP-HPLC - Percentage purity measured by amount of aggregate (% A), fragment (% F) and monomer (% M), results summary study 1A:

| | Timepoint (weeks) | | | | | | | | |
|---|---|---|---|---|---|---|---|---|---|
| | T = 0 | | | T = 1 | | | | | |
| | | | | +5° C. | | | +40° C. | | |
| Formulations | % M | % A | % F | % M | % A | % F | % M | % A | % F |
| F1 | 99.44 | 0.54 | 0.02 | 99.39 | 0.59 | 0.02 | 99.13 | 0.42 | 0.45 |
| F2 | 99.40 | 0.58 | 0.02 | 99.45 | 0.53 | 0.02 | 99.31 | 0.52 | 0.17 |
| F3 | 99.25 | 0.74 | 0.02 | 99.25 | 0.74 | 0.02 | 98.89 | 0.98 | 0.13 |
| F4 | 99.25 | 0.74 | 0.01 | 99.25 | 0.74 | 0.02 | 99.00 | 0.89 | 0.12 |
| F5 | 99.33 | 0.65 | 0.02 | 99.32 | 0.66 | 0.02 | 99.26 | 0.61 | 0.13 |
| F6 | 99.21 | 0.77 | 0.02 | 99.22 | 0.76 | 0.02 | 98.81 | 1.07 | 0.12 |
| F7 | 99.10 | 0.88 | 0.02 | 99.09 | 0.89 | 0.02 | 98.33 | 1.50 | 0.18 |
| F8 | 99.06 | 0.92 | 0.02 | 99.02 | 0.96 | 0.02 | 98.15 | 1.64 | 0.21 |
| Control | 99.05 | 0.94 | 0.02 | 99.09 | 0.90 | 0.01 | N/A | N/A | N/A |

M = Monomer
A = Aggregate
F = Fragment
N/A = Not Applicable

Initial aggregate level was pH dependent. Starting aggregate levels were higher at pH 7.5 and pH 7.0 in 25 mM sodium phosphate buffer (F8 (study 1A) and F7 (study 1A) respectively), compared to the other formulations at T=0 weeks. Aggregate levels were also higher in 25 mM sodium citrate buffers at pH 6.0 and pH 6.5 (F4 (study 1A) and F6 (study 1A), respectively) compared to the other formulations at T=0 weeks.

The formulation containing 25 mM sodium acetate buffer at pH 5.5 (F3, study 1A) also demonstrated higher aggregate levels at T=0 weeks compared to the other 25 mM sodium acetate buffer formulations (F1 (study 1A) and F2 (study 1A)). No marked difference in fragment levels at T=0 weeks was observed between formulations.

All formulations demonstrated no marked change in % monomer, % aggregates and % fragments on storage at +5° C. for one week compared to their respective result at T=0 weeks.

Aggregation at +40° C. was pH and buffer dependent.

Formulations F7 (study 1A) and F8 (study 1A) (25 mM sodium phosphate at pH 7.0 and 7.5 respectively) demonstrated the highest increase in aggregates on storage at +40° C. for one week compared to their result at T=0 weeks. Formulation F6 (study 1A) (25 mM sodium citrate at pH 6.5), formulation F3 (study 1A) (25 mM sodium acetate at pH 5.5) and formulation F4 (study 1A) (25 mM sodium citrate at pH 6.0), also demonstrated an increase in aggregates after one week at +40° C. but to a lesser extent than formulations F7 (study 1A) and F8 (study 1A).

Formulations F1 (study 1A), F2 (study 1A) and F5 (study 1A) demonstrated no marked change in aggregate levels after storage at +40° C. for one week compared to their respective T=0 weeks result.

Formulation F1 (study 1A) (25 mM sodium acetate pH 4.5) demonstrated a marked change in fragment level after storage at +40° C. after one week compared to the T=0 weeks result from 0.02% to 0.45%.

All other formulations demonstrated a slight increase in fragment levels (~0.1%) after storage at +40° C. after one week compared to their respective T=0 weeks result.

By GP HPLC formulation F2 (study 1A) (25 mM sodium acetate buffer at pH 5.0) and formulation F5 (study 1A) (25 mM Histidine buffer at pH 6.0) presented as the most suitable formulation candidates for further development.

Thermal Stability Results Summary Study 1A

TABLE 4

DSC Differential Scanning Calorimetry

| Formulation | Unfolding Events | Melting Temperature (° C.) 1 d · p T = 0 |
|---|---|---|
| Formulation 1 | Tm1 | 63.9 |
|  | Tm2 | 69.9 |
|  | Tm3 | 75.3 |
|  | Tm4 | 81.5 |
| Formulation 2 | Tm1 | 68.4 |
|  | Tm2 | 71.0 |
|  | Tm3 | 77.5 |
|  | Tm4 | 84.4 |
| Formulation 3 | Tm1 | 69.2 |
|  | Tm2 | 71.4 |
|  | Tm3 | 77.0 |
|  | Tm4 | 85.4 |
| Formulation 4 | Tm1 | 67.6 |
|  | Tm2 | 70.4 |
|  | Tm3 | 77.5 |
|  | Tm4 | 85.0 |
| Formulation 5 | Tm1 | 69.7 |
|  | Tm2 | 71.5 |
|  | Tm3 | 77.9 |
|  | Tm4 | 84.8 |
| Formulation 6 | Tm1 | 70.3 |
|  | Tm2 | 76.5 |
|  | Tm3 | 84.9 |
| Formulation 7 | Tm1 | 70.3 |
|  | Tm2 | 76.3 |
|  | Tm3 | 85.0 |
| Formulation 8 | Tm1 | 69.8 |
|  | Tm2 | 74.9 |
|  | Tm3 | 84.9 |
| Study Control | Tm1 | 89.1 |
|  | Tm2 | 73.5 |
|  | Tm3 | 84.5 |

Tm1 = Melting temperature of unfolding event 1
Tm2 = Melting temperature of unfolding event 2
Tm3 = Melting temperature of unfolding event 3
Tm4 = Melting temperature of unfolding event 4

Four unfolding events were observed for formulations F1 (study 1A), F2 (study 1A), F3 (study 1A), F4 (study 1A) and F5 (study 1A) at T=0 weeks. Three unfolding events were observed for formulations F6 (study 1A), F7 (study 1A) and F8 (study 1A).

It is expected that the DSC profile for an IgG1 antibody will typically present three unfolding events. In this instance at low pHs between pH 4.5 to 6.0 a slightly more complex pattern was observed resulting in four unfolding events, which were not observed in the higher pH formulations between pH 6.5 to 7.5. This may have been due to different conformations of the product being stabilized at different pHs.

Formulation F1 (study 1A) (25 mM sodium citrate at pH 4.5) had the lowest melting temperature for the first, second and third unfolding events at T=0 weeks.

The formulations at pH 6.0 (F5, study 1A), pH 6.5 (F6, Study 1A) and pH 7.0 (F7, Study 1A), pH 7.5 (F8, Study 1A) had the highest melting temperatures at the first and second melting events detected in measurement.

The melting temperature for all unfolding events was pH dependent. Melting temperature increased with pH from pH 4.5 to pH 7.5.

By DSC pH 6.0, 6.5, 7.0 and 7.5 were concluded to demonstrate the highest predictive thermal stability.

High Molecular Weight Species Result Summary Study 1A

TABLE 5

Dynamic Light Scattering (DLS)

| | Timepoint (weeks) | | | | | |
|---|---|---|---|---|---|---|
| | T = 0 | | T = 1 | | | |
| | | | +5° C. | | +40° C. | |
| Formulations | Rh (nm) by intensity | % RSD by intensity | Rh (nm) by intensity | % RSD by intensity | Rh (nm) by intensity | % RSD by intensity |
| F1 | 5.55 | 15.9 | 5.57 | 20.3 | 5.70 | 30.3 |
| F2 | 5.47 | 17.0 | 5.65 | 22.0 | 5.82 | 23.3 |
| F3 | 5.64 | 23.4 | 5.58 | 19.3 | 5.80 | 24.0 |
| F4 | 5.94 | 24.0 | 5.81 | 23.2 | 5.86 | 24.4 |
| F5 | 5.55 | 19.4 | 5.55 | 20.2 | 5.75 | 27.8 |
| F6 | 5.87 | 22.6 | 5.78 | 19.9 | 5.78 | 20.0 |
| F7 | 5.78 | 21.1 | 5.55 | 19.4 | 5.74 | 18.7 |
| F8 | 5.88 | 25.6 | 5.81 | 21.5 | 5.98 | 24.9 |
| SC | 6.00 | 26.7 | 5.98 | 25.1 | NA | N/A |

Rh = Hydrodynamic radius
% RSD = % Radial size distribution

No high molecular weight species were detected in any of the formulations at T=0 weeks or after storage for one week at +5° C. and +40° C.

There was no marked difference between any of the formulations.

Study 2A: pH and Buffer Type of Formulations

In a second part of Example A, Study 2A, 16 different formulation candidates were prepared, denoted formulation number 1-16, covering a pH range of 4 to 7 (Table 6). This study examined the effects of pH and buffer, as different buffers were used for a given formulation candidate. In addition, the GM37v2 concentration was varied from 25 mg/ml to 150 mg/ml. Finally, different tonicity modifiers/stabilizers were evaluated, including Arginine/Glutamate combinations, which have been shown to modulate viscosity at high protein concentrations.

The actual pH values, GM37v2 concentrations, viscosities and osmolalities are listed in Table 7.

TABLE 6

Formulations investigated in study 2A (values in mg/mL for GM37v2 and in mM for excipients)

| Form No | pH | acetate | citrate | His | phosphate | NaCl | sorbitol | Arg | Glu | GM37v2 |
|---|---|---|---|---|---|---|---|---|---|---|
| 1 | 4.0 | 20 | 0 | 0 | 0 | 140 | 0 | 0 | 0 | 25 |
| 2 | 4.0 | 20 | 0 | 0 | 0 | 0 | 270 | 0 | 0 | 50 |
| 3 | 5.0 | 20 | 0 | 0 | 0 | 0 | 270 | 0 | 0 | 50 |
| 4 | 5.0 | 0 | 0 | 20 | 0 | 0 | 0 | 100 | 100 | 25 |
| 5 | 5.5 | 0 | 20 | 0 | 0 | 0 | 270 | 0 | 0 | 50 |
| 6 | 5.5 | 0 | 0 | 20 | 0 | 70 | 130 | 0 | 0 | 100 |
| 7 | 6.0 | 0 | 20 | 0 | 0 | 0 | 0 | 50 | 50 | 100 |

TABLE 6-continued

Formulations investigated in study 2A (values in mg/mL for GM37v2 and in mM for excipients)

| Form No | pH  | acetate | citrate | His | phosphate | NaCl | sorbitol | Arg | Glu | GM37v2 |
|---------|-----|---------|---------|-----|-----------|------|----------|-----|-----|--------|
| 8       | 6.0 | 0       | 0       | 0   | 20        | 0    | 0        | 100 | 100 | 150    |
| 9       | 6.0 | 6       | 0       | 20  | 0         | 140  | 0        | 0   | 0   | 50     |
| 10      | 6.5 | 0       | 20      | 0   | 0         | 0    | 130      | 50  | 50  | 50     |
| 11      | 6.5 | 0       | 0       | 0   | 20        | 140  | 0        | 0   | 0   | 100    |
| 12      | 6.5 | 0       | 0       | 20  | 0         | 0    | 0        | 100 | 100 | 150    |
| 13      | 7.0 | 0       | 0       | 0   | 20        | 0    | 270      | 0   | 0   | 100    |
| 14      | 7.0 | 0       | 0       | 20  | 0         | 70   | 0        | 50  | 50  | 150    |
| 15      | 5.5 | 0       | 0       | 10  | 0         | 70   | 0        | 50  | 50  | 150    |
| 16      | 5.5 | 0       | 0       | 40  | 0         | 70   | 130      | 0   | 0   | 50     |

TABLE 7

Viscosity and osmolality of the tested formulation candidates in study 2A

| Form No. | Actual pH | Actual GM37v2 mg/ml | Osmolality mOmol/kg solvent | Viscosity cP |
|----------|-----------|---------------------|------------------------------|--------------|
| 1        | 4.00      | 24                  | 293                          | 1.07         |
| 2        | 4.44      | 47                  | 301                          | 1.60         |
| 3        | 5.12      | 53                  | 314                          | 1.56         |
| 4        | 5/02      | 22                  | 231                          | 1.29         |
| 5        | 5.59      | 53                  | 340                          | 1.51         |
| 6        | 5.58      | 103                 | 311                          | 2.22         |
| 7        | 6.00      | 102                 | 288                          | 2.34         |
| 8        | 6.05      | 154                 | 280                          | 3.97         |
| 9        | 6.03      | 54                  | 307                          | 1.44         |
| 10       | 6.57      | 53                  | 158                          | 1.42         |
| 11       | 6.49      | 107                 | 305                          | 2.21         |
| 12       | 6.56      | 155                 | 274                          | 4.26         |
| 13       | 6.99      | 109                 | 358                          | 2.52         |
| 14       | 6.98      | 145                 | 305                          | 3.85         |
| 15       | 5.54      | 149                 | 296                          | 3.78         |
| 16       | 5.52      | 49                  | 331                          | 1.37         |

Osmolality Measurements

The osmolality of the solutions was measured using a freezing point depression instrument. The osmometer calibration is checked using the Clinitrol 290 (3MA029).

Viscosity Measurements

The Viscosity was measured using an m-VROC™ Viscometer by Rheosense with an AIO chip. The shear rates employed are specified with the results. The viscometer was temperature controlled using a ThermoCube thermoelectric chiller and the samples were delivered using a Hamilton 100 uL syringe (81060). The accuracy of the instrument was verified using neat Isopropyl alcohol and measured at 25° C.

Summary of Viscosity Results of Study 2A

The viscosity values roughly were grouped by GM37v2 concentration. At ~25 mg/mL, the viscosity values averaged 1.2 cP. At 50 mg/mL or so, the values increased to ~1.5 cP. With GM37v2 concentrations near 100 mg/ml, the average value increased to ~2.3. Finally, at ~150 mg/mL, the viscosity values ranged from 3.8 to 4.3. These viscosity levels are quite low for formulations comprising a monoclonal antibody, especially at high antibody concentrations. Thus, the colloidal stability and propensity to self-associate appears to be quite low for GM37v2 in the tested formulation candidates. These data also indicated to the inventors that clinically suitable high concentration formulations (>200 mg/mL) could be possible for GM37v2 which were further investigated.

Size Exclusion Chromatography (SEC) Measurements

SEC analysis was conducted on a Dionex UltiMate 3000 HPLC system equipped with a quaternary pump system and a variable wavelength detector. Briefly, the SE-HPLC method employs a Tosoh TSKgel G3000SWxL (#08541) HPLC column and a mobile phase of 50 mM sodium phosphate, 0.3 M sodium chloride, and pH of 7.0 with an isocratic flow at 1 mL/min with a column temperature of 20° C. and a detection wavelength of 220 nm. System suitability was assessed for the SE-HPLC method for each sequence over the course of these studies. The % CV for chromatographic attributes of the main peak (MP) (retention time, Peak area, and relative area) are all less than 2% CV and the total relative areas sum to 100%.

Cation Exchange Chromatography (CEX) Measurements

CEX HPLC analysis was conducted on a Dionex UltiMate 3000 HPLC system equipped with a quaternary pump system and a variable wavelength detector. Briefly, the CEX HPLC method employs a Dionex MabPac SCX-10, 4×250 mm (#074625) HPLC column with a flow rate of 1.5 mL/min, a column temperature of 35° C. and a detection wavelength of 220 nm. Samples for analysis were previously diluted to around 7 mg/mL in 0.2 M $NaH_2PO_4$. The gradient program for the CEX HPLC method uses a mobile phase A, B, and C. The gradient program is outlined below.

Mobile phase A: 20 mM sodium phosphate, 2 mM sodium chloride pH 5.8, 2.1 millisiemens.
Mobile phase B: 20 mM sodium phosphate, 2 mM sodium chloride, pH 8.0, 3.75 millisiemens.
Mobile phase C: 10 mM sodium phosphate, 1M sodium chloride, pH 6.0

Gradient Conditions for CEX HPLC:

| Time (min) | Mobile Phase A | Mobile Phase B | Mobile Phase C |
|------------|----------------|----------------|----------------|
| 0          | 100            |                |                |
| 5          | 100            |                |                |
| 6          | 60             | 40             |                |
| 35         |                | 100            |                |
| 45         |                | 100            |                |
| 46         |                |                | 100            |
| 53         |                |                | 100            |
| 54         | 100            |                |                |
| 65         | 100            |                |                |

System suitability was assessed for the CEX HPLC method for each sequence over the course of these studies. The % CV for chromatographic attributes of the main peak (MP) (retention time, peak area, and relative area) are all less than 2% CV.

Summary of Stability Results of Study 2A

The stability of the 16 formulation candidates was monitored using well known SEC and CEX chromatography techniques. TO is baseline, T2 is 2 weeks and T4 is 4 weeks (Table 8 and 9).

TABLE 8

Stability of the tested formulation candidates were measured by Size-exclusion chromatography (SEC)

| Form No. | Actual pH | Actual GM37v2 mg/ml | SEC t0 | t2/ 5 C. | t2/ 25 C. | t2/ 40 C. | t4/ 25 C. | t4/ 40 C. |
|---|---|---|---|---|---|---|---|---|
| 1 | 4 | 24 | 99.47 | 99.44 | 99.24 | 90.60 | 96.84 | 85.18 |
| 2 | 4.44 | 47 | 99.46 | 99.53 | 99.50 | 97.75 | 99.44 | 96.27 |
| 3 | 5.12 | 53 | 99.45 | 99.47 | 99.44 | 98.04 | 99.40 | 97.09 |
| 4 | 5.2 | 22 | 99.49 | 99.50 | 99.48 | 97.79 | 99.40 | 96.48 |
| 5 | 5.59 | 53 | 99.39 | 99.38 | 99.31 | 97.85 | 99.20 | 96.85 |
| 6 | 5.58 | 103 | 99.38 | 99.35 | 99.28 | 97.76 | 99.17 | 96.63 |
| 7 | 6 | 102 | 99.28 | 99.33 | 99.24 | 97.81 | 99.16 | 96.86 |
| 8 | 6.05 | 154 | 99.35 | 99.30 | 99.19 | 97.69 | 99.07 | 96.60 |
| 9 | 6.03 | 54 | 99.38 | 99.35 | 99.31 | 97.90 | 99.22 | 96.88 |
| 10 | 6.57 | 53 | 99.33 | 99.30 | 99.23 | 97.80 | 99.13 | 96.86 |
| 11 | 6.49 | 107 | 99.17 | 99.08 | 98.84 | 97.05 | 98.64 | 95.89 |
| 12 | 6.56 | 155 | 99.33 | 99.25 | 99.15 | 97.05 | 99.02 | 96.46 |
| 13 | 6.99 | 109 | 99.10 | 98.94 | 98.66 | 96.42 | 98.40 | 94.88 |
| 14 | 6.98 | 145 | 99.28 | 99.17 | 99.02 | 97.35 | 98.86 | 96.07 |
| 15 | 5.54 | 149 | 99.38 | 99.33 | 99.24 | 97.68 | 99.13 | 96.55 |
| 16 | 5.52 | 49 | 99.45 | 99.43 | 99.40 | 97.93 | 99.35 | 96.85 |

TABLE 9

Stability of the tested formulation candidates were measured by Cation exchange chromatography (CEX)

| Form No. | Actual pH | Actual GM37v2 mg/ml | CEX 10 | t2/ 5 C. | t2/ 25 C. | t2/ 40 C. | t4/ 25 C. | t4/ 40 C. |
|---|---|---|---|---|---|---|---|---|
| 1 | 4.00 | 24 | 73.8 | 73.3 | 68.5 | 51.8 | 64.0 | 42.0 |
| 2 | 4.44 | 47 | 73.9 | 73.7 | 71.2 | 58.2 | 69.0 | 46.7 |
| 3 | 5.12 | 53 | 74.0 | 73.9 | 72.2 | 61.3 | 7.1 | 50.6 |
| 4 | 5.20 | 22 | 73.9 | 73.5 | 71.3 | 60.1 | 69.8 | 49.8 |
| 5 | 5.59 | 53 | 73.9 | 73.7 | 72.0 | 60.2 | 70.5 | 49.1 |
| 6 | 5.58 | 103 | 74.2 | 73.9 | 72.7 | 63.9 | 71.8 | 55.5 |
| 7 | 6.00 | 102 | 74.2 | 74.1 | 73.0 | 65.1 | 72.0 | 56.7 |
| 8 | 6.05 | 154 | 74.2 | 74.0 | 73.1 | 64.6 | 72.0 | 56.2 |
| 9 | 6.03 | 54 | 74.3 | 74.2 | 73.5 | 66.6 | 72.4 | 60.0 |
| 10 | 6.57 | 53 | 74.4 | 74.3 | 73.6 | 66.2 | 72.4 | 57.9 |
| 11 | 6.49 | 107 | 74.2 | 73.9 | 73.1 | 65.9 | 72.0 | 58.1 |
| 12 | 6.56 | 155 | 74.5 | 74.3 | 73.0 | 65.3 | 71.4 | 56.8 |
| 13 | 6.99 | 109 | 73.7 | 73.9 | 72.0 | 57.8 | 69.8 | 43.7 |
| 14 | 6.98 | 145 | 74.3 | 74.0 | 72.4 | 63.7 | 70.3 | 52.9 |
| 15 | 5.54 | 149 | 74.1 | 73.9 | 72.7 | 63.8 | 71.4 | 55.1 |
| 16 | 5.52 | 49 | 74.2 | 73.8 | 72.7 | 63.5 | 71.6 | 55.0 |

Formulation F1 ((study 2A), pH 4, acetate) demonstrated significant degradation at elevated temperature, especially after four weeks. In addition, Formulation F13 ((study 2A), pH 7, phosphate) also exhibited reduced stability compared to the other compositions. In the CEX test Formulation 2 ((study 2A), pH 4, acetate) also demonstrated signs of accelerated degradation at 40° C. The optimal pH appeared to be near 6, based on this SEC and CEX data.

Conclusion/Summary of pH and Buffer Type Studies
Study 1A:

Based on the range of well-established physical and chemical stability indicating methods described above in Example A study 1A, two buffer and pH pairs were found suitable to proceed into further formulation development and optimization.

The two buffer and pH pairs were:

F5 (study 1A)—about 25 mM histidine and pH around 6.0, and F2 (study 1A)—about 25 mM acetate and around pH 5.0.

Histidine (Formulation 5, Study 1A) demonstrated better stability than citrate at pH 6.0 due to an increase in aggregates observed by GP-HPLC with sodium citrate at pH 6.0 (Formulation 4, Study 1A).

pH 6.5 (Formulation 6, Study 1A) was deemed to be suitable from the visual analysis results but GP-HPLC indicated an increase in aggregates that was not seen at pH 5.0 (Formulation 2, Study 1A) and pH 6.0 (Formulation 5, Study 1A).

As stated above, the buffer ions selected for the further development were histidine at pH 6.0 and sodium acetate at pH 5.0. In addition to these most favored formulation candidates, a single formulation containing sodium citrate at pH 5.0 was also included in the further development.

Study 2A:

Collectively, the well-established physical and chemical stability indicating methods described above in Example A study 2A, indicate that optimal pH is likely near 5.5 to 6.0. The viscosity remains very low even at GM37v2 concentration of 150 mg/ml. The best buffer appears to be Histidine, given this pH range. Of the excipients tested, NaCl may have some protective effects against chemical degradation, but Arginine/Glutamate may also be useful for improving physical stability.

Example B—Excipients of Formulations

Example B focuses on identifying the most favorable excipients for the clinically acceptable formulation of GM37v2. Example B consists of 2 separate studies hereafter denoted Study 1B testing 11 formulation candidates and Study 2B testing 20 formulation candidates.

Study 1B: Excipients of Formulations

The stability of GM37v2 was assessed in 11 formulations comprising various excipients at the target storage temperature 5±3° C. and at elevated temperature 40±2° C., as well as following agitation and freeze/thaw treatment. The GM37v2 concentration in each formulation was about 50 mg/mL.

The stability of each formulation was measured at baseline (Time zero, 0 months; T=0) and after one month (T=1, 1 month) for each formulation candidate.

TABLE 10

Formulations investigated in study 1B

| Excipient Formulation ID | Formulation composition |
|---|---|
| F1 | 25 mM histidine, 50 mM sodium chloride, pH 6.0 + 200 mM glycine + 0.02% Polysorbate 80 |
| F2 | 25 mM histidine, 100 mM sodium chloride, pH 6.0 + 100 mM sucrose |
| F3 | 25 mM sodium acetate, 50 mM sodium chloride, pH 5.0 + 200 mM glycine |
| F4 | 25 mM sodium acetate, 50 mM sodium chloride, pH 5.0 + 200 mM glycine + 0.02% Polysorbate 80 |
| F5 | 25 mM sodium acetate, 50 mM sodium chloride, pH 5.0 + 100 mM arginine |
| F6 | 25 mM sodium acetate, 50 mM sodium chloride, pH 5.0 + 100 mM arginine + 0.02% Polysorbate 80 |
| F7 | 25 mM sodium acetate, 50 mM sodium chloride, pH 5.0 + 200 mM sucrose |
| F8 | 25 mM sodium acetate, 50 mM sodium chloride, pH 5.0 + 200 mM sucrose + 0.02% Polysorbate 80 |
| F9 | 25 mM sodium acetate, pH 5.0 + 180 mM arginine + 0.02% Polysorbate 80 |
| F10 | 25 mM sodium acetate, pH 5.0 + 250 mM glycine + 0.02% Polysorbate 80 |
| F11 | 25 mM sodium citrate, 50 mM sodium chloride, pH 5.0 + 200 mM glycine + 0.02% Polysorbate 80 |
| SC | Study control, PBS 7.4 pH |

The stability study for each formulation included application of the following analytical methods:

TABLE 11

Analytical methods employed in study 1B:

| Analytical method | Time zero | 1 month @ 5° C. | 1 month @ 40° C. | Agitation | Freeze/thaw −70° C. |
|---|---|---|---|---|---|
| GP-HPLC | X | X | X | X | X |
| Particulates A$_{340}$ | X | X | X | X | X |
| Sub-visible particles | X | X | X | X | X |
| SDS-PAGE (non-reduced) | X | X | X | X | X |
| SDS-PAGE (reduced) | X | X | X | X | X |
| DSC | X | X | X | X | X |
| DLS | X | X | X | X | X |

Agitation Measurements:

The agitation protocol was initiated at T=0 months. Samples were agitated using a rotating agitator set to 30 rpm for 48 hours at +5° C. Post agitation the samples were stored at +5° C. until testing.

Freeze/Thaw Measurements:

The freeze/thaw protocol was initiated at T=0 months. Samples were subjected to three freeze/thaw cycles consisting of approximately 18 hours at −70° C. followed by approximately 4-6 hours at room temperature. After freezing for the third time, the samples remained in the freezer until testing.

Low level of aggregate observed at T=0 months and after 1 month at +5° C. for all formulations.

Fragment level <LOQ (0.01%) was observed at T=0 months and after 1 month at +5° C. for all formulations.

No change in any of the formulations for monomer purity, peak area or height after agitation at +5° C.

No change in any of the formulations for monomer purity, peak area or height after freeze/thaw at −70° C. with the exception of F10 (study 1B). Aggregate level increased to 3.05%. No change in fragment levels.

At T=1 month formulations F1 (study 1B), F4 (study 1B), F6 (study 1B) and F9 (study 1B) demonstrated a marked change in % aggregates at +40° C.

At T=1 month all formulations demonstrated a marked change in % fragments at +40° C. with the highest percentage of fragments observed in formulations F5 (study 11), F6 (study 1B), F9 (study 1B) and F11 (study 1B).

Formulations with PS80 (F4 (study 1B), F6 (study 1B), and F8 (study 1B)) were observed to have a higher percentage of aggregates versus formulation without PS80 (F3 (study 1B), F5 (study 1B) and F7 (study 1B)) at both T=0 month and T=1 month. However, F11 (study 1B) that also had PS80 demonstrated the lowest amount of aggregates at T=1 month stored at +40° C.

Sodium chloride has a positive effect on the level of aggregates (F3-F8 (study 1B) verses F9 (study 1B)).

Arginine has a negative effect on the level of fragments (F5 (study 1B), F6 (study 1B) and F9 (study 1B)), however F11 (study 1B) which had no arginine also presented a high level of fragments.

Citrate buffer has a positive effect on aggregate levels compared to acetate buffer at pH 5.0 (F11 (study 1B) versus F4 (study 1B)).

Lowest amount of aggregates and fragments was seen in formulation F2 (study 1B) after storage at +40° C. for T=1 month.

TABLE 12

GP HPLC - Percentage purity

| Timepoint | | Data | F1 | F2 | F3 | F4 | F5 | F6 | F7 | F8 | F9 | F10 | F11 | SC |
|---|---|---|---|---|---|---|---|---|---|---|---|---|---|---|
| T = 0 | +5° C. | % aggregates | 0.85 | 0.72 | 0.70 | 0.82 | 0.70 | 0.82 | 0.69 | 0.83 | 0.82 | 0.76 | 0.81 | 1.03 |
| | | % monomer | 99.13 | 99.28 | 99.28 | 99.16 | 99.27 | 99.16 | 99.28 | 99.15 | 99.16 | 99.22 | 99.17 | 98.96 |
| | | % fragment | <LOQ | <LOQ | <LOQ | <LOQ | <LOQ | <LOQ | <LOQ | <LOQ | <LOQ | <LOQ | <LOQ | <LOQ |
| | +5° C. Agitation | % aggregates | 0.83 | 0.72 | 0.71 | 0.80 | 0.69 | 0.81 | 0.71 | 0.82 | 0.82 | 0.76 | 0.80 | |
| | | % monomer | 99.15 | 99.26 | 99.27 | 99.18 | 99.28 | 99.17 | 99.27 | 99.18 | 99.16 | 99.22 | 99.18 | |
| | | % fragment | <LOQ | <LOQ | <LOQ | <LOQ | <LOQ | <LOQ | <LOQ | <LOQ | <LOQ | <LOQ | <LOQ | |
| | −70° C. Freeze/thaw | % aggregates | 0.86 | 0.74 | 0.73 | 0.88 | 0.70 | 0.81 | 0.72 | 0.84 | 0.82 | 3.05 | 0.81 | |
| | | % monomer | 99.12 | 99.24 | 99.25 | 99.10 | 99.28 | 99.17 | 99.26 | 99.14 | 99.16 | 96.93 | 99.17 | |
| | | % fragment | <LOQ | <LOQ | <LOQ | <LOQ | <LOQ | <LOQ | <LOQ | <LOQ | <LOQ | <LOQ | <LOQ | |
| T = 1 M | +5° C. | % aggregates | 0.85 | 0.77 | 0.74 | 0.84 | 0.74 | 0.81 | 0.75 | 0.84 | 0.82 | 0.77 | 0.83 | 0.99 |
| | | % monomer | 99.13 | 99.21 | 99.24 | 99.13 | 99.24 | 99.16 | 99.22 | 99.13 | 99.15 | 99.20 | 99.14 | 98.99 |
| | | % fragment | <LOQ | <LOQ | <LOQ | <LOQ | <LOQ | <LOQ | <LOQ | <LOQ | <LOQ | <LOQ | <LOQ | <LOQ |
| T = 1 M | +40° C. | % aggregates | 1.48 | 0.94 | 1.01 | 1.48 | 0.88 | 1.24 | 0.89 | 1.12 | 1.86 | 1.13 | 0.78 | |
| | | % monomer | 97.54 | 98.19 | 97.74 | 97.15 | 97.05 | 96.49 | 97.89 | 97.52 | 95.85 | 97.83 | 97.09 | |
| | | % fragment | 0.98 | 0.87 | 1.24 | 1.37 | 2.08 | 2.27 | 1.42 | 1.36 | 2.29 | 1.04 | 2.12 | |
| | | % aggregates change to T = 0 | 0.63 | 0.22 | 0.31 | 0.66 | 0.18 | 0.42 | 0.20 | 0.29 | 1.04 | 0.37 | −0.03 | |
| | | % monomer change to T = 0 | −1.59 | −1.07 | −1.54 | −2.01 | −2.22 | −2.87 | −1.59 | −1.63 | −3.31 | −1.39 | −2.08 | |
| | | % fragment change to T = 0 | 0.98 | 0.87 | 1.24 | 1.37 | 2.06 | 2.27 | 1.42 | 1.36 | 2.29 | 1.04 | 2.12 | |

SC = Study control stored at −70° C.
LOQ = Limit of quantitation (0.1%)

TABLE 13

Particulates

| Timepoint | Data | F1 | F2 | F3 | F4 | F5 | F6 | F7 | F8 | F9 | F10 | F11 | SC |
|---|---|---|---|---|---|---|---|---|---|---|---|---|---|
| T = 0 | A340 | 0.108 | 0.111 | 0.115 | 0.107 | 0.114 | 0.102 | 0.116 | 0.097 | 0.096 | 0.092 | 0.112 | 0.223 |
|  | A620 | 0.008 | 0.012 | 0.014 | 0.010 | 0.011 | 0.007 | 0.016 | 0.006 | 0.007 | 0.029 | 0.010 | 0.028 |
| T = 0 +5° C. Agitation | A340 | 0.107 | 0.129 | 0.128 | 0.102 | 0.115 | 0.097 | 0.111 | 0.095 | 0.096 | 0.632 | 0.102 |  |
|  | A620 | 0.008 | 0.017 | 0.017 | 0.008 | 0.012 | 0.006 | 0.013 | 0.005 | 0.006 | 0.026 | 0.007 |  |
| T = 0 F/T | A340 | 0.256 | 0.117 | 0.112 | 0.098 | 0.108 | 0.102 | 0.111 | 0.093 | 0.097 | 0.636 | 0.100 |  |
|  | A620 | 0.103 | 0.013 | 0.012 | 0.007 | 0.009 | 0.008 | 0.013 | 0.006 | 0.007 | 0.028 | 0.006 |  |
| T = 1 M (+5° C.) | A340 | 0.131 | 0.145 | 0.171 | 0.120 | 0.145 | 0.114 | 0.122 | 0.108 | 0.096 | 0.091 | 0.120 | 0.235 |
|  | A620 | 0.013 | 0.024 | 0.035 | 0.014 | 0.024 | 0.011 | 0.018 | 0.010 | 0.006 | 0.009 | 0.013 | 0.042 |
| T = 1 M (+40° C.) | A340 | 0.369 | 0.218 | 0.185 | 0.287 | 0.176 | 0.193 | 0.159 | 0.209 | 0.261 | 0.241 | 0.302 |  |
|  | A620 | 0.026 | 0.026 | 0.029 | 0.034 | 0.027 | 0.019 | 0.021 | 0.027 | 0.030 | 0.032 | 0.089 |  |

SC = Study control
F/T = Freeze Thaw

At T=0 months A340 was higher in study control than the other formulations.

F10 (study 1B) demonstrated a marked increase in A340 after agitation and freeze/thaw.

F1 (study 1B) demonstrated a marked increase in A340 and A620 after agitation and freeze/thaw.

F1 (study 1B), F2 (study 1B), F3 (study 1B) and F5 (study 1B) demonstrated a slight increase in A340 after storage at +5° C. for T=1 month.

F1 (study 1B) and F11 (study 1B) demonstrated a marked increase in A340 after storage at +40° C. for T=1 month.

F7 (study 11B) demonstrated the least change in A340 after storage at +40 TC for T=1 month.

TABLE 14

Sub-visible particles, T = 0 (0 Months)

Particle concentration [particles per container]

| Formulation | ≥2 μm | ≥5 μm | ≥10 μm | ≥25 μm |
|---|---|---|---|---|
| F1 | 1565 | 320 | 75 | 0 |
| F2 | 3325 | 560 | 130 | 0 |
| F3 | 6108 | 1228 | 265 | 10 |
| F4 | 1758 | 365 | 145 | 10 |
| F5 | 3805 | 840 | 193 | 3 |
| F6 | 760 | 218 | 63 | 3 |
| F7 | 5355 | 1100 | 280 | 5 |
| F8 | 1228 | 238 | 75 | 3 |
| F9 | 660 | 205 | 70 | 0 |
| F10 | 525 | 155 | 43 | 3 |
| F11 | 910 | 265 | 75 | 0 |

TABLE 15

Sub-visible particles, T = 1 (1 Months)

Particle concentration [particles per container]

| Formulation | ≥2 μm | ≥5 μm | ≥10 μm | ≥25 μm |
|---|---|---|---|---|
| F1 | 610 | 123 | 45 | 5 |
| F2 | 975 | 173 | 50 | 3 |

TABLE 15-continued

Sub-visible particles, T = 1 (1 Months)

Particle concentration [particles per container]

| Formulation | ≥2 μm | ≥5 μm | ≥10 μm | ≥25 μm |
|---|---|---|---|---|
| F3 | 1835 | 385 | 85 | 10 |
| F4 | 1103 | 195 | 45 | 0 |
| F5 | 2940 | 538 | 143 | 18 |
| F6 | 465 | 95 | 20 | 0 |
| F7 | 1518 | 330 | 100 | 10 |
| F8 | 793 | 193 | 90 | 13 |
| F9 | 453 | 118 | 30 | 5 |
| F10 | 430 | 118 | 8 | 0 |
| F11 | 385 | 78 | 20 | 0 |

At T=0 months the formulations that demonstrated the highest number of particles per container were F2 (study 16), F3 (study 11B), F5 (study 16) and F7 (study 11B).

At T=1 month the formulations stored at +5 TC that demonstrated the highest number of particles per container were F3 (study 1B), F5 (study 1B), F7 (study 1B) and F8 (study 11B).

At T=1 month the formulations stored at +5° C. that showed the lowest number of particles per container were F6 (study 16), F10 (study 11B) and F11 (study 1B).

Formulations containing PS80 demonstrated consistently lower SVP levels than those without.

Formulation F2 (study 1B) is the only other formulation in the study without PS80, which displayed fewer sub-visible particles compared to F3 (study 1B), F5 (study 1B) and F7 (study 1B) at T=0 months and T=1 month, which indicates that pH 6.0 may be more suitable than pH 5.0.

TABLE 16

SDS PAGE (non-reduced) - Number of bands detected visually

| Timepoint | Temperature | F1 | F2 | F3 | F4 | F5 | F6 | F7 | F8 | F9 | F10 | F11 | SC |
|---|---|---|---|---|---|---|---|---|---|---|---|---|---|
| T = 0 | +5° C. | 6 | 6 | 6 | 6 | 6 | 6 | 6 | 6 | 6 | 6 | 6 | 6 |
|  | +5° C. Agitation | 6 | 6 | 6 | 6 | 6 | 6 | 6 | 6 | 6 | 6 | 6 |  |
|  | −75° C. Freeze-thaw | 6 | 6 | 6 | 6 | 6 | 6 | 6 | 6 | 6 | 6 | 6 |  |
| T = 1 M | +5° C. | 6 | 6 | 6 | 6 | 6 | 6 | 6 | 6 | 6 | 6 | 6 | 6 |
|  | +40° C. | 8 | 8 | 8 | 9 | 11 | 11 | 9 | 9 | 10 | 8 | 8 |  |

SC = Study control stored at −70° C.

No differences observed in band number between formulations at T=0 months.
After 1 month stored at +5° C. no change in band number was noted for any of the formulations.
After 1 month stored at +40° C. additional fragment bands were observed in all formulations.
The greatest number of additional bands were observed in formulations F5 (study 1B), F6 (study 1B) and F9 (study 1B) after 1 month stored at +40° C. F5 (study 1B), F6 (study 1B) and F9 (study 1B) are all formulated with arginine.
No changes observed in band number for all formulations and after agitation or freeze/thaw.

TABLE 17

SDS PAGE (reduced) - Percentage Purity - Relative percentage of IgG band area as heavy and light chain bands

| Timepoint | Temperature | F1 | F2 | F3 | F4 | F5 | F6 | F7 | F8 | F9 | F10 | F11 | SC |
|---|---|---|---|---|---|---|---|---|---|---|---|---|---|
| T = 0 | +5° C. | 99.0 | 98.9 | 99.0 | 98.9 | 99.0 | 99.1 | 99.0 | 98.9 | 99.0 | 99.0 | 98.9 | 98.8 |
|  | +5° C. Agitation | 98.9 | 99.1 | 99.0 | 99.1 | 99.1 | 99.1 | 99.0 | 99.1 | 99.1 | 99.0 | 98.9 |  |
|  | −70° C. Freeze-thaw | 99.0 | 98.8 | 98.9 | 98.9 | 99.0 | 99.0 | 99.0 | 99.0 | 99.0 | 98.9 | 99.0 |  |
| T = 1M | +5° C. | 98.8 | 98.5 | 98.9 | 98.9 | 98.6 | 98.8 | 98.7 | 98.7 | 98.8 | 98.7 | 98.3 | 98.0 |
|  | +40° C. | 97.2 | 98.0 | 96.4 | 94.2 | 93.3 | 92.1 | 96.7 | 95.2 | 90.8 | 96.1 | 95.7 |  |

SC = Study control stored at −70° C.

No marked differences observed between formulations at T=0 months.
After 1 month stored at +5° C. no marked change in percentage purity was noted for any of the formulations.
After 1 month stored at +40° C. additional fragment and high molecular weight bands were observed in all formulations with a corresponding slight decrease in percentage IgG purity.
The greatest decrease in purity was observed in formulations F4 (study 1B), F5 (study 1B), F6 (study 1B) and F9 (study 1B) at one month stored at +40° C. F5 (study 1B), F6 (study 1B) and F9 (study 1B) are all formulated with arginine.
Formulation F2 (study 1B) at one month stored at +40° C., demonstrated the smallest change in purity compared to the study start.
No marked changes in reduced SDS PAGE results observed in all formulations after agitation or freeze/thaw.

TABLE 18

DSC - Thermal stability

| Timepoint | Melting Temperature | F1 | F2 | F3 | F4 | F5 | F6 | F7 | F8 | F9 | F10 | F11 | SC |
|---|---|---|---|---|---|---|---|---|---|---|---|---|---|
| T = 0 | $Tm_1$ (° C.) | 70.10 | 69.34 | 69.71 | 69.58 | 67.39 | 67.37 | 69.90 | 69.82 | 66.97 | 71.42 | 68.95 | 68.83 |
|  | $Tm_2$ (° C.) | 76.71 | 76.51 | 76.51 | 76.83 | 74.66 | 74.66 | 76.95 | 77.13 | 74.50 | 77.90 | 75.35 | 72.48 |
|  | $Tm_3$ (° C.) | 83.54 | 83.52 | 83.12 | 83.34 | 81.32 | 81.41 | 83.38 | 83.81 | 80.93 | 83.90 | 81.83 | 83.95 |

$Tm_1$ = Melting temperature of unfolding event 1
$Tm_2$ = Melting temperature of unfolding event 2
$Tm_3$ = Melting temperature of unfolding event 3

Three melting temperatures were observed for all formulations at T=0 months, consistent for an IgG molecule. Formulation F5 (study 1B), F6 (study 1B) and F9 (study 1B) had the lowest temperature unfolding event at T=0 months and all are formulated with arginine.
Formulations F1 (study 1B) and F10 (study 1B) had the highest melting temperatures at T=0 months (70.10° C. and 71.42° C., respectively).

TABLE 19

DLS - high molecular weight species

| Time-point | Data | F1 | F2 | F3 | F4 | F5 | F6 |
|---|---|---|---|---|---|---|---|
| T = 0M | Rh (nm) by intensity | 5.91 | 6.33 | 6.14 | 6.07 | 6.22 | 6.54 |
|  | % RSD by intensity | 27.3 | 26.0 | 28.4 | 27.7 | 29.7 | 31.3 |
| T = 0 Agitation | Rh (nm) by intensity | 5.51 | 6.48 | 6.17 | 5.71 | 6.38 | 7.74 401.63 |
|  | % RSD by intensity | 20.3 | 28.2 | 31.1 | 22.8 | 28.4 | 40.7 48.4 |
| T = 0 F/T | Rh (nm) by intensity | 5.68 310.37 | 6.66 | 6.40 | 6.20 | 6.52 | 6.24 |
|  | % RSD by intensity | 24.1 25.7 | 33.1 | 36.9 | 33.1 | 33.5 | 26.4 |
| T = 1M (+5° C.) | Rh (nm) by intensity | 5.97 | 6.27 | 6.20 | 6.28 | 6.29 | 6.23 |
|  | % RSD by intensity | 27.0 | 22.9 | 35.0 | 34.3 | 32.1 | 28.9 |
| T = 1M (+40° C.) | Rh (nm) by intensity | 7.53 100.52 | 6.48 | 6.25 | 6.23 98.42 | 6.47 | 6.60 |
|  | % RSD by intensity | 56.0 61.6 | 30.8 | 35.1 | 34.8 45.5 | 35.9 | 37.2 |

| Time-point | Data | F7 | F8 | F9 | F10 | F11 | SC |
|---|---|---|---|---|---|---|---|
| T = 0M | Rh (nm) by intensity | 7.58 | 7.04 | 6.80 | 5.99 | 6.42 | 5.97 |
|  | % RSD by intensity | 37.3 | 28.7 | 29.0 | 30.3 | 32.8 | 30.9 |
| T = 0 Agitation | Rh (nm) by intensity | 7.32 | 6.16 668.95 | 6.98 | 6.13 | 5.98 |  |
|  | % RSD by intensity | 34.4 | 30.5 42.4 | 29.9 | 31.6 | 25.7 |  |
| T = 0 F/T | Rh (nm) by intensity | 7.60 | 6.80 359.07 | 6.66 | 6.08 | 6.52 |  |
|  | % RSD by intensity | 36.6 | 27.6 27.1 | 28.1 | 29.1 | 33.3 |  |
| T = 1M (+5° C.) | Rh (nm) by intensity | 7.26 | 7.02 | 6.93 | 5.74 | 5.88 | 6.18 |
|  | % RSD by intensity | 30.3 | 30.1 | 34.4 | 27.2 | 27.9 | 37.8 |
| T = 1M (+40° C.) | Rh (nm) by intensity | 7.66 | 7.75 406.96 | 6.97 | 6.50 118.08 | 6.40 | 390.93 |
|  | % RSD by intensity | 39.1 | 39.7 53.9 | 31.5 | 38.7 46.3 | 35.1 | 47.8 |

Rh = Hydrodynamic radius
RSD = Relative standard deviation

No high molecular weight species were observed in any formulation at T=0 months and T=1 month stored at +5° C.

Higher molecular species were detected in formulations F1 (study 1B), F4 (study 1B), F8 (study 1B), F10 (study 1B) and F11 (study 1B) after one month at +40° C. F1 (study 1B), F4 (study 1B), F10 (study 1B) and F11 (study 1B) are all formulated with glycine.

Higher molecular weight species observed in formulations F1 (study 1B) and F8 (study 1B) after freeze/thaw.

Higher molecular weight species observed in formulations F6 (study 1B) and F8 (study 1B) after agitation.

Study 2B: Excipients of Formulations

Twenty different compositions were evaluated in Study 2B, all at GM37v2 concentrations targeted to be 225 mg/mL. This concentration was selected based on the low viscosity observed for the formulations tested in Study 2A. The actual GM37v2 concentrations ranged from about 216 mg/mL to 233 mg/mL. The pH range covered from 5.1 to 6.4. The measured viscosities were consistently very low, ranging from 10.1 to 16.2 cP.

TABLE 20

Formulations investigated in Study 2B

| Formulation | Buffer type | Buffer conc. | pH | Excipient | GM37v2 (mg/mL) |
|---|---|---|---|---|---|
| 1 | Acetate | 20 | 5.0 | 100 mM Arginine/100 mM Glutamate | 225 |
| 2 | Acetate | 20 | 5.5 | 100 mM Arginine/100 mM Glutamate | 225 |
| 3 | Acetate | 20 | 5.8 | 100 mM Arginine/100 mM Glutamate | 225 |
| 4 | Histidine | 40 | 5.0 | 100 mM Arginine/100 mM Glutamate | 225 |
| 5 | Histidine | 20 | 5.5 | 100 mM Arginine/100 mM Glutamate | 225 |
| 6 | Histidine | 20 | 5.8 | 100 mM Arginine/100 mM Glutamate | 225 |
| 7 | Acetate | 10 | 5.5 | 100 mM Arginine/100 mM Glutamate | 225 |
| 8 | Acetate | 40 | 5.5 | 100 mM Arginine/100 mM Glutamate | 225 |
| 9 | Acetate | 20 | 5.0 | 140 mM NaCl | 225 |
| 10 | Acetate | 20 | 5.5 | 140 mM NaCl | 225 |
| 11 | Acetate | 20 | 5.8 | 140 mM NaCl | 225 |
| 12 | Histidine | 20 | 5.0 | 140 mM NaCl | 225 |
| 13 | Histidine | 40 | 5.5 | 140 mM NaCl | 225 |
| 14 | Histidine | 20 | 5.8 | 140 mM NaCl | 225 |
| 15 | Acetate | 20 | 5.0 | 70 mM NaCl, 50 mM Arginine/50 mM Glutamate | 225 |
| 16 | Acetate | 20 | 5.5 | 70 mM NaCl, 50 mM Arginine/50 mM Glutamate | 225 |
| 17 | Acetate | 20 | 5.8 | 70 mM NaCl, 50 mM Arginine/50 mM Glutamate | 225 |
| 18 | Histidine | 20 | 5.0 | 70 mM NaCl, 50 mM Arginine/50 mM Glutamate | 225 |
| 19 | Histidine | 20 | 5.5 | 70 mM NaCl, 50 mM Arginine/50 mM Glutamate | 225 |
| 20 | Histidine | 40 | 5.8 | 70 mM NaCl, 50 mM Arginine/50 mM Glutamate | 225 |

TABLE 21

Viscosity and osmolality of the tested formulation candidates in Study 2B

| Formulation | Acetate (mM) | Histidine (mM) | Arginine/ Glutamate | NaCl | pH sample | Osmo sample (mOsm/kg*H20) | GM37v2 (mg/mL) | Viscosity (cP) |
|---|---|---|---|---|---|---|---|---|
| F01 | 20 | | 100 | | 5.2 | 348 | 223.9 | 11.49 |
| F02 | 20 | | 100 | | 5.6 | 359 | 225.7 | 33.51 |
| F03 | 20 | | 100 | | 6.1 | 334 | 216.5 | 12.02 |
| F04 | | 40 | 100 | | 5.1 | 403 | 218.2 | 12.11 |
| F05 | | 20 | 100 | | 5.7 | 351 | 235.1 | 13.46 |
| F06 | | 20 | 100 | | 6.3 | 335 | 225.6 | 14.02 |
| F07 | 10 | | 100 | | 5.6 | 402 | 229.7 | 11.68 |
| F08 | 40 | | 100 | | 5.7 | 364 | 234.3 | 13.52 |
| F09 | 20 | | | 140 | 5.4 | 432 | 234.9 | 14.56 |
| F10 | 20 | | | 140 | 5.8 | 404 | 219.5 | 10.79 |
| F11 | 20 | | | 140 | 6.2 | 405 | 229.0 | 12.58 |
| F12 | | 20 | | 140 | 5.5 | 410 | 219.5 | 10.77 |
| F13 | | 40 | | 140 | 5.8 | 472 | 221.7 | 14.50 |
| F14 | | 20 | | 140 | 6.4 | 402 | 224.5 | 11.61 |
| F15 | 20 | | 50 | 70 | 5.3 | 372 | 215.4 | 10.09 |
| F16 | 20 | | 50 | 70 | 5.7 | 383 | 219.9 | 11.61 |
| F17 | 20 | | 50 | 70 | 6.2 | 379 | 217.7 | 15.20 |
| F18 | | 20 | 50 | 70 | 5.3 | 386 | 233.4 | 16.21 |
| F19 | | 20 | 50 | 70 | 5.8 | 335 | 218.8 | 12.11 |
| F20 | | 40 | 50 | 70 | 6.2 | 408 | 222.2 | 13.07 |

Summary of Stability Results of Study 2B

The monomer content (or percent of the main peak, MP) at T0 weeks and various time points and temperatures is tabulated in Table 22. The initial samples display monomer contents at 99.0-99.3%, with a small amount of dimer and fragment present. There was little if any changes over four weeks when stored at 5° C. and small decreases upon storage at 25° C. for the same length of time. At 40° C., the monomer content drops to about 96% after four weeks. These losses were mostly due to an increase in dimer and HMW aggregate, with only small changes in the amount of fragmentation.

TABLE 22

Stability of the tested formulation candidates were measured by Size-exclusion chromatography (SEC)

| Form No | pH sample | Starting GM37v2 (mg/mL) | SEC T0 MP | SEC T2 wk 5 C. MP | SEC T2 wk 25 C. MP | SEC T2 wk 40 C. MP | SEC T4 wk 5 C. MP | SEC T4 wk 25 C. MP | SEC T4 wk 40 C. MP |
|---|---|---|---|---|---|---|---|---|---|
| F01 | 5.2 | 223.9 | 99.3 | 99.2 | 99.1 | 97.0 | 99.2 | 99.0 | 95.9 |
| F02 | 5.6 | 225.7 | 99.2 | 99.2 | 99.1 | 97.1 | 99.2 | 99.0 | 96.2 |
| F03 | 6.1 | 216.5 | 99.2 | 99.2 | 99.0 | 97.0 | 99.1 | 98.9 | 96.2 |
| F04 | 5.1 | 218.2 | 99.3 | 99.3 | 99.2 | 96.9 | 99.3 | 99.1 | 95.7 |
| F05 | 5.7 | 235.1 | 99.3 | 99.2 | 99.1 | 97.2 | 99.2 | 99.0 | 96.2 |
| F06 | 6.3 | 225.6 | 99.2 | 99.1 | 99.0 | 97.0 | 99.1 | 98.9 | 96.1 |
| F07 | 5.6 | 229.7 | 99.2 | 99.2 | 99.1 | 97.1 | 99.2 | 99.0 | 96.2 |
| F08 | 5.7 | 234.3 | 99.2 | 99.2 | 99.0 | 97.1 | 99.1 | 98.9 | 96.2 |
| F09 | 5.4 | 234.9 | 99.1 | 99.0 | 98.8 | 96.5 | 99.0 | 98.7 | 95.2 |
| F10 | 5.8 | 219.5 | 99.0 | 99.0 | 98.7 | 96.5 | 98.9 | 98.6 | 95.5 |
| F11 | 6.2 | 229.0 | 99.0 | 98.9 | 98.6 | 96.5 | 98.8 | 98.5 | 95.4 |
| F12 | 5.5 | 219.5 | 99.2 | 99.2 | 99.0 | 96.9 | 99.2 | 98.9 | 95.8 |
| F13 | 5.8 | 221.7 | 99.2 | 99.2 | 99.0 | 96.9 | 99.2 | 98.9 | 95.8 |
| F14 | 6.4 | 224.5 | 99.1 | 99.0 | 98.8 | 96.7 | 99.0 | 98.6 | 95.6 |
| F15 | 5.3 | 215.4 | 99.2 | 99.1 | 99.1 | 96.8 | 99.2 | 99.0 | 95.6 |
| F16 | 5.7 | 219.9 | 99.2 | 99.1 | 99.0 | 96.9 | 99.1 | 98.9 | 95.9 |
| F17 | 6.2 | 217.7 | 99.1 | 99.1 | 98.9 | 96.9 | 99.0 | 98.8 | 95.9 |
| F18 | 5.3 | 233.4 | 99.3 | 99.2 | 99.1 | 97.0 | 99.2 | 99.0 | 95.8 |
| F19 | 5.8 | 218.8 | 99.2 | 99.2 | 99.1 | 97.1 | 99.2 | 99.0 | 96.1 |
| F20 | 6.2 | 222.2 | 99.2 | 99.1 | 99.0 | 97.0 | 99.1 | 98.9 | 96.0 |

The relative area of the main peak (MP) at T0 weeks and various time points and temperatures is tabulated in Table 23. The main peak was initially about 74% or the relative area of the chromatogram. There is little, if any, change during storage at 5° C. However, at 25° C., there is an appreciable decrease to ~71% after four weeks and 50-60% when stored at 40° C. for that length of time. So, even at these very high GM37v2 concentrations, the formulations appear to be chemically and physically stable when stored at 5° C. and even at elevated temperatures, the losses are quite modest.

TABLE 23

Stability of the tested formulation candidates were measured by Cation exchange chromatography (CEX) "m" means that no data is available for this data point

| Form No. | pH sample | Starting GM37v2 (mg/mL) | CEX T0 MP | CEX T2 wk 5 C. MP | CEX T2 wk 25 C. MP | CEX T2 wk 40 C. MP | CEX T4 wk 5 C. MP | CEX T4 wk 25 C. MP | CEX T4 wk 40 C. MP |
|---|---|---|---|---|---|---|---|---|---|
| F01 | 5.2 | 223.9 | 73.9 | 73.5 | 71.6 | 60.5 | 73.6 | 70.6 | 51.8 |
| F02 | 5.6 | 225.7 | 73.9 | 74.0 | 72.4 | 62.9 | 73.9 | 71.6 | 55.3 |
| F03 | 6.1 | 216.5 | 74.1 | 73.8 | 73.0 | 65.2 | 74.1 | 72.4 | 58.9 |
| F04 | 5.1 | 218.2 | 73.8 | 73.4 | 71.4 | 60.2 | 73.4 | 70.3 | 51.9 |
| F05 | 5.7 | 235.1 | 74.0 | 73.8 | 72.4 | 63.3 | 73.9 | 71.8 | m |
| F06 | 6.3 | 225.6 | 74.2 | 74.1 | 72.8 | 65.5 | 74.0 | m | 59.2 |
| F07 | 5.6 | 229.7 | 73.9 | 73.6 | 72.4 | 62.7 | 73.7 | 71.5 | 55.5 |
| F08 | 5.7 | 234.3 | 74.1 | 73.7 | 72.6 | 63.6 | 73.8 | 72.1 | 56.2 |
| F09 | 5.4 | 234.9 | 73.9 | 73.5 | 72.0 | 62.3 | 73.6 | 71.2 | 54.5 |
| F10 | 5.8 | 219.5 | 73.9 | 73.9 | 72.6 | 64.5 | 73.9 | 71.9 | 58.1 |
| F11 | 6.2 | 229.0 | 74.0 | 73.8 | 72.7 | 66.4 | 74.0 | 72.7 | 60.9 |
| F12 | 5.5 | 219.5 | 73.8 | 73.6 | 72.2 | 64.1 | 73.6 | 71.6 | 57.7 |
| F13 | 5.8 | 221.7 | 73.9 | 73.8 | 72.4 | 64.8 | 73.8 | 72.4 | 59.0 |
| F14 | 6.4 | 224.5 | 74.1 | 73.9 | 72.6 | 66.9 | 74.0 | 72.4 | 61.8 |
| F15 | 5.3 | 215.4 | 73.7 | 73.5 | 72.0 | 61.6 | m | 71.8 | 53.4 |
| F16 | 5.7 | 219.9 | 73.9 | 73.8 | 72.6 | 64.1 | 74.1 | 71.7 | 59.2 |
| F17 | 6.2 | 217.7 | 74.0 | 73.8 | 72.9 | 66.0 | 73.9 | m | 59.9 |
| F18 | 5.3 | 233.4 | 73.9 | 73.5 | 71.9 | 62.6 | 73.6 | 71.0 | 55.0 |
| F19 | 5.8 | 218.8 | 73.9 | 73.7 | 72.7 | 64.9 | m | 72.0 | 60.3 |
| F20 | 6.2 | 222.2 | 74.2 | 73.8 | 72.7 | 66.0 | 74.1 | 72.0 | 59.5 |

Conclusion/Summary of Excipient Study

Study 11B:

Based on the of all analytical methods described in Study 1B the most suitable formulation candidates are formulations F2 (study 1B) and F3 (study 1B).

The data was assessed for each formulation; however, trends were also assessed across formulations by identifying consistent effects for specific excipients.

Formulation F3 (study 1B) presented more sub-visible particles at both the study start and T=1 month when stored at +5° C., compared to formulation F2 (study 1B).

On comparison of all the formulations the presence of PS80 reduced the overall number of sub-visible particles and to a lesser extent the number of visible particles. Formulation F4 (study 1B) which differ from composition as F3 (study 1B) by the presence of 0.02% PS80 is not preferred as formulation candidate as although it had less sub-visible particles than F3 (study 1B), it also demonstrated lower purity by SDS PAGE and GP HPLC and presence of aggregates by DLS and particulates determined at A340.

The most promising formulation candidate is therefore formulation F2 (study 1B) (25 mM Histidine, 100 mM Sodium Chloride, pH 6.0 and 100 mM sucrose). The rationale for selecting this candidate to be best suited for further development was that overall the data for F2 (study 1B) was most favorable since it generally demonstrated the least amount of change across all assays.

Study 2B:

The SEC data indicate that the stability is best at pH 4.5 and 6.5, depending on the storage temperature. Histidine buffer can be stabilizing especially at concentrations >20 mM. NaCl has only a minor effect on stability. Higher GM37v2 concentration leads to more rapid loss of monomer, presumably by aggregation, but losses are small over the time course studied. The CEX data indicate that maintaining the relative amount of the pain peak is best at pH 5.5 to 7.0. Again, Histidine is favorable for maintaining stability. NaCl can also be beneficial up to around 100 mM.

Given these collective findings, the optimal pH is likely to be near 6.0, using a Histidine buffer concentration of 20-40 mM. The nature of the tonicity modifier does not appear to be critical for obtaining a suitable clinical formulation, but NaCl seems to be the best of those tested in Study 2B.

Example C—Surfactants of Formulations

Finally, the inventors of the present invention investigated the effect of adding polysorbate 80 to the most promising formulation candidates obtained from Example A and Example B.

Study 1C: Non-Ionic Surfactants (Polysorbate 80)

The stability of GM37v2 was assessed in two identical formulations, except that one formulation comprised polysorbate 80 (F2 (study 1C)) and one did no (F1 (study 1C)), otherwise the excipients were identical. The formulations were tested at the target storage temperature 5±3° C. and at elevated temperature 40±2° C. at not more than 25% RH, as well as following agitation. The GM37v2 concentration in each formulation was of 50.0 mg/mL+/−5.0.

TABLE 24

Formulations investigated in study 1C

| Polysorbate 80 Formulation ID | Formulation composition |
|---|---|
| F1 | 25 mM L-histidine, 100 mM NaCl, 100 mM sucrose, pH 6.0 |
| F2 | 25 mM L-histidine, 100 mM NaCl, 100 mM sucrose, pH 6.0 + 0.02% Polysorbate 80 |

Both formulations were subject to an agitation protocol, which was initiated at T=0 months. Samples were agitated using a rotating agitator set to 30 rpm for 48 hours at +5° C. Post agitation the samples were stored at +5° C. until testing.

The stability of each of the two formulations were then measured at baseline (Time zero, 0 months; T=0), after three months (T=3, 3 months) and after 6 months (T=6, 6 months) as described in table 25.

TABLE 25

Analytical methods used in Study 1C

| | Time point (month) at 5° C. and 40° C. | | | |
|---|---|---|---|---|
| Analytical method | 0 | 3 | 6 | Agitation* |
| Visual appearance (particles) | x | x | x | x |
| Non-reduced CE-SDS | X | X | X | X |
| Reduced CE-SDS | x | x | x | x |
| GP-HPLC | X | x | x | X |
| Sub. visible particle** | x | x | x | x |

*Agitation study performed over 48 hours at 5° C. on a rotatry shaker at time zero only.
**the analysis was only performed at 5° C.

Summarized Results of Study 1C:

TABLE 26

Storage at +5° C. without tween

| | | Timepoint (Months)/Testing Window (Dates of Initiation to Last Assay) | | |
|---|---|---|---|---|
| Assay | Specification | 0<br>16 Jan. 2017 to<br>23 Jan. 2017 | 3<br>17 Apr. 2017 to<br>20 Apr. 2017 | 6<br>17 Jul. 2017 to<br>26 Jul. 2017 |
| Visible particles | Report result | FVP | FVP | FVP |
| Reduced CE SDS | ≥95.0% IgG as heavy and light chains | 98.8 | 98.7 | 98.8 |
| Non-reduced CE SDS | Report result as % intact IgG and comparison to reference standard | 97.9<br>CR | 97.2<br>CR | 97.4<br>CR |
| GP HPLC | ≥95.0% IgG monomer | 99.5 | 99.4 | 99.4 |
| | ≤5.0% aggregates | 0.5 | 0.6 | 0.6 |
| | Report % fragments | <LOQ | <LOQ | <LOQ |

TABLE 26-continued

| | | Storage at +5° C. without tween | | |
|---|---|---|---|---|
| | | Timepoint (Months)/Testing Window (Dates of Initiation to Last Assay) | | |
| | | 0 | 3 | 6 |
| | | 16 Jan. 2017 to | 17 Apr. 2017 to | 17 Jul. 2017 to |
| Assay | Specification | 23 Jan. 2017 | 20 Apr. 2017 | 26 Jul. 2017 |
| Sub-visible particle counting | Pass according to USP<788> | | | |
| | ≥25 μm: ≤600 particles per vial | 285 | 53 | 767 |
| | ≥10 μm: ≤6000 particles per vial | 20892 | 4884 | 13736 |
| | ≥5 μm: Report particles per vial | 84719 | 30690 | 73010 |
| | ≥2 μm: Report particles per vial | 266894 | 117471 | 233688 |

FVP = Free from visible particles
CR = Comparable to reference
<LOQ = less than limit of quantitation for the method (<0.1%)

TABLE 27

| | | Storage at +5° C. with tween | | |
|---|---|---|---|---|
| | | Timepoint (Months)/Testing Window (Dates of Initiation to Last Assay) | | |
| | | 0 | 3 | 6 |
| | | 16 Jan. 2017 to | 17 Apr. 2017 to | 17 Jul. 2017 to |
| Assay | Specification | 23 Jan. 2017 | 20 Apr. 2017 | 26 Jul. 2017 |
| Visible particles | Report result | FFP | FFP | FVP |
| Reduced CE SDS | ≥95.0% IgG as heavy and light chains | 98.9 | 98.7 | 98.8 |
| Non-reduced CE SDS | Report result as % intact IgG and comparison to reference standard | 97.9 CR | 97.2 CR | 97.3 CR |
| GP HPLC | ≥95.0% IgG monomer | 99.5 | 99.4 | 99.3 |
| | ≤5.0% aggregates | 0.5 | 0.6 | 0.6 |
| | Report % fragments | <LOQ | <LOQ | <LOQ |
| Sub-visible particle counting | Pass according to USP<788> | | | |
| | ≥25 μm: ≤600 particles per vial | 19 | 12 | 16 |
| | ≥10 μm: ≤6000 particles per vial | 401 | 273 | 233 |
| | ≥5 μm: Report particles per vial | 1909 | 1523 | 1306 |
| | ≥2 μm: Report particles per vial | 12534 | 10388 | 8764 |

FFP = Few fibrous particles
FVP = Free from visible particles
CR = Comparable to reference
<LOQ = less than limit of quantitation for the method (<0.1%)

TABLE 28

| | Storage at +5° C. agitation without tween |
|---|---|
| | Timepoint (Months)/Testing Window (Dates of Initiation to Last Assay) Agitation at T = 0 |
| Assay | Specification | 16 Jan. 2017 to 23 Jan. 2017 |
|---|---|---|
| Visible particles | Report result | NR |
| Reduced CE SDS | ≥95.0% IgG as heavy and light chains | 98.8 |
| Non-reduced CE SDS | Report result as % intact IgG and comparison to reference standard | 97.8 CR |
| GP HPLC | ≥95.0% IgG monomer | 99.4 |
| | ≤5.0% aggregates | 0.6 |
| | Report % fragments | <LOQ |
| Sub-visible particle counting | Pass according to USP<788> | |
| | ≥25 μm: ≤600 particles per vial | 13 |
| | ≥10 μm: ≤6000 particles per vial | 1000 |
| | ≥5 μm: Report particles per vial | 28190 |
| | ≥2 μm: Report particles per vial | 123465 |

NR = No result (was not possible to assess visible particles due to sample being opaque)
CR = Comparable to reference
<LOQ = less than limit of quantitation for the method (<0.1%)

TABLE 29

Storage at +5° C. agitation with tween

| Assay | Specification | Timepoint (Months)/Testing Window (Dates of Initiation to Last Assay) Agitation at T = 0 16 Jan. 2017 to 23 Jan. 2017 |
|---|---|---|
| Visible particles | Report result | FVP |
| Reduced CE SDS | ≥95.0% IgG as heavy and light chains | 98.9 |
| Non-reduced CE SDS | Report result as % intact IgG and comparison to reference standard | 97.9 CR |
| GP HPLC | ≥95.0% IgG monomer | 99.5 |
| | ≤5.0% aggregates | 0.5 |
| | Report % fragments | <LOQ |
| Sub-visible particle counting | Pass according to USP<788> | |
| | ≥25 μm: ≤600 particles per vial | 3 |
| | ≥10 μm: ≤6000 particles per vial | 253 |
| | ≥5 μm: Report particles per vial | 978 |
| | ≥2 μm: Report particles per vial | 3893 |

FVP = Free from visible particles
CR = Comparable to reference
<LOQ = less than limit of quantitation for the method (<0.1%)

TABLE 30

Storage at +40° C. without tween

| Assay | Specification | 0 16 Jan. 2017 to 23 Jan. 2017 | 3 17 Apr. 2017 to 20 Apr. 2017 | 6 17 Jul. 2017 to 26 Jul. 2017 |
|---|---|---|---|---|
| Visible particles | Report result | FVP | FFP | FFP |
| Reduced CE SDS | ≥95.0% IgG as heavy and light chains | 98.8 | 94.2 | 90.4 |
| Non-reduced CE SDS | Report result as % intact IgG and comparison to reference standard | 97.9 CR | 90.3 CR | 84.0 NCR |
| GP HPLC | ≥95.0% IgG monomer | 99.5 | 96.5 | 92.1 |
| | ≤5.0% aggregates | 0.5 | 1.4 | 3.2 |
| | Report % fragments | <LOQ | 2.1 | 4.7 |
| Sub-visible particle counting | Pass according to USP<788> | | | |
| | ≥25 μm: ≤600 particles per vial | 285 | NT | NT |
| | ≥10 μm: ≤6000 particles per vial | 20892 | | |
| | ≥5 μm: Report particles per vial | 84719 | | |
| | ≥2 μm: Report particles per vial | 266894 | | |

FVP = Free from visible particles
FFP = Few fibrous particles
CR = Comparable to reference
NCR = Not comparable to reference
NT = Not tested
<LOQ = Less than limit of quantitation for the method (<0.1%)

TABLE 31

Storage at +40° C. with tween

| Assay | Specification | 0 16 Jan. 2017 to 23 Jan. 2017 | 3 17 Apr. 2017 to 20 Apr. 2017 | 6 17 Jul. 2017 to 26 Jul. 2017 |
|---|---|---|---|---|
| Visible particles | Report result | FFP | FVP | FFP |
| Reduced CE SDS | ≥95.0% IgG as heavy and light chains | 98.9 | 94.1 | 90.3 |
| Non-reduced CE SDS | Report result as % intact IgG and comparison to reference standard | 97.9 CR | 90.5 CR | 84.0 CR |
| GP HPLC | ≥95.0% IgG monomer | 99.5 | 96.4 | 91.9 |
| | ≤5.0% aggregates | 0.5 | 1.5 | 3.4 |
| | Report % fragments | <LOQ | 2.1 | 4.7 |

TABLE 31-continued

Storage at +40° C. with tween

| | | Timepoint (Months)/Testing Window (Dates of Initiation to Last Assay) | | |
|---|---|---|---|---|
| | | 0 | 3 | 6 |
| | | 16 Jan. 2017 to | 17 Apr. 2017 to | 17 Jul. 2017 to |
| Assay | Specification | 23 Jan. 2017 | 20 Apr. 2017 | 26 Jul. 2017 |
| Sub-visible particle counting | Pass according to USP<788> | | | |
| | ≥25 μm: ≤600 particles per vial | 19 | NT | NT |
| | ≥10 μm: ≤6000 particles per vial | 401 | | |
| | ≥5 μm: Report particles per vial | 1909 | | |
| | ≥2 μm: Report particles per vial | 12534 | | |

FFP = Few fibrous particles
FVP = Free from visible particles
CR = Comparable to reference
NT = Not Tested
<LOQ = less than limit of quantitation for the method (<0.1%)

The formulation without Polysorbate 80 presented more sub-visible particles of all sizes at both the study start and T=6 months when stored at +5° C. compared to the formulation with Polysorbate 80, but both formulations demonstrated no marked change at T=6 compared to their respective T=0 months results.

The formulations, with and without Polysorbate 80, stored at +5° C. were both free from visible particles at T=6 months and demonstrated no marked change by GP HPLC, reduced and non-reduced CE SDS at T=6 months compared to the T=0 months measurements.

At six months, the formulations (with and without Polysorbate 80) at the +40° C. condition were determined to have no marked difference between them. However, at six months both these formulations demonstrated a comparable trend of decreasing percentage IgG monomer with concomitant increases in percentage aggregates and fragments by GP HPLC and decreasing purity by reduced and non-reduced CE SDS compared to the study start.

For the formulations subject to the agitation protocol, it was found that the formulation without Polysorbate 80 presented more sub-visible particles of all sizes compared to the formulation with polysorbate 80.

Study 2C: Non-Ionic Surfactants (Polysorbate 80/Poloxamer 188)

The inventors set out to investigate the effect of adding a surfactant to the most promising formulations candidates obtained from studies 2A and 2B.

Ten formulations were tested, and their composition is described in table 32.

TABLE 32

Formulations investigated in study 2C

| Formulations | Base composition | Surfactant |
|---|---|---|
| *F01 | 20 mM Histidine, 140 mM NaCl, pH 6.0, 225 mg/mL GM37v2 | None |
| F02 | 20 mM Histidine, 140 mM NaCl, pH 6.0, 225 mg/mL GM37v2 | 0.02% (w/v) PS80 |
| F03 | 20 mM Histidine, 140 mM NaCl, pH 6.0, 225 mg/mL GM37v2 | 0.05% (w/v) PS80 |
| F04 | 20 mM Histidine, 140 mM NaCl, pH 6.0, 225 mg/mL GM37v2 | 0.02% (w/v) Poloxamer 188 |
| *F05 | 20 mM Histidine, 140 mM NaCl, pH 6.0, 225 mg/mL, GM37v2 | 0.05% (w/v) Polaxamer 188 |
| *F06 | 20 mM Acetate, 70 mM NaCl, 50 mM Arginine/Glutamate, pH 6.0, 225 mg/mL GM37v2 | None |
| F07 | 20 mM Acetate, 70 mM NaCl, 50 mM Arginine/Glutamate, pH 6.0, 225 mg/mL GM37v2 | 0.02% (w/v) PS80 |
| F08 | 20 mM Acetate, 70 mM NaCl, 50 mM Arginine/Glutamate, pH 6.0, 225 mg/mL GM37v2 | 0.05% (w/v) PS80 |
| F09 | 20 mM Acetate, 70 mM NaCl, 50 mM Arginine/Glutamate, pH 6.0, 225 mg/mL GM37v2 | 0.02% (w/v) Poloxamer 188 |
| *F10 | 20 mM Acetate, 70 mM NaCl, 50 mM Arginine/Glutamate, pH 6.0. 225 mg/mL GM37v2 | 0.05% (w/v) Polaxamer 188 |
| *CTL | 25 mM Histidine, 100 mM NaCl, 100 mM Sucrose, 50 mg/mL, pH 6.0 | 0.02% (w/v) PS80 |

*Subvisible particle count was measured on these formulations only

These formulations were separately exposed to multiple freeze-thaw cycles and agitation stress. These formulations were tested by A280, SE-HPLC, and sub-visible particle analysis (select samples).

Agitation Stress Measurements in Study 2C

Formulations were filled into Schott, Fiolax, clear blowback, type I glass stoppered with Flurotec serum stoppers (Target of 1 mL in a 2 mL vial) and sealed with crimp caps. These vials were oriented in a horizontal position and agitated at room temperature using an orbital shaker (3 mm orbit) at a speed of 590 rpm (revolutions/minute). Samples were taken at 5-hours and 24-hours and tested. Non-agitated control samples were kept in a sample box at room temperature.

5 Times (5×) Freeze-Thaw Stress Measurements in Study 2C

Formulations were filled (0.65 mL) into polypropylene tubes and exposed to 5× freeze-thaw cycles. Samples were frozen at −80° C. for at least 12-hours. During the thaw, the tubes were placed at room temperature and allowed to thaw for no longer than 3-hours. All of the thawed formulations were inverted several times to mix, prior to re-freezing. After the 5× freeze-thaw cycles, the samples were analyzed.

bate 80 to the formulation candidate would likely be beneficial for maintaining interfacial stability, with a target concentration likely to be near 0.02% (w/v).

Example D—Long Term Storage Stability

Two formulations were evaluated for their performance in regard to long-term storage stability. This study collected stability data over the course of six months at 5° and 25° C.

TABLE 33

Formulations investigated in Example D

| Verification Formulations | Composition |
|---|---|
| Lead | 25 mM Histidine, 100 mM Sucrose, 100 mM Sodium Chloride, 0.02% Polysorbate 80, pH 6.0, 200 mg/mL GM37v2 |
| Backup | 40 mM Histidine, 100 mM Sodium chloride, 0.02% Polysorbate 80, pH 6.0, 200 mg/mL GM37v2 |

Summarized Results of Study 2C:

The agitation stress experiment showed that there was no significant variation in the measured GM37v2 concentration between any formulation candidates at either of the tested time points. The physical stability of the agitation samples was evaluated by SE-HPLC. The results demonstrated that although the observed changes were small, it appears that the formulations containing Poloxamer 188 may be destabilizing upon agitation.

The sub-visible particle counts were evaluated for select agitation samples. The particle counts and size range were all lower than the required specification of USP 788.

Similar measurements were performed for the freeze/thaw samples. These results showed that no significant change in GM37v2 concentration was observed after multiple freeze-thaw cycles.

Upon evaluation of the SE-HPLC data, although the changes are small, it does appear that F04 (study 2C) and F05 (study 2C) (Histidine buffer formulations containing Poloxamer 188) demonstrates the greatest increase after multiple freeze-thaw cycles.

Also for the freeze/thaw samples the particle counts and size range were all lower than the required specification of USP 788.

Conclusion/Summary of Surfactant Study

Study 1C:

Overall, based on the results of all analytical methods utilized in this study (visible particles, reduced and non-reduced CE SDS, GP-HPLC and sub-visible particles) the inventors concluded that the inclusion of 0.02% (w/v) Polysorbate 80 in the formulation reduced the overall number of sub-visible particles and hence adding polysorbate 80 to the candidate formulation produced an optimal clinically suitable formulation.

Study 2C:

The tested formulation candidates indicate that in these formulations GM37v2 does not appear to exhibit significant changes in physical stability upon exposure to agitation or freeze-thaw stress. However, it does appear that, in general, a surfactant is beneficial for the performance of the formulations in terms of the physical stability. Further, Polysorbate 80 (polysorbate 80) appears to be slightly preferred over Poloxamer 188, which appears to be slightly destabilizing compared to polysorbate 80. Accordingly, adding polysor- Summarized Results of Example D:

Both the lead and backup formulations displayed good stability upon storage at 5° C. up to six months and 25° C. up to three months. However, in terms of sub-visible particles formation and chemical stability by CEX-HPLC, the lead formulation (25 mM Histidine, 100 mM sucrose, 100 mM sodium chloride, 0.02% polysorbate 80, pH 6.0, 200 mg/mL GM37v2) performed better than the backup formulation (40 mM Histidine, 100 mM sodium chloride, 0.02% polysorbate 80, pH 6.0, 200 mg/mL GM37v2) as predominantly differentiated by the observed trends under accelerated conditions of 25° C. Both were comparable in terms of stability measured by SE-HPLC, where both exhibited losses that extrapolate to <2% over the course of two years. Neither formulation showed any appreciable loss of protein over the course of the study and the pH remained constant for all of the stored samples.

A specific liquid pharmaceutical composition of the invention containing 25 mM histidine/histidine hydrochloride, 100 mM sucrose, 100 mM sodium chloride, 0.02% Polysorbate 80, pH 6.0 with a concentration of 53.0±5 mg/mL GM37v2 and a nominal volume of 20 mL was also tested for stability. These tests showed that this composition is suitable for long term storage at suitable conditions such as 5° C.±3° C. and maintains the physical and chemical integrity of the antibody GM37v2 for at least 36 months.

Further the specific liquid pharmaceutical composition of the invention containing 25 mM histidine/histidine hydrochloride, 100 mM sucrose, 100 mM sodium chloride, 0.02% Polysorbate 80, pH 6.0 with a concentration of 53.0±5 mg/mL GM37v2 was investigated by accelerated stress condition at 25° C. which showed that this formulation was stable for at least 6 months under such conditions.

Consolidated Conclusions from Examples A-C and D:

From study 1A, 1B and 1C it was found that a formulation comprising GM37v2, 25 mM L-histidine, 100 mM NaCl, 100 mM sucrose and 0.02% Polysorbate 80 at pH 6.0 is the most suitable formulation to progress into clinical development.

Study 2A, 2B and 2C revealed that the optimal pH is likely to be near 6.0, using a Histidine buffer concentration of 20-40 mM. The nature of the tonicity modifier does not appear to be critical, but NaCl is preferred, due to the observed viscosity reducing effect. Polysorbate 80 is beneficial for maintaining interfacial stability, with a target concentration near 0.02% (w/v). Therefore, formulations comprising 30-225 mg/mL GM37v2, 20-40 mM Histidine, 100 mM NaCl, 100 mM sucrose and 0.02% Polysorbate 80 at pH 6.0 are the optimal formulation candidate.

Example D revealed by using accelerated stress condition at 25° C. for three to six months that the formulations comprising 25 mM Histidine, 100 mM sucrose, 100 mM sodium chloride, 0.02% polysorbate 80, at pH 6.0, and 53 or 200 mg/mL GM37v2, are stable upon longer-term storage. This also applies for a relatively high GM37v2 concentration of 200 mg/mL and even at this elevated concentration, the above formulation exhibits a low viscosity of <10 cP.

Accordingly, the inventors identified formulation candidates which are suited for clinical use, this especially applies to the ones comprising histidine buffer at about pH 6.0 and even more specifically to the compositions further comprising NaCl, sucrose and Polysorbate 80 as they exhibit desired properties in the field of pharmaceutical compositions, such as high stability and low viscosity, over a large range of GM37v2 concentrations (30-225 mg/mL). Accordingly, the inventors have identified formulation candidates that are very flexible and useful in clinical settings to administer various dosing regimens of GM37v2 to patients.

The invention claimed is:

1. A method of treating multiple system atrophy (MSA) in a human patient, the method comprising intravenously administering to the patient a full length monoclonal antibody which binds to alpha synuclein at a dose of 200 mg once every 4 weeks, wherein the antibody comprises heavy chain CDR1, CDR2, and CDR3 comprising the amino acid sequences of SEQ ID NOs: 1, 34, and 3, respectively, and light chain CDR1, CDR2, and CDR3 comprising the amino acid sequences of SEQ ID NOs: 4, 5, and 6, respectively.

2. The method of claim 1, wherein the antibody comprises a heavy chain variable domain and a light chain variable domain comprising the amino acid sequences of SEQ ID NOs: 31 and 8, respectively.

3. The method of claim 1, wherein the antibody comprises a constant heavy chain domain comprising the amino acid sequence of SEQ ID NO: 18 and a kappa light chain constant domain comprising the amino acid sequence of SEQ ID NO: 17.

4. The method of claim 1, wherein the antibody has a $K_D$ value of binding to the monomeric form of alpha synuclein of about 30-40 nM and a $K_D$ value of binding to the oligomeric form of alpha synuclein of about 0.1-1.0 nM, such that the ratio between monomeric and oligomeric binding is approximately 60-70-fold enhancement.

5. The method of claim 1, wherein the antibody has a half-life in the human patient of about 28-30 days.

6. The method of claim 1, wherein the antibody is a human IgG1 antibody.

7. The method of claim 1, wherein the antibody is administered in an amount and a frequency sufficient to achieve a CSF mean steady state concentration of the antibody of at least 3 nM.

8. The method of claim 1, wherein the antibody is administered in an amount and a frequency sufficient to achieve a target engagement to oligomeric forms of alpha synuclein in CSF of at least 85%.

9. The method of claim 1, wherein the antibody has a KD value of binding to the monomeric form of alpha synuclein of about 36 nM and a KD value of binding to the oligomeric form of alpha synuclein of about 0.5 nM such that the ratio between the monomeric and oligomeric binding is approximately 65-fold enhancement.

10. The method of claim 1, wherein the MSA is possible MSA, probable MSA, MSA type C, MSA type P, clinically established MSA, or clinically probable MSA.

11. The method of claim 1, wherein the treatment of MSA delays disease progression.

12. The method of claim 1, wherein the antibody is formulated in a liquid pharmaceutical composition.

13. The method of claim 1, wherein the antibody is administered in an amount and a frequency sufficient to achieve a CSF mean steady state concentration of the antibody of at least 6 nM.

14. The method of claim 1, wherein the antibody is administered in an amount and a frequency sufficient to achieve a CSF mean steady state concentration of the antibody of at least 12 nM.

15. The method of claim 1, wherein the antibody is administered in an amount and a frequency sufficient to achieve a target engagement to oligomeric forms of alpha synuclein in CSF of at least 90%.

16. The method of claim 1, wherein the antibody is administered in an amount and a frequency sufficient to achieve a target engagement to oligomeric forms of alpha synuclein in CSF of at least 95%.

* * * * *

UNITED STATES PATENT AND TRADEMARK OFFICE
CERTIFICATE OF CORRECTION

| | |
|---|---|
| PATENT NO. | : 12,077,578 B2 |
| APPLICATION NO. | : 18/341437 |
| DATED | : September 3, 2024 |
| INVENTOR(S) | : Josefine Nielsen Søderberg et al. |

It is certified that error appears in the above-identified patent and that said Letters Patent is hereby corrected as shown below:

In the Claims

At Column 131, Claim number 1, Line number 62, delete "body which binds to alpha synuclein at a dose of 200 mg" and insert --body which binds to alpha synuclein at a dose of 4200 mg--

Signed and Sealed this
Twenty-ninth Day of October, 2024

Katherine Kelly Vidal
*Director of the United States Patent and Trademark Office*

```
                       SEQUENCE LISTING

Sequence total quantity: 43
SEQ ID NO: 1           moltype = AA  length = 10
FEATURE                Location/Qualifiers
REGION                 1..10
                       note = GM37 CDR 1 Heavy Chain
source                 1..10
                       mol_type = protein
                       organism = synthetic construct
SEQUENCE: 1
GFTFSSYAMT                                                                10

SEQ ID NO: 2           moltype = AA  length = 17
FEATURE                Location/Qualifiers
REGION                 1..17
                       note = GM37 CDR2 Heavy Chain
source                 1..17
                       mol_type = protein
                       organism = synthetic construct
SEQUENCE: 2
AIRSNGDRTD YADSVKG                                                        17

SEQ ID NO: 3           moltype = AA  length = 9
FEATURE                Location/Qualifiers
REGION                 1..9
                       note = GM37 CDR3 Heavy Chain
source                 1..9
                       mol_type = protein
                       organism = synthetic construct
SEQUENCE: 3
AKNWAPFDS                                                                  9

SEQ ID NO: 4           moltype = AA  length = 11
FEATURE                Location/Qualifiers
REGION                 1..11
                       note = GM37 CDR1 Light Chain
source                 1..11
                       mol_type = protein
                       organism = synthetic construct
SEQUENCE: 4
ASQSVSSSYL A                                                              11

SEQ ID NO: 5           moltype = AA  length = 7
FEATURE                Location/Qualifiers
REGION                 1..7
                       note = GM37 CDR 2 Light Chain
source                 1..7
                       mol_type = protein
                       organism = synthetic construct
SEQUENCE: 5
GASSRAT                                                                    7

SEQ ID NO: 6           moltype = AA  length = 9
FEATURE                Location/Qualifiers
REGION                 1..9
                       note = GM37 CDR 3 Light Chain
source                 1..9
                       mol_type = protein
                       organism = synthetic construct
SEQUENCE: 6
QQYGSSPWT                                                                  9
```

```
SEQ ID NO: 7             moltype = AA   length = 116
FEATURE                  Location/Qualifiers
REGION                   1..116
                         note = GM37 CDR Heavy Chain
source                   1..116
                         mol_type = protein
                         organism = synthetic construct
SEQUENCE: 7
EVQLLESGGG LVQTGGSLRL SCAASGFTFS SYAMTWVRQA PGKGLEWVSA IRSNGDRTDY   60
ADSVKGRFTI SRDNSQNTLY LQMNSLRAED TAVYYCAKNW APFDSWGQGT LVTVSS      116

SEQ ID NO: 8             moltype = AA   length = 108
FEATURE                  Location/Qualifiers
REGION                   1..108
                         note = GM 37 Light Chain
source                   1..108
                         mol_type = protein
                         organism = synthetic construct
SEQUENCE: 8
EIVLTQSPGT LSLSPGERAT LSCRASQSVS SSYLAWYQQK PGQAPRLLIY GASSRATGIP   60
DRFSGSGSGT DFTLTISRLE PEDFAVYYCQ QYGSSPWTFG QGTKVEIK               108

SEQ ID NO: 9             moltype = AA   length = 6
FEATURE                  Location/Qualifiers
REGION                   1..6
                         note = Epitope 112-117
source                   1..6
                         mol_type = protein
                         organism = synthetic construct
SEQUENCE: 9
ILEDMP                                                              6

SEQ ID NO: 10            moltype = AA   length = 140
FEATURE                  Location/Qualifiers
REGION                   1..140
                         note = Alpha-synuclein
source                   1..140
                         mol_type = protein
                         organism = synthetic construct
SEQUENCE: 10
MDVFMKGLSK AKEGVVAAAE KTKQGVAEAA GKTKEGVLYV GSKTKEGVVH GVATVAEKTK   60
EQVTNVGGAV VTGVTAVAQK TVEGAGSIAA ATGFVKKDQL GKNEEGAPQE GILEDMPVDP  120
DNEAYEMPSE EGYQDYEPEA                                              140

SEQ ID NO: 11            moltype = AA   length = 165
FEATURE                  Location/Qualifiers
REGION                   1..165
                         note = A-Syn-AAKK-BAP
source                   1..165
                         mol_type = protein
                         organism = synthetic construct
SEQUENCE: 11
MDVFMKGLSK AKEGVVAAAE KTKQGVAEAA GKTKEGVLYV GSKTKEGVVH GVATVAEKTK   60
EQVTNVGGAV VTGVTAVAQK TVEGAGNIAA ATGLVKKDQL AKQNEEGFLQ EGMVNNTDIP  120
VDPENEAYEM PPEEEYQDYE PEAGSAGGSG GLNDIFEAQK IEWHE                  165

SEQ ID NO: 12            moltype = AA   length = 165
FEATURE                  Location/Qualifiers
REGION                   1..165
                         note = A-Syn-BAAK-BAP
source                   1..165
                         mol_type = protein
                         organism = synthetic construct
SEQUENCE: 12
MDVFMKGLSM AKEGVVAAAE KTKQGVTEAA EKTKEGVLYV GSKTKEGVVH GVATVAEKTK   60
EQVTNVGGAV VTGVTAVAQK TVEGAGSIAA ATGFVKKDQL AKQNEEGFLQ EGMVNNTDIP  120
VDPENEAYEM PPEEEYQDYE PEAGSAGGSG GLNDIFEAQK IEWHE                  165
```

```
SEQ ID NO: 13              moltype = AA  length = 162
FEATURE                    Location/Qualifiers
REGION                     1..162
                           note = A-Syn-BBAA-BAP
source                     1..162
                           mol_type = protein
                           organism = synthetic construct
SEQUENCE: 13
MDVFMKGLSM AKEGVVAAAE KTKQGVTEAA EKTKEGVLYV GSKTREGVVQ GVASVAEKTK   60
EQASHLGGAV VTGVTAVAQK TVEGAGSIAA ATGFVKKDQL GKNEEGAPQE GILEDMPVDP  120
DNEAYEMPSE EGYQDYEPEA GSAGGSGGLN DIFEAQKIEW HE                     162

SEQ ID NO: 14              moltype = AA  length = 165
FEATURE                    Location/Qualifiers
REGION                     1..165
                           note = A-Syn-BBKK-BAP
source                     1..165
                           mol_type = protein
                           organism = synthetic construct
SEQUENCE: 14
MDVFMKGLSM AKEGVVAAAE KTKQGVTEAA EKTKEGVLYV GSKTREGVVQ GVASVAEKTK   60
EQASHLGGAV VTGVTAVAQK TVEGAGNIAA ATGLVKKDQL AKQNEEGFLQ EGMVNNTDIP  120
VDPENEAYEM PPEEEYQDYE PEAGSAGGSG GLNDIFEAQK IEWHE                  165

SEQ ID NO: 15              moltype = AA  length = 141
FEATURE                    Location/Qualifiers
REGION                     1..141
                           note = A-Syn-120-140_Del-BAP
source                     1..141
                           mol_type = protein
                           organism = synthetic construct
SEQUENCE: 15
MDVFMKGLSK AKEGVVAAAE KTKQGVAEAA GKTKEGVLYV GSKTKEGVVH GVATVAEKTK   60
EQVTNVGGAV VTGVTAVAQK TVEGAGSIAA ATGFVKKDQL GKNEEGAPQE GILEDMPVDG  120
SAGGSGGLND IFEAQKIEWH E                                            141

SEQ ID NO: 16              moltype = AA  length = 131
FEATURE                    Location/Qualifiers
REGION                     1..131
                           note = alpha-synuclein amino acids 1-119
source                     1..131
                           mol_type = protein
                           organism = synthetic construct
SEQUENCE: 16
MAHHHHHHIE GRMDVFMKGL SKAKEGVVAA AEKTKQGVAE AAGKTKEGVL YVGSKTKEGV   60
VHGVATVAEK TKEQVTNVGG AVVTGVTAVA QKTVEGAGSI AAATGFVKKD QLGKNEEGAP  120
QEGILEDMPV D                                                      131

SEQ ID NO: 17              moltype = AA  length = 107
FEATURE                    Location/Qualifiers
REGION                     1..107
                           note = kappa (LC constant region)
source                     1..107
                           mol_type = protein
                           organism = synthetic construct
SEQUENCE: 17
RTVAAPSVFI FPPSDEQLKS GTASVVCLLN NFYPREAKVQ WKVDNALQSG NSQESVTEQD   60
SKDSTYSLSS TLTLSKADYE KHKVYACEVT HQGLSSPVTK SFNRGEC                107

SEQ ID NO: 18              moltype = AA  length = 329
FEATURE                    Location/Qualifiers
REGION                     1..329
                           note = IgG1 (HC Constant region)
source                     1..329
                           mol_type = protein
                           organism = synthetic construct
SEQUENCE: 18
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329
```

```
SEQ ID NO: 19           moltype = AA   length = 4
FEATURE                 Location/Qualifiers
REGION                  1..4
                        note = GM285 epitope 112-115
source                  1..4
                        mol_type = protein
                        organism = synthetic construct
SEQUENCE: 19
ILED                                                                    4

SEQ ID NO: 20           moltype = AA   length = 13
FEATURE                 Location/Qualifiers
REGION                  1..13
                        note = GM285 CDR1 Heavy Chain
source                  1..13
                        mol_type = protein
                        organism = synthetic construct
SEQUENCE: 20
AASGFTFSRF TMT                                                         13

SEQ ID NO: 21           moltype = AA   length = 17
FEATURE                 Location/Qualifiers
REGION                  1..17
                        note = GM285 CDR2 Heavy Chain
source                  1..17
                        mol_type = protein
                        organism = synthetic construct
SEQUENCE: 21
AISGSGGGTS YADSVKG                                                     17

SEQ ID NO: 22           moltype = AA   length = 9
FEATURE                 Location/Qualifiers
REGION                  1..9
                        note = GM285 CDR3 Heavy Chain
source                  1..9
                        mol_type = protein
                        organism = synthetic construct
SEQUENCE: 22
AKNWAPFDY                                                               9

SEQ ID NO: 23           moltype = AA   length = 12
FEATURE                 Location/Qualifiers
REGION                  1..12
                        note = GM285 CDR1 Light Chain
source                  1..12
                        mol_type = protein
                        organism = synthetic construct
SEQUENCE: 23
RASQSVSRSY LA                                                          12

SEQ ID NO: 24           moltype = AA   length = 7
FEATURE                 Location/Qualifiers
REGION                  1..7
                        note = GM285 CDR2 Light Chain
source                  1..7
                        mol_type = protein
                        organism = synthetic construct
SEQUENCE: 24
GASSRAT                                                                 7

SEQ ID NO: 25           moltype = AA   length = 9
FEATURE                 Location/Qualifiers
REGION                  1..9
                        note = GM285 CDR3 Light Chain
source                  1..9
                        mol_type = protein
                        organism = synthetic construct
SEQUENCE: 25
QQYGSSPWT                                                               9
```

```
SEQ ID NO: 26              moltype = AA  length = 116
FEATURE                    Location/Qualifiers
REGION                     1..116
                           note = GM285 VH
source                     1..116
                           mol_type = protein
                           organism = synthetic construct
SEQUENCE: 26
EVQLLESGGG LVQPGGSLRL SCAASGFTFS RFTMTWVRQA PGKGLEWVSA ISGSGGGTSY    60
ADSVKGRLTV SRDNSKNTLY LQMNSLRAED TAVYYCAKNW APFDYWGQGT LVTVSS       116

SEQ ID NO: 27              moltype = AA  length = 108
FEATURE                    Location/Qualifiers
REGION                     1..108
                           note = GM285 VL
source                     1..108
                           mol_type = protein
                           organism = synthetic construct
SEQUENCE: 27
EIVLTQSPGT LSLSPGERAT LSCRASQSVS RSYLAWYQQK PGQAPRLLIY GASSRATGIP    60
DRFSGSGSGT DFTLTVSRLE PEDFAVYYCQ QYGSSPWTFG QGTKVEIK                108

SEQ ID NO: 28              moltype = AA  length = 329
FEATURE                    Location/Qualifiers
REGION                     1..329
                           note = GM285 IgG1 constant region
source                     1..329
                           mol_type = protein
                           organism = synthetic construct
SEQUENCE: 28
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 29              moltype = AA  length = 106
FEATURE                    Location/Qualifiers
REGION                     1..106
                           note = GM285 Kappa chain
source                     1..106
                           mol_type = protein
                           organism = synthetic construct
SEQUENCE: 29
TVAAPSVFIF PPSDEQLKSG TASVVCLLNN FYPREAKVQW KVDNALQSGN SQESVTEQDS    60
KDSTYSLSST LTLSKADYEK HKVYACEVTH QGLSSPVTKS FNRGEC                 106

SEQ ID NO: 30              moltype = AA  length = 116
FEATURE                    Location/Qualifiers
REGION                     1..116
                           note = GM37 Variant 1 heavy chain
source                     1..116
                           mol_type = protein
                           organism = synthetic construct
SEQUENCE: 30
EVQLLESGGG LVQTGGSLRL SCAASGFTFS SYAMTWVRQA PGKGLEWVSA IRSSGDRTDY    60
ADSVKGRFTI SRDNSQNTLY LQMNSLRAED TAVYYCAKNW APFDSWGQGT LVTVSS       116

SEQ ID NO: 31              moltype = AA  length = 116
FEATURE                    Location/Qualifiers
REGION                     1..116
                           note = GM 37 variant 2 heavy chain
source                     1..116
                           mol_type = protein
                           organism = synthetic construct
SEQUENCE: 31
EVQLLESGGG LVQTGGSLRL SCAASGFTFS SYAMTWVRQA PGKGLEWVSA IRSQGDRTDY    60
ADSVKGRFTI SRDNSQNTLY LQMNSLRAED TAVYYCAKNW APFDSWGQGT LVTVSS       116
```

```
SEQ ID NO: 32           moltype = AA   length = 116
FEATURE                 Location/Qualifiers
REGION                  1..116
                        note = GM 37 variant 3 heavy chain
source                  1..116
                        mol_type = protein
                        organism = synthetic construct
SEQUENCE: 32
EVQLLESGGG LVQTGGSLRL SCAASGFTFS SYAMTWVRQA PGKGLEWVSA IRSHGDRTDY    60
ADSVKGRFTI SRDNSQNTLY LQMNSLRAED TAVYYCAKNW APFDSWGQGT LVTVSS       116

SEQ ID NO: 33           moltype = AA   length = 17
FEATURE                 Location/Qualifiers
REGION                  1..17
                        note = GM37 variant 1 heavy chain CDR 2
source                  1..17
                        mol_type = protein
                        organism = synthetic construct
SEQUENCE: 33
AIRSSGDRTD YADSVKG                                                  17

SEQ ID NO: 34           moltype = AA   length = 17
FEATURE                 Location/Qualifiers
REGION                  1..17
                        note = GM37 variant 2 CDR 2 heavy chain
source                  1..17
                        mol_type = protein
                        organism = synthetic construct
SEQUENCE: 34
AIRSQGDRTD YADSVKG                                                  17

SEQ ID NO: 35           moltype = AA   length = 17
FEATURE                 Location/Qualifiers
REGION                  1..17
                        note = GM37 variant 3 CDR 2 heavy chain
source                  1..17
                        mol_type = protein
                        organism = synthetic construct
SEQUENCE: 35
AIRSHGDRTD YADSVKG                                                  17

SEQ ID NO: 36           moltype = AA   length = 5
FEATURE                 Location/Qualifiers
REGION                  1..5
                        note = 9E4 binding epitope
source                  1..5
                        mol_type = protein
                        organism = synthetic construct
SEQUENCE: 36
NEAYE                                                               5

SEQ ID NO: 37           moltype = AA   length = 134
FEATURE                 Location/Qualifiers
REGION                  1..134
                        note = HUMAN Beta-synuclein
source                  1..134
                        mol_type = protein
                        organism = synthetic construct
SEQUENCE: 37
MDVFMKGLSM AKEGVVAAAE KTKQGVTEAA EKTKEGVLYV GSKTREGVVQ GVASVAEKTK    60
EQASHLGGAV FSGAGNIAAA TGLVKREEFP TDLKPEEVAQ EAAEEPLIEP LMEPEGESYE   120
DPPQEEYQEY EPEA                                                    134

SEQ ID NO: 38           moltype = AA   length = 127
FEATURE                 Location/Qualifiers
REGION                  1..127
                        note = HUMAN Gamma-synuclein
source                  1..127
                        mol_type = protein
                        organism = synthetic construct
SEQUENCE: 38
MDVFKKGFSI AKEGVVGAVE KTKQGVTEAA EKTKEGVMYV GAKTKENVVQ SVTSVAEKTK    60
EQANAVSEAV VSSVNTVATK TVEEAENIAV TSGVVRKEDL RPSAPQQEGE ASKEKEEVAE   120
EAQSGGD                                                            127
```

```
SEQ ID NO: 39            moltype = AA  length = 140
FEATURE                  Location/Qualifiers
REGION                   1..140
                         note = alpha-synuclein ortholog for Cynomolgus monkey
source                   1..140
                         mol_type = protein
                         organism = synthetic construct
SEQUENCE: 39
MDVFMKGLSK AKEGVVAAAE KTKQGVAEAA GKTKEGVLYV GSKTKEGVVH GVATVAEKTK    60
EQVTNVGGAV VTGVTAVAQK TVEGAGSIAA ATGFIKKDQL GKNEEGAPQE GILQDMPVDP   120
DNEAYEMPSE EGYQDYEPEA                                              140

SEQ ID NO: 40            moltype = AA  length = 140
FEATURE                  Location/Qualifiers
REGION                   1..140
                         note = alpha-synuclein ortholog for Rat
source                   1..140
                         mol_type = protein
                         organism = synthetic construct
SEQUENCE: 40
MDVFMKGLSK AKEGVVAAAE KTKQGVAEAA GKTKEGVLYV GSKTKEGVVH GVTTVAEKTK    60
EQVTNVGGAV VTGVTAVAQK TVEGAGNIAA ATGFVKKDQM GKGEEGYPQE GILEDMPVDP   120
SSEAYEMPSE EGYQDYEPEA                                              140

SEQ ID NO: 41            moltype = AA  length = 140
FEATURE                  Location/Qualifiers
REGION                   1..140
                         note = alpha-synuclein ortholog for Mouse
source                   1..140
                         mol_type = protein
                         organism = synthetic construct
SEQUENCE: 41
MDVFMKGLSK AKEGVVAAAE KTKQGVAEAA GKTKEGVLYV GSKTKEGVVH GVTTVAEKTK    60
EQVTNVGGAV VTGVTAVAQK TVEGAGNIAA ATGFVKKDQM GKGEEGYPQE GILEDMPVDP   120
GSEAYEMPSE EGYQDYEPEA                                              140

SEQ ID NO: 42            moltype = AA  length = 446
FEATURE                  Location/Qualifiers
REGION                   1..446
                         note = 9E4 HC
source                   1..446
                         mol_type = protein
                         organism = synthetic construct
SEQUENCE: 42
EVQLVESGGG LVQPGGSLRL SCAASGFTFS NYGMSWVRQA PGKGLEWVAS ISSGGGSTYY    60
PDNVKGRFTI SRDNAKNSLY LQMNSLRAED TAVYYCARGG AGIDYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446

SEQ ID NO: 43            moltype = AA  length = 220
FEATURE                  Location/Qualifiers
REGION                   1..220
                         note = 9E4 LC
source                   1..220
                         mol_type = protein
                         organism = synthetic construct
SEQUENCE: 43
DIQMTQSPSS LSASVGDRVT ITCKSIQTLL YSSNQKNYLA WFQQKPGKAP KLLIYWASIR    60
KSGVPSRFSG SGSGTDFTLT ISSLQPEDLA TYYCQQYYSY PLTFGGGTKL EIKRTVAAPS   120
VFIFPPSDEQ LKSGTASVVC LLNNFYPREA KVQWKVDNAL QSGNSQESVT EQDSKDSTYS   180
LSSTLTLSKA DYEKHKVYAC EVTHQGLSSP VTKSFNRGEC                        220
```